US009987340B2

(12) United States Patent
Caggiano et al.

(10) Patent No.: US 9,987,340 B2
(45) Date of Patent: *Jun. 5, 2018

(54) COMPOSITIONS AND METHODS OF USING CHONDROITINASE ABCI MUTANTS

(71) Applicant: ACORDA THERAPEUTICS, INC., Ardsley, NY (US)

(72) Inventors: Anthony O. Caggiano, Larchmont, NY (US); Andrea Vecchione, Mt. Vernon, NY (US); Jennifer Iaci, Boonton, NJ (US)

(73) Assignee: Acorda Therapeutics, Inc., Ardsley, NY (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/230,040

(22) Filed: Aug. 5, 2016

(65) Prior Publication Data

US 2017/0028038 A1 Feb. 2, 2017

Related U.S. Application Data

(60) Continuation of application No. 14/790,075, filed on Jul. 2, 2015, now Pat. No. 9,410,141, which is a division of application No. 13/849,420, filed on Mar. 22, 2013, now Pat. No. 9,102,930, which is a continuation of application No. 12/781,762, filed on May 17, 2010, now Pat. No. 8,404,232, which is a division of application No. 11/870,350, filed on Oct. 10, 2007, now Pat. No. 7,722,864.

(60) Provisional application No. 60/828,800, filed on Oct. 10, 2006.

(51) Int. Cl.
| | | |
|---|---|---|
| C12N 9/88 | (2006.01) | |
| C12N 9/20 | (2006.01) | |
| C12N 9/24 | (2006.01) | |
| C12N 9/14 | (2006.01) | |
| C12N 15/64 | (2006.01) | |
| C12P 19/34 | (2006.01) | |
| C12P 21/06 | (2006.01) | |
| C07H 21/04 | (2006.01) | |
| C07K 1/00 | (2006.01) | |
| A61M 37/00 | (2006.01) | |
| A61K 38/00 | (2006.01) | |
| A61K 38/46 | (2006.01) | |
| A61K 38/51 | (2006.01) | |

(52) U.S. Cl.
CPC ............. *A61K 38/51* (2013.01); *C12N 9/88* (2013.01); *C12Y 402/0202* (2013.01); *C12Y 402/02021* (2013.01); *A61K 38/00* (2013.01)

(58) Field of Classification Search
CPC .......... A61K 38/00; A61K 38/51; C12N 9/88; C12Y 402/02021; C12Y 402/0202

USPC .......... 435/232, 201, 200, 195, 91.41, 91.1, 435/69.1; 424/94.5, 94.62; 536/23.1, 536/23.2; 530/350; 604/4.01
See application file for complete search history.

(56) References Cited

U.S. PATENT DOCUMENTS

| | | |
|---|---|---|
| 5,262,522 A | 11/1993 | Gearing |
| 5,270,194 A | 12/1993 | D'Alterio et al. |
| 5,496,718 A | 3/1996 | Hashimoto |
| 5,498,536 A | 3/1996 | Khandke |
| 5,578,480 A | 11/1996 | Khandke |
| 5,652,122 A | 7/1997 | Frankel et al. |
| 5,670,617 A | 9/1997 | Frankel et al. |
| 5,674,980 A | 10/1997 | Frankel et al. |
| 5,747,641 A | 5/1998 | Frankel et al. |
| 5,763,205 A | 6/1998 | Hashimoto et al. |
| 5,792,743 A | 8/1998 | Schachner |
| 5,804,604 A | 9/1998 | Frankel et al. |
| 5,869,301 A | 2/1999 | Nghiem et al. |
| 5,997,863 A | 12/1999 | Zimmerman et al. |
| 6,007,810 A | 12/1999 | Ishikawa et al. |
| 6,063,378 A | 5/2000 | Nohara et al. |
| 6,093,563 A | 7/2000 | Bennett et al. |
| 6,153,187 A | 11/2000 | Yacoby-Zeevi |
| 6,171,575 B1 | 1/2001 | Okuyama |
| 6,184,023 B1 | 2/2001 | Hashimoto et al. |
| 6,200,564 B1 | 3/2001 | Lamont et al. |
| 6,248,562 B1 | 6/2001 | Dunn et al. |
| 6,254,870 B1 | 7/2001 | Staten et al. |
| 6,313,265 B1 | 11/2001 | Phillips et al. |
| 6,326,166 B1 | 12/2001 | Pomerantz et al. |

(Continued)

FOREIGN PATENT DOCUMENTS

| | | |
|---|---|---|
| AU | 2003/208466 B2 | 9/2003 |
| AU | 2003/265561 A1 | 3/2004 |

(Continued)

OTHER PUBLICATIONS

Tkalec et al. "Isolation and Expression in *Escherichia coli* ofcslA and cslB, Genes Coding for the Chondroitin Sulfate-Degrading Enzymes Chondroitinase AC and Chondroitinase B, Respectively, From Flavobacterium Heparinum" (2000) Appl. Environ. Microbiol. 66(1):29-35.

(Continued)

*Primary Examiner* — Ganapathirama Raghu
(74) *Attorney, Agent, or Firm* — Pepper Hamilton LLP

(57) ABSTRACT

The present disclosure relates to protein and nucleic acid mutants of chondroitinase ABCI. Such nucleic acid mutants encode for chondroitinase ABCI mutant enzymes exhibiting altered chondroitin lyase activity or increased resistance to inactivation from stressors including UV light or heat. Methods of using such nucleic acid mutants encoding chondroitinase ABCI mutant enzymes is also provided.

12 Claims, 3 Drawing Sheets

(56) References Cited

U.S. PATENT DOCUMENTS

| | | | |
|---|---|---|---|
| 6,972,168 | B2 | 8/2005 | Muir et al. |
| 7,008,783 | B1 | 3/2006 | Sato et al. |
| 7,074,581 | B2 | 7/2006 | Yamashita et al. |
| 7,163,545 | B2 | 1/2007 | Yaszemski et al. |
| 7,465,705 | B2 | 12/2008 | Lee et al. |
| 7,507,570 | B2 | 3/2009 | Prabhakar et al. |
| 7,560,106 | B2 | 7/2009 | Sasisekharan et al. |
| 7,722,864 | B2 | 5/2010 | Caggiano et al. |
| 8,404,232 | B2* | 3/2013 | Caggiano .............. C12N 9/88 424/94.5 |
| 9,102,930 | B2* | 8/2015 | Caggiano .............. C12N 9/88 |
| 9,410,141 | B2* | 8/2016 | Caggiano .............. C12N 9/88 |
| 2003/0040112 | A1 | 2/2003 | Muir et al. |
| 2003/0072749 | A1 | 4/2003 | Muir et al. |
| 2003/0077258 | A1 | 4/2003 | Muir |
| 2004/0033221 | A1 | 2/2004 | Masuda et al. |
| 2004/0265297 | A1 | 12/2004 | Gruskin et al. |
| 2005/0118157 | A1 | 6/2005 | McMahon et al. |
| 2005/0233419 | A1 | 10/2005 | Pojasek et al. |
| 2006/0078959 | A1 | 4/2006 | Prabhaker et al. |
| 2006/0153827 | A1 | 7/2006 | Gruskin et al. |
| 2006/0233782 | A1 | 10/2006 | Gruskin et al. |
| 2007/0104703 | A1 | 5/2007 | Caggiano et al. |
| 2007/0274979 | A1 | 11/2007 | Gruskin et al. |
| 2009/0060895 | A1 | 3/2009 | Caggiano et al. |
| 2011/0250631 | A1 | 10/2011 | Gruskin et al. |
| 2011/0262413 | A1 | 10/2011 | Gruskin et al. |
| 2012/0207732 | A1 | 8/2012 | Gruskin et al. |
| 2012/0308547 | A1 | 12/2012 | Caggiano et al. |
| 2013/0210082 | A1 | 8/2013 | Caggiano et al. |
| 2013/0243765 | A1 | 9/2013 | Gruskin et al. |
| 2014/0193387 | A1 | 7/2014 | Gruskin et al. |
| 2014/0248253 | A1 | 9/2014 | Gruskin et al. |
| 2014/0322192 | A1 | 10/2014 | Gruskin et al. |
| 2015/0023942 | A1 | 1/2015 | Gruskin et al. |
| 2015/0190483 | A1 | 7/2015 | Caggiano et al. |
| 2015/0299687 | A1 | 10/2015 | Gruskin et al. |
| 2018/0066245 | A1 | 3/2018 | Caggiano et al. |
| 2018/0073007 | A9 | 3/2018 | Gruskin et al. |

FOREIGN PATENT DOCUMENTS

| | | |
|---|---|---|
| AU | 2004/241088 A1 | 12/2004 |
| AU | 2006/294755 B2 | 4/2012 |
| CA | 2071898 A1 | 4/1991 |
| CA | 2364690 A1 | 10/2000 |
| CA | 2455827 A1 | 2/2003 |
| CA | 2623635 C | 4/2013 |
| EP | 0704532 A2 | 4/1996 |
| EP | 1631234 A2 | 3/2006 |
| EP | 1646353 A2 | 4/2006 |
| EP | 2353606 A2 | 8/2011 |
| EP | 2354155 A2 | 8/2011 |
| EP | 1631234 B1 | 9/2011 |
| JP | H10-174598 | 6/1998 |
| JP | 2004-113166 | 4/2004 |
| WO | WO 1991/06303 A | 5/1991 |
| WO | WO 1994/25567 A1 | 11/1994 |
| WO | WO 1995/13091 A1 | 5/1995 |
| WO | WO 1995/14478 A1 | 6/1995 |
| WO | WO 1996/01894 A1 | 1/1996 |
| WO | WO 1999/46364 | 9/1999 |
| WO | WO 1999/46368 A2 | 9/1999 |
| WO | WO 2000/52149 A1 | 9/2000 |
| WO | WO 2000/59942 A2 | 10/2000 |
| WO | WO 2000/62067 A1 | 10/2000 |
| WO | WO 2000/64482 A1 | 11/2000 |
| WO | WO 2000/075319 A1 | 12/2000 |
| WO | WO 2001/39795 A2 | 6/2001 |
| WO | WO 2002/08285 A2 | 1/2002 |
| WO | WO 2002/055684 A | 7/2002 |
| WO | WO 2002/65136 A2 | 8/2002 |
| WO | WO 2002/083179 A2 | 10/2002 |
| WO | WO 2003/000901 A2 | 1/2003 |
| WO | WO 2003/015612 A2 | 2/2003 |
| WO | WO 2003/22882 A2 | 3/2003 |
| WO | WO 2003/31578 A2 | 4/2003 |
| WO | WO 2003/074080 A1 | 9/2003 |
| WO | WO 2003/100031 A2 | 12/2003 |
| WO | WO 2003/102160 A2 | 12/2003 |
| WO | WO 2004/017044 A2 | 2/2004 |
| WO | WO 2004/103299 A2 | 12/2004 |
| WO | WO 2004/108069 A2 | 12/2004 |
| WO | WO 2004/110359 A2 | 12/2004 |
| WO | WO 2004/110360 A2 | 12/2004 |
| WO | WO 2005/112986 A2 | 12/2004 |
| WO | WO 2005/087920 A2 | 9/2005 |
| WO | WO 2007/038548 A2 | 4/2007 |
| WO | WO 2008/045970 A2 | 4/2008 |

OTHER PUBLICATIONS

Accession P59807, Aug. 15, 2003 UniProtKB/Swiss-Prot.

Aldrich "Enzymer Explorer" 2009, URL: http://www.sigmaaldrich.com/life-science/metabolomics/enzyme-explorer/learning-center/carbohydrate-analysis/carbohydrate-analysis-iii.

Anderson et al. "Tumor Cell Retention of Antibody Fab Fragments is Enhanced by an Attached HIV TAT Protein-Derived Peptide" 1993, *Biochem. & Biophys. Res. Commun.* 194(2):876-884.

Appel et al. "Several Extracellular Domains of the Neural Cell Adhesion Molecule L1 are Involved in Neurite Outgrowth and Cell Body Adhesion" 1993, *J. Neurosc.* 13(11): 4764-4775.

Avrameas et al. "Polyreactive anti-DNA monoclonal antibodies and a derived peptide as vectors for the intracytoplasmic and intranuclear translocation of macromolecules" 1998, *Proc. Natl. Acad. Sci. USA* 95:5601-5606.

Banker et al. "Modern Pharmaceutics" 1979, Marcel Dekker, Inc. (TOC).

Banker et al. "Modern Pharmaceutics" 2002, 4th Ed., Informa Healthcare, New York (TOC).

Bao et al. "A Functional Dermatan Sulfate Epitope Containing Iduronate (2-O-sulfate) α1-3GalNAC (6-O-sulfate) Disaccharide in the Mouse Brain" 2005, *J. of Bio. Chem.* 280(24):23184-23193.

Basso et al. "A Sensitive and Reliable Locomotor Rating Scale for Open Field Testing in Rats" 1995, *J. of Neurotrama* 12(1):1-21.

Becker-Hapak et al. "TAT-Mediated Protein Transduction into Mamalian Cells" 2001, *Methods* 24:247-256.

Ben-Bassat et al. "Processing of the Initiation Methionine from Proteins: Properties of the *Escherichia coli* Methionine Aminopeptidase and Its Gene Structure" 1987, *J. Bacteriol.* 169(2):751-757.

Bixby et al. "Neurite outgrowth on muscle cell surfaces involves extracellular matrix receptors as well as $Ca^{2+}$-dependent and -independent cell adhesion molecules" 1987, *Proc. Natl. Acad. Sci. USA* 84:2555-2559.

Blight et al. "Animal models of spinal cord injury" 2002, *Top Spinal Cord Inj. Rehabi.* 6(2):1-13.

Bowie et al. "Deciphering the Message in Protein Sequences: Tolerance to Amino Acid Substitutions" 1990, *Science* 247:1306-1319.

Bradbury et al. "Chondroitinase ABC Promotes Functional Recovery After Spinal Cord Injury" 2002, *Nature* 416:636-640.

Bradbury et al. "Chondroitinase ABC Promotes Regeneration and Functional Recovery Following Spinal Cord Injury" 2001, *Soc. for Neuroscience Abstracts* 27(2):1835.

Bradbury et al. "NT-3 Promotes Growth of Lesioned Adult Rat Sens Ory Axons Ascending in the Dorsal Columns of the Spinal Cord" 1999, *Eur. J. Neurosc.* 11(11):3873-3783.

Bray et al. "Neuronal and Nonneuronal Influences on Retinal Ganglion Cell Survival, Axonal Regrowth, and Connectivity after Axotomy" 1991, Ann. NY Acad. Sci., 214-228.

Broach et al. "Experimental Manipulation of Gene Expression" M. Inouye ed., Academic Press, New York, 1983, pp. 83-117.

Burgess et al. "Possible Dissassociation of the Heparin-binding and Mitogenic Activities of Heparin-binding (Acidic Fibroblast)

(56) References Cited

OTHER PUBLICATIONS

Growth Factor-1 From Its Receptor-binding Activities by Site-directed Mutagenesis of a Single Lysine Residue" 1990, *J. of Cell. Bio.* 111:2129-2138.

Cadelli et al. "Oligodendrocyte- and Myelin-Associated Inhibitors of Neurite Outgrowth: Their Involvement in the Lack of CNS Regeneration" 1992, *Exp. Neur.* 115:189-192.

Caggiano et al., Chondroitinase ABCI Improves Locomotion and Bladder Function following Contusion Injury of the Rat Spinal Cord, Feb. 1, 2005, *J. Neurotrauma* 22(2):226-239.

Cajal "Degeneration & Regeneration of the Nervous System" May 1959 ed., Hafner Publ. Co., New York (TOC).

Chang et al. "Extension of Neurites on Axons is Impaired by Antibodies against Specific Neural Cell Surface Glycoproteins" 1987, *J. Cell. Biol.* 104:355-362.

Chau et al. "Chondroitinase ABC Enhances Axonal Regrowth Through Schwann Cell-seeded Guidance Channels After Spinal Cord Injury" Nov. 20, 2003 *FASEB J.* 18(1):1-24.

Chen et al. "Peripheral nerve regeneration using silicone rubber chambers filled with collagen, laminin and fibronectin" 2000, *Biomat.* 21:1541-1547.

Crespo et al. "How Does Chondroitinase Promote Functional Recovery in the Damaged CNS?" 2007, *Ex. Neurology* 206:159-171.

Curinga et al. "Mammalian-produced Chondroitinase AC Mitigates Axon Inhibition by Chondroitin Sulfate Proteoglycans" 2007, *J. of Neurochemistry* 102:275-288.

Daichi "Text Book of Physiology" 2000, 3$^{rd}$ Ed. 81.

Degrendele et al. "Requirement for CD44 in Activated T Cell Extravassation into an Inflammatory Site" 1997, *Science* 278:672-675.

Denuziere et al. "Chitosan-Chondroitin sulfate and chitosan-hyaluronate polyelectrolyte complexes: biological properties" 1998, *Biomaterials* 19:1275-1285.

Derossi et al. "Cell Internalization of the Third Helix of the Antennapedia Homeodomain is Receptorindependent" 1996, *J. Bioi. Chern* 271:18188-18193.

Dimayuga et al. "The Neuregulin GGF2 Attenuates Free Radical Release from Activated Microglial Cells" Mar. 2003, *J. Neuroim.* 136(1-2):67-74.

Doppenberg et al. "Clinical Trials in Traumatic Brain Injury" 1998, *Ann. NY Acad. Sci.* 305-319.

Edelman "Cell Adhesion Molecules" 1983, *Science* 219:450-457.

Edelman et al. "Morphoregulatory Molecules" 1990, Wiley, New York (TOC).

Efthymiadis et al. "The HIV-1 Tat Nuclear Localization Sequence Confers Novel Nuclear Import Properties" Jan. 16, 1998, *J. Biol. Chern.* 273(3):1623-1628.

Ellioit et al. "Intercellular Trafficking and Protein Delivery by a Herpesvirus Structural Protein" 1997, *Cell* 88:223-233.

European Search Report and Written Opinion for EP04752310 dated Oct. 7, 2008.

European Search Report and Written Opinion for EP06815505 dated Feb. 22, 2010.

European Search Report and Written Opinion for EP10183555 dated Jan. 20, 2011.

European Search Report and Written Opinion for EP10184697 dated Jul. 12, 2011.

European Search Report and Written Opinion for EP11152626 dated Jul. 21, 2011.

Fahraeus et al. "Inhibition of pRb phosphorylation and cell-cycle progression by a 20-residue peptide derived from p16CDKN2IINK4A" 1996, *Curr. Biol.* 6(1):84-91.

Favre et al. "Hyaluronidase enhances recombinant adeno-associated virus (Raav)-mediated gene transfer in the rat skeletal muscle" 2000, Gene Ther. 7(16):1417-1420.

Fawcett et al. "The glial scar and central nervous system repair" 1999, *Brain Res. Bull.* 49(6):377-391.

Fawell et al. "Tat-mediated delivery of heterologous proteins into cells" 1994, *Proc. Natl. Acad. Sci. USA* 91:664-668.

Fethiere et al. "Crystal Structure of Chondroitin AC Lyase, a Representative of a family of Glycosaminoglycan Degrading Enzymes" 1999, *J. Mol. Biol.* 288:635-647.

Fongmoon et al. "Chondroitinase-mediated Degradation of Rare 3-)-Sulfated Glucuronic Acid in Functional Oversulfated Chondroitin Sulfate K and E" 2007, *J. of Bio. Chem.* 282(51):36895-39904.

Frankel et al. "Tat Protein from Human Immunodeficiency Virus Forms a Metal-Linked Dimer" 1988, *Science* 240:70-73.

Frankish et al. "Spinal-cord Repair Moves a Step Closer" 2002, *The Lancet* 359(9314):1317.

Gennaro "Remington's Pharmaceutical Sciences" 1985, Mack Publishing Company (PA) 17$^{th}$ Ed. (TOC).

Goodman et al. "The Pharmacological Basis of Therapeutics" 1980, 6$^{th}$ ed., MacMillan Pub., New York (TOC).

Goodman et al. "The Pharmacological Basis of Therapeutics" 2001, 10$^{th}$ ed., McGraw Hill, New York (TOC).

Grandpre et al. "Nogo-66 Receptor Antagonist Peptide Promotes Axonal Regeneration" May 30, 2002, *Nature* 417(6888):547-551.

Hamai et al. "Two Distinct Chondroitin Sulfate ABC Lyases" 1997, *J. Biol. Chem.* 272(14):9123-9130.

Hirschberg et al. "Inflammation after axonal injury has conflicting consequences for recovery of function: rescue of spared axons is impaired but regeneration is supported" 1994, *J. Neuroimmunol.* 50(1):9-16 (Abstract).

Hiyama et al. "Crystallization and Some Properties of Chondroitinase from Arthrobacter Aurescens" 1975, *J. Biol. Chem.* 250:1824-1828.

Hlavin et al. "Molecular Structure and Functional Testing of Human L1CAM: An Interspecies Comparison" 1991, *Genomics* 11:416-423.

Hoffman et al. "Chondroitin Sulfates" 1958, *Federation Proc.* 17:1078-1082.

Horstkorte et al. "The Fourth Immunoglobin-like Domain of NCAM Contains a Carbohydrate Recognition Domain for Oligomannosidic Glycans Implicated in Associated with L1 and Neurite Outgrowth" 1993, *J. Cell Biol.* 121(6):1409-1421.

Hou et al. "Endotoxin Removal by Anion-Exchange Polymeric Matrix" 1990, *Biotech. Appl. Biochem.* 12:315-324.

Huang et al. "Active Site of Chondroitin AC Lyase Revealed by the Structure of Enzyme-Oligosaccharide Complexes and Mutagenesis" Jan. 1, 2001, *Biochemistry*, 40(8):2359-2372.

Huang et al. "Crystal Structure of Chondroitinase B from Flavobacterium heparinum and its Complex with a Disaccharide Product at 107 A Resolution" 1999, *J. Mol. Biol.* 294:1257-1269.

Huang et al. "Crystal Structure of *Proteus vulgaris* Chondroitin Sulfate ABC Lyase I at 1.9 A Resolution" May 2, 2003, *J. Mol. Biol.* 328(3):623-634.

Hunt et al. "The Nogo Receptor, Its Ligands and Axonal Regeneration in the Spinal Cord; a Review" Feb. 2002, *J. Neurocytology* 31(2):93-120.

Iida et al. "Cell Surface Chondroitin Sulfate Proteoglycans in Tumor Cell Adhesion, Motility and Invastion" 1996, *Seminars in Cancer Biology* 7:155-162.

Iwai et al. "Axon Patterning Requires DN-cadherin, a Novel Neuronal Adhesion Receptor, in the *Drosphila* Embryonic CNS" 1997, Neuron 19:77-89.

Jones "Taking a new TAK on Tat transactivation" 1997, *Genes & Dev.* 11:2593-2599.

Jung et al. "Transit time of leutocytes rolling through venules controls cytokine-induced inflammatory cell recruitment in vivo" 1998, *J. Clin. Invest.* 102(8):1526-1533.

Kadmon et al. "Functional Cooperation between the Neural Adhesion Molecules L1 and N-CAM is Carbohydrate Dependent" 1990, *J. Cell Biol.* 110:209-218.

Kadmon et al. "The Neural Cell Adhesion Molecule N-CAM Enhances L1-dependent Cell-Cell Interactions" 1990, *J. Cell Biol.* 110:193-208.

Khan et al. "Animal Models of Spinal Cord Contusion Injuries" 1999, Laboratory Animal Science 49(2): 161-172.

Kim et al. "Insertion and Deletion Mutants of FokI Restriction Endonuclease" 1994, *J. Biol. Chem.* 269(50):31978-31982.

(56) References Cited

OTHER PUBLICATIONS

Korn "The Degradation of Heparin by Bacterial Enzymes" 1957, *J. Biol. Chem.* 226:841-844.
Krekoski et al. "Axonal Regeneration into Acellular Nerve Grafts is Enhanced by Degradation of Chondroitin Sulfate Proteoglycan" 2001, *J. Neurosci.* 15:21(16):6206-6213.
Kubota et al. "Functional Similarity of HIV-1 Rev and HTLV-1 Rex Proteins: Identification of a New Nucleolar-Targeting Signal in Rev Protein" Aug. 15, 1989, *Biochem. Biophys. Res. Commun.* 162(3):963-970.
Kwon et al. "Animal Models Used in Spinal Cord Regeneration Research" 2002, *Spine* 27(14):1504-1510.
Lagenaur et al. "An L1-like molecule, the 8D9 antigen, is a potent substrate for neurite extension" 1987, *Proc. Natl. Acad. Sci. USA* 84:7753-7757.
Lemons et al. "Chondroitin Sulfate Preteoglycan Immunoreactivity Increases Following Spinal Cord Injury and Transplantation" 1999, *Exper. Neurology* 160:51-65.
Lesley et al. "Variant Cell Lines Selected for Alterations in the Function of the Hyaluronan Receptor CD44 Show Differences in Glycosylation" 1995, *J. Exp. Med.* 182:431-437.
Li et al. "Delayed systemic Nogo-66 Receptor Antagonist Promotes Recovery from Spinal Cord Injury" 2003, *J. Neuroscience* 23(10):4219-4227.
Lindner et al. "L1 mono- and polyclonal antibodies modify cell migration in early postnatal mouse cerebellum" 1983, *Nature* 305:427-430.
Lodish et al. "Integrating cells into tissue" 2000, Mol. Cell Biology, 5$^{th}$ Ed., Chapter 6.
Mahanthappa et al. "Glial Growth Factor 2, a Soluble Neuregulin, Directly Increases Schwann Cell Motility and Indirectly Promotes Neurite Outgrowth" 1996, *J. Neuroscience* 16(15):4673-4683.
Maniatis et al. "Molecular Cloning: A Laboratory Manual" 1982, Cold Spring Harbor Lab. (TOC).
Mann et al. "Endocytosis and Targeting of Exogenous HIV-1 Tat Protein" Jul. 10, 1991, *EMBO J.* (7):1733-1739.
Martinez et al. "Purification and Properties of the Enzyme Chondroitinase" 1959, *J. Biol. Chem.* 234(9):2236-2239.
Martini et al. "Restricted Localization of L1 and N-CAM Sites of Contact Between Schwann Cells and Neurites in Culture" 1994, *GLIA* 10:70-74.
Matinysn "Restoration of functions due to Enzyme Therepy After Complete Transaction of the Spinal Cord" 1965, *ZH EK SP KLIN MED* 5(3):3-13.
Matsumoto et al. "Peripheral nerve regeneration across an 80-mm gap bridged by a polyglycolic acid (PGA)-collagen tube filled with laminin-coated collagen fibers: a histilogical and electrophysiological evaluation of regenerated nerves" 2000, *Brain Res.* 868:315-328.
Matteuci et al. "Synthesis of Deoxyoligonucleotides on a Polymer Support" 1981, *J. Am. Chem. Soc.* 103:3185-3191.
McGee et al. "The Nogo-66 Receptor:Focusing Myelin Inhibition of Axon Regeneration" Apr. 2003, *Trends in Neuroscience* 26(4):193-198 XP004418152.
Michelacci et al. "A Comparative Study Between a Chondroitinase B and a Chondroitinase AC from *Flavobacterium heparinum*" 1975, *Biochem. J.* 151:121-129.
Michelacci et al. "Chondroitinase C from *Flavobacterium haparinum*" 1976, *J. Biol. Chem.* 251(4):1154-1158.
Michelacci et al. "Isolation and characterization of an induced Chondroitinase ABC" 1987, *Biochem. Biophys. Acta* 923:291-301.
Michelacci et al. "Isolation and Partial Characterization of an Induced Chondroitinase β from Flavobacterium Heparium" 1974, *Biochem. & Biophys. Res. Comm.* 56(4):973-980.
Miller et al. "N-terminal methionine-specific peptidase in *Salmonella typhimurium*" 1987, *PNAS* 84:2718-2722.
Miura et al. "Analysis of Glycosaminoglycan-Degrading Enzymes by Substrate Gel Electrophoresis (Zymography)" 1995, *Anal. Biochem.* 225:333-340.

Modena et al. "Hylauronidase-injectable microparticles intended for the treatment of extravasation" 1998, *J. Microencapsulation* 15(1):85-92.
Moon et al. "Regeneration of CNS axons back to their target following treatment of adult rat brain with chondroitinase ABC" 2001, *Nature Neurosc.* 4(5): 465-466.
Moos et al. "Neural adhesion molecule L1 as a member of the immunoglobulin superfamily with binding domains similar to fibronectin" 1988, *Nature* 334:701-703.
Nagahara et al. "Transduction of fUll-length TAT fusion proteins into mammalian cells: TAT_p27Klp1 induces cell migration" 1998, *Nat. Med.* 4(12):1449-1452.
Netti et al. "Role of Extracellular Matrix Assembly in Interstitial Transport in Solid Tumors" 2000, *Cancer Res.* 60(9):2497-2503.
Nieke et al. "Expression of the neural cell adhesion molecules L1 and N-CAM and their common carbohydrate epitope L2/HNK-1 during development and after transaction of the mouse sciatic nerve" 1985, *Differentiation* 30:141-151.
Oermann et al. "The Use of Anti-inflammatory Medications in Cystic Fibrosis" 1999, *Chest* 115:1053-1058.
Olmarker et al. "Chondroitinase ABC (Pharmaceutical Grade) for Chemonucleolysis" 1996, *Spine* 21(17):1952-1956.
Pawson et al. "Assembly of Cell Regulatory systems Through Protein Interaction Domains" 2003, *Science* 300:445-452.
Pillwein et al. "Hyaluronidase Additional to Standard Chemotherapy Improves Outcome for Children with Malignant Tumors" 1998, *Cancer Letters* 131:101-108.
Pojasek et al. "Biochemical Characterization of the Chondroitinase B Active Site" Aug. 23, 2002, *J. Biol. Chem.* 277(34):31179-31186.
Pojasek et al. "Recombinant Expression, Purification, and Kinetic Characterization of Chondroitinase AC and Chondroitinase B from Flavobacterium heparinum" 2001, *Biochem, Biophys. Res. Commun.* 286:343-351.
Prabhakar et al. "Biochemical Characterization of the Chondroitinase ABC I Active Site" Aug. 23, 2005, *Biochem. J.* 390(2):395-405.
Prabhakar et al. "Chondroitinase ABC I From Proteus Vulgaris: Closing, Recombinant Expression and Active Site Identification" Feb. 15, 2005, *Biochem. J.* 386(1):103-112.
Priestley et al. "Stimulating regeneration in the damaged spinal cord" 2002, *J. Phyl.* 96:123-133.
Rathjen et al. "Immunocytological and biochemical characterization of a new neuronal cell surface component (L1 antigen) which is involved in cell adhesion" 1984, *EMBO J.* 3(1):1-10.
Ratjen et al. "Cystic Fibrosis" 2003, The Lancet 361(9358):681-689 (Presentation).
Reich et al. "Small interfering RNA (siRNA) targeting VEGF effectively inhibits ocular neovascularization in a mouse model" 2003, *Molecular Vision* 9:210-216 (Abstract).
Reid et al. "Variants of Human L1 Cell Adhesion Molecule Arise through Alternate Splicing of RNA" 1992, *J. Mol. Neurosc.* 3:127-135.
Roy et al. "Generation of Substantially Smaller Deletion Mutants of Chondroitinase AC and B Those are Biologically Active" Nov. 8-12, 2003, Society for Neuroscience Abstract Viewer and Itinerary Planner, 33$^{rd}$ Annual Meeting of the Society of Neuroscience, New Orleans, LA, Database Biosis, (Abstract).
Roy et al. "Treatment with Recombinant Chondroitinases AC and B Permits Neuronal Outgrowth Over Inhibitory Chondroitin Sulfate Proteoglycans (CSPGs)" Nov. 7, 2002, Society for Neuroscience Abstract Archives 2000-2005 (Abstract).
Saito et al. "Enzymatic Methods for the Determination of Small Quantities of Isomeric Chondroitin Sulfates" 1968, *J. Biol. Chem.* 243(7):1536-1542.
Sambrook et al. "Molecular Cloning" 1989, 2$^{nd}$ ed., Cold Spring Harbor Laboratory Press, Ch. 16 and 17.
Sambrook et al. "Molecular Cloning" 1989, 2$^{nd}$ ed., Cold Spring Harbor Laboratory Press, TOC.
Sato et al. "Cloning and expression in *Escherichia coli* of the gene encoding the Proteus vulgaris chondroitin ABC-lyase" Jan. 1, 1994, *Appl. Microbiol. Biotechnol.* 41:39-46.
Sato, et al. "Subunit Structure of Chondroitinase ABC from Proteus Vulgaris" 1986 *Agric. Biol. Chem.* 50(4):1057-1059.

(56) References Cited

OTHER PUBLICATIONS

Schachner "Functional implications of glial cell recognition molecules" 1990, *Neurosc.* 2:497-507.
Schwab "Nerve fibre regeneration after traumatic lesions of the CNS; progress and problems" 1991, *Phil. Trans. R. Soc. Lond.* 331:303-306.
Schwarze et al. "In Vivo Protein Transduction: Delivery of a Biologically Active Protein into the Mouse" 1999, *Science* 285:1569-1572.
Seikagaku Biobus. Corp. "Chondroitinase AC II pamphlet" 2009, URL: http/www.seikagakubb.co.jp/bio/cgi-bin/search/tenpu_pdf/100335.pdf.
Seilheimer et al. "Studies of Adhesion Molecules Mediating Interactions between Cells of Peripheral Nervous System Indicate a Major Role for L1 in Mediating Sensory Neuron Growth on Schwann Cells in Culture" 1988, *J. Cell Biol.* 107:341-351.
Silver et al. "Postnatally induced formation of the corpus callosum in acallosal mice on glia-coated cellulose bridges" 1983, *Science* 220:1067-1069.
Smiseth et al. "Effect of Hyaluronidase on Substrate Exchange and Blood Flow in the Ischaemic Myocardium of the Dog" 1982, *Clinical Physiology* 2(1):39-50.
Smith-Thomas et al. "Increased Axon Regeneration in Astrocytes Grown in the Presence of Proteoglycan Synthesis Inhibitors" 1995, *J. of Cell Science* 108(3):1307-1315.
Southern "Detection of Specific Sequences Among DNA Fragments Separated by Gel Electrophoresis" 1975, *J. Mol. Biol.* 98:503-517.
Stedman's Medical Dictionary 2000, Lippincott Williams & Wilkins, 27th Ed.
Sterne et al. "Neurotrophin-3 Delivered Locally via Fibronectin Mats Enhances Peripheral Nerve Regeneration" 1997, *Eur. J. Neurosc.* 9:1388-1396.
Tona et al. "Effect of Hyaluronidase on Brain Extracellular Matrix in Vivo and Optic Nerve Regeneration" 1993, *J. Neurosc. Res.* 36:191-199.
Trigg et al. "Peripheral Nerve Regeneration: Comparison of Laminin and Acidic Fibroblast Growth Factor" 1998, *Am. J. Otolaryngology* 19(1):29-32.
Tsuda et al. "Substrate Specificity Studies of Flavobacterium Chondroitinase C and Heparitinases Towards the Glycosaminoglycan-protein Linkage region" 1999, *European J. of Biochem.* 262:127-133.
Vives et al. "A Truncated HIV-1 Tat Protein Basic Domain Rapidly Translocates through the Plasma Membrane and Accumulates in the Cell Nucleus" 1997, *J. Biol. Chem.* 272(25):16010-16017.
Vives et al. "Effects of the Tat Basic Domain on Human Immunodeficiency Virus Type 1 Transactivation, Using Chemically Synthesized Tat Protein and Tat Peptides" May 1994, *J. Virol.* 68(5):3343-3353.

Williams et al. "Calcium Influx into Neurons Can Solely Account for Cell Contact-dependent Neurite Outgrowth Stimulated by Transfected L1" 1992, *J. Cell Biol.* 119(4):883-892.
Wood et al. "Inhibition of Schwann Cell Myelination in vitro by Antibody to the L1 Adhesion Molecule" 1990, *J. Neurosc.* 10(11):3635-3645.
Yamagata et al. "Purification and Properties of Bacterial Chondroitinases and Chondrosulfatases" 1968, *J. Biol. Chem.* 243(7):1523-1535.
Yamagata et al. "Repression of a Malignant Cell-Substratum Adhesion Phenotype by Inhibiting the Production of the Anti-Adhesive Proteoglycan, PG-M/Versican" 1994, *J. of Cell Science* 1007:2581-2590.
Yang et al. "Developmental Regulation of a Matrix Metalloproteinase during Regeneration of Axolotl Appendages" 1994, *Dev. Biol.* 166:696-703.
Yang et al. "Expression of *Mmp-9* and Related Matrix Metalloproteinase Genes During Axolotl Limb Regeneration" 1999, *Dev. Dyn.* 216:2-9.
Yasuda et al. "Effect of Hyluronidase on Experimental Cerebral Infarct Size and Mortality" 1982, *Lab. Invest.* 46(4):400-404.
Yick et al. "Chondroitinase ABC promotes axonal regeneration of Clarke's neurons after spinal cord injury" 2000, *Regeneration and Transpl.* 11(5):1063-1067.
Yick et al. "Chondroitinase ABC Promotes Axonal Regrowth of Clarke's Neurons Into Peripheral Nerve Graft After Hemisection of the Spinal Cord" 1999, Soc. for Neuroscience Abstracts 25:747.
Zuo et al. "Degradation of Chondroitin Sulfate Proteoglycan Enhances the Neurite-Promoting Potential of Spinal Cord Tissue" 1998, *Exp. Neurol.* 154(2):654-662.
Zuo et al. "Regeneration of Axons After Nerve Transection Repair is Enhanced by Degradation of Chondroitin Sulfate Proteoglycan" 2002, *Exp. Neurology* 176:221-228.
Prabhakar et al. "Recombinant Expression, Purification, and Biochemical Characterization of Chondroitinase ABCII from Proteus vulgaris," J. Biol. Chem. (Oct. 10, 2008), 284(2):974-982.
Csoka et al. "Purification and Microsequencing of Hyaluronidase Isozymes from Human Urine" 1997, FEBS Letters 307-310.
Fawcett et al. "Factors Influencing the Regeneration of Axons in the Central Nervous System" 1991, Paraplegia 287-293.
Horner et al. "Regenerating the Damaged Central Nervous System" Oct. 26, 2000, Nature 407:963-970.
Moon et al. "Limited Growth of Severed CNS Axons After Treatment of Adult Rat Brain with Hyaluronidase" 2003, J. Neuroscience Res. 71:23-37.
Schwarze et al. "In Vivo Protein Transduction: Intracellular Delivery of Biologically Active Proteins, Compounds and DNA" Feb. 2000, Trends Pharmcol. Sci. 21:45-58.

\* cited by examiner

SEQUENCE LISTING

<160> NUMBER OF SEQ ID NOS: 14

<210> SEQ ID NO 1
<211> LENGTH: 997
<212> TYPE: PRT
<213> ORGANISM: Artificial
<220> FEATURE:
<223> OTHER INFORMATION: Proteus Vulgaris

<400> SEQUENCE: 1

```
Ala Thr Ser Asn Pro Ala Phe Asp Pro Lys Asn Leu Met Gln Ser Glu
1               5                   10                  15

Ile Tyr His Phe Ala Gln Asn Asn Pro Leu Ala Asp Phe Ser Ser Asp
            20                  25                  30

Lys Asn Ser Ile Leu Thr Leu Ser Asp Lys Arg Ser Ile Met Gly Asn
        35                  40                  45

Gln Ser Leu Leu Trp Lys Trp Lys Gly Gly Ser Ser Phe Thr Leu His
    50                  55                  60

Lys Lys Leu Ile Val Pro Thr Asp Lys Glu Ala Ser Lys Ala Trp Gly
65                  70                  75                  80

Arg Ser Ser Thr Pro Val Phe Ser Phe Trp Leu Tyr Asn Glu Lys Pro
                85                  90                  95

Ile Asp Gly Tyr Leu Thr Ile Asp Phe Gly Glu Lys Leu Ile Ser Thr
            100                 105                 110

Ser Glu Ala Gln Ala Gly Phe Lys Val Lys Leu Asp Phe Thr Gly Trp
        115                 120                 125
```

-continued

Arg Thr Val Gly Val Ser Leu Asn Asn Asp Leu Glu Asn Arg Glu Met
130                 135                 140

Thr Leu Asn Ala Thr Asn Thr Ser Ser Asp Gly Thr Gln Asp Ser Ile
145                 150                 155                 160

Gly Arg Ser Leu Gly Ala Lys Val Asp Ser Ile Arg Phe Lys Ala Pro
                165                 170                 175

Ser Asn Val Ser Gln Gly Glu Ile Tyr Ile Asp Arg Ile Met Phe Ser
                180                 185                 190

Val Asp Asp Ala Arg Tyr Gln Trp Ser Asp Tyr Gln Val Lys Thr Arg
                195                 200                 205

Leu Ser Glu Pro Glu Ile Gln Phe His Asn Val Lys Pro Gln Leu Pro
210                 215                 220

Val Thr Pro Glu Asn Leu Ala Ala Ile Asp Leu Ile Arg Gln Arg Leu
225                 230                 235                 240

Ile Asn Glu Phe Val Gly Gly Glu Lys Glu Thr Asn Leu Ala Leu Lys
                245                 250                 255

Glu Asn Ile Ser Lys Leu Lys Ser Asp Phe Asp Ala Leu Asn Thr His
                260                 265                 270

Thr Leu Ala Asn Gly Gly Thr Gln Gly Arg His Leu Ile Thr Asp Lys
                275                 280                 285

Gln Ile Ile Ile Tyr Gln Pro Glu Asn Leu Asn Ser Gln Asp Lys Gln
290                 295                 300

Leu Phe Asp Asn Tyr Val Ile Leu Gly Asn Tyr Thr Thr Leu Met Phe
305                 310                 315                 320

Asn Ile Ser Arg Ala Tyr Val Leu Glu Lys Asp Pro Thr Gln Lys Ala
                325                 330                 335

Gln Leu Lys Gln Met Tyr Leu Leu Met Thr Lys His Leu Leu Asp Gln
                340                 345                 350

Gly Phe Val Lys Gly Ser Ala Leu Val Thr Thr His His Trp Gly Tyr
                355                 360                 365

Ser Ser Arg Trp Trp Tyr Ile Ser Thr Leu Leu Met Ser Asp Ala Leu
370                 375                 380

Lys Glu Ala Asn Leu Gln Thr Gln Val Tyr Asp Ser Leu Leu Trp Tyr
385                 390                 395                 400

Ser Arg Glu Phe Lys Ser Ser Phe Asp Met Lys Val Ser Ala Asp Ser
                405                 410                 415

Ser Asp Leu Asp Tyr Phe Asn Thr Leu Ser Arg Gln His Leu Ala Leu
                420                 425                 430

Leu Leu Leu Glu Pro Asp Asp Gln Lys Arg Ile Asn Leu Val Asn Thr
435                 440                 445

Phe Ser His Tyr Ile Thr Gly Ala Leu Thr Gln Val Pro Pro Gly Gly
450                 455                 460

Lys Asp Gly Leu Arg Pro Asp Gly Thr Ala Trp Arg His Glu Gly Asn
465                 470                 475                 480

Tyr Pro Gly Tyr Ser Phe Pro Ala Phe Lys Asn Ala Ser Gln Leu Ile
                485                 490                 495

Tyr Leu Leu Arg Asp Thr Pro Phe Ser Val Gly Glu Ser Gly Trp Asn
                500                 505                 510

Ser Leu Lys Lys Ala Met Val Ser Ala Trp Ile Tyr Ser Asn Pro Glu
                515                 520                 525

Val Gly Leu Pro Leu Ala Gly Arg His Pro Leu Asn Ser Pro Ser Leu
530                 535                 540

-continued

Lys Ser Val Ala Gln Gly Tyr Tyr Trp Leu Ala Met Ser Ala Lys Ser
545                 550                 555                 560

Ser Pro Asp Lys Thr Leu Ala Ser Ile Tyr Leu Ala Ile Ser Asp Lys
            565                 570                 575

Thr Gln Asn Glu Ser Thr Ala Ile Phe Gly Glu Thr Ile Thr Pro Ala
        580                 585                 590

Ser Leu Pro Gln Gly Phe Tyr Ala Phe Asn Gly Gly Ala Phe Gly Ile
    595                 600                 605

His Arg Trp Gln Asp Lys Met Val Thr Leu Lys Ala Tyr Asn Thr Asn
610                 615                 620

Val Trp Ser Ser Glu Ile Tyr Asn Lys Asp Asn Arg Tyr Gly Arg Tyr
625                 630                 635                 640

Gln Ser His Gly Val Ala Gln Ile Val Ser Asn Gly Ser Gln Leu Ser
            645                 650                 655

Gln Gly Tyr Gln Gln Glu Gly Trp Asp Trp Asn Arg Met Pro Gly Ala
        660                 665                 670

Thr Thr Ile His Leu Pro Leu Lys Asp Leu Asp Ser Pro Lys Pro His
    675                 680                 685

Thr Leu Met Gln Arg Gly Glu Arg Gly Phe Ser Gly Thr Ser Ser Leu
690                 695                 700

Glu Gly Gln Tyr Gly Met Met Ala Phe Asp Leu Ile Tyr Pro Ala Asn
705                 710                 715                 720

Leu Glu Arg Phe Asp Pro Asn Phe Thr Ala Lys Lys Ser Val Leu Ala
            725                 730                 735

Ala Asp Asn His Leu Ile Phe Ile Gly Ser Asn Ile Asn Ser Ser Asp
        740                 745                 750

Lys Asn Lys Asn Val Glu Thr Thr Leu Phe Gln His Ala Ile Thr Pro
    755                 760                 765

Thr Leu Asn Thr Leu Trp Ile Asn Gly Gln Lys Ile Glu Asn Met Pro
770                 775                 780

Tyr Gln Thr Thr Leu Gln Gln Gly Asp Trp Leu Ile Asp Ser Asn Gly
785                 790                 795                 800

Asn Gly Tyr Leu Ile Thr Gln Ala Glu Lys Val Asn Val Ser Arg Gln
            805                 810                 815

His Gln Val Ser Ala Glu Asn Lys Asn Arg Gln Pro Thr Glu Gly Asn
        820                 825                 830

Phe Ser Ser Ala Trp Ile Asp His Ser Thr Arg Pro Lys Asp Ala Ser
    835                 840                 845

Tyr Glu Tyr Met Val Phe Leu Asp Ala Thr Pro Glu Lys Met Gly Glu
850                 855                 860

Met Ala Gln Lys Phe Arg Glu Asn Asn Gly Leu Tyr Gln Val Leu Arg
865                 870                 875                 880

Lys Asp Lys Asp Val His Ile Ile Leu Asp Lys Leu Ser Asn Val Thr
            885                 890                 895

Gly Tyr Ala Phe Tyr Gln Pro Ala Ser Ile Glu Asp Lys Trp Ile Lys
        900                 905                 910

Lys Val Asn Lys Pro Ala Ile Val Met Thr His Arg Gln Lys Asp Thr
    915                 920                 925

Leu Ile Val Ser Ala Val Thr Pro Asp Leu Asn Met Thr Arg Gln Lys
930                 935                 940

Ala Ala Thr Pro Val Thr Ile Asn Val Thr Ile Asn Gly Lys Trp Gln
945                 950                 955                 960

Ser Ala Asp Lys Asn Ser Glu Val Lys Tyr Gln Val Ser Gly Asp Asn

```
                   965                 970                 975
Thr Glu Leu Thr Phe Thr Ser Tyr Phe Gly Ile Pro Gln Glu Ile Lys
            980                 985                 990
Leu Ser Pro Leu Pro
        995

<210> SEQ ID NO 2
<211> LENGTH: 997
<212> TYPE: PRT
<213> ORGANISM: Artificial
<220> FEATURE:
<223> OTHER INFORMATION: Proteus vulgaris

<400> SEQUENCE: 2

Ala Thr Ser Asn Pro Ala Phe Asp Pro Lys Asn Leu Met Gln Ser Glu
1               5                  10                  15

Ile Tyr His Phe Ala Gln Asn Asn Pro Leu Ala Asp Phe Ser Ser Asp
            20                  25                  30

Lys Asn Ser Ile Leu Thr Leu Ser Asp Lys Arg Ser Ile Met Gly Asn
        35                  40                  45

Gln Ser Leu Leu Trp Lys Trp Lys Gly Gly Ser Ser Phe Thr Leu His
    50                  55                  60

Lys Lys Leu Ile Val Pro Thr Asp Lys Glu Ala Ser Lys Ala Trp Gly
65                  70                  75                  80

Arg Ser Ser Thr Pro Val Phe Ser Phe Trp Leu Tyr Asn Glu Lys Pro
                85                  90                  95

Ile Asp Gly Tyr Leu Thr Ile Ala Phe Gly Glu Lys Leu Ile Ser Thr
            100                 105                 110

Ser Glu Ala Gln Ala Gly Phe Lys Val Lys Leu Asp Phe Thr Gly Trp
        115                 120                 125

Arg Thr Val Gly Val Ser Leu Asn Asn Asp Leu Glu Asn Arg Glu Met
    130                 135                 140

Thr Leu Asn Ala Thr Asn Thr Ser Ser Asp Gly Thr Gln Asp Ser Ile
145                 150                 155                 160

Gly Arg Ser Leu Gly Ala Lys Val Asp Ser Ile Arg Phe Lys Ala Pro
                165                 170                 175

Ser Asn Val Ser Gln Gly Glu Ile Tyr Ile Asp Arg Ile Met Phe Ser
            180                 185                 190

Val Asp Asp Ala Arg Tyr Gln Trp Ser Asp Tyr Gln Val Lys Thr Arg
        195                 200                 205

Leu Ser Glu Pro Glu Ile Gln Phe His Asn Val Lys Pro Gln Leu Pro
    210                 215                 220

Val Thr Pro Glu Asn Leu Ala Ala Ile Asp Leu Ile Arg Gln Arg Leu
225                 230                 235                 240

Ile Asn Glu Phe Val Gly Gly Glu Lys Glu Thr Asn Leu Ala Leu Glu
                245                 250                 255

Glu Asn Ile Ser Lys Leu Lys Ser Asp Phe Asp Ala Leu Asn Thr His
            260                 265                 270

Thr Leu Ala Asn Gly Gly Thr Gln Gly Arg His Leu Ile Thr Asp Lys
        275                 280                 285

Gln Ile Ile Tyr Gln Pro Glu Asn Leu Asn Ser Gln Asp Lys Gln
    290                 295                 300

Leu Phe Asp Asn Tyr Val Ile Leu Gly Asn Tyr Thr Thr Leu Met Phe
305                 310                 315                 320

Asn Ile Ser Arg Ala Tyr Val Leu Glu Lys Asp Pro Thr Gln Lys Ala
```

-continued

```
            325                 330                 335
Gln Leu Lys Gln Met Tyr Leu Met Thr Lys His Leu Leu Asp Gln
            340                 345                 350

Gly Phe Val Lys Gly Ser Ala Leu Val Thr His Trp Gly Tyr
            355                 360             365

Ser Ser Arg Trp Trp Tyr Ile Ser Thr Leu Leu Met Ser Asp Ala Leu
    370                 375                 380

Lys Glu Ala Asn Leu Gln Thr Gln Val Tyr Asp Ser Leu Leu Trp Tyr
385                 390                 395                 400

Ser Arg Glu Phe Lys Ser Ser Phe Asp Met Lys Val Ser Ala Asp Ser
                405                 410                 415

Ser Asp Leu Asp Tyr Phe Asn Thr Leu Ser Arg Gln His Leu Ala Leu
            420                 425                 430

Leu Leu Leu Glu Pro Asp Asp Gln Lys Arg Ile Asn Leu Val Asn Thr
            435                 440                 445

Phe Ser His Tyr Ile Thr Gly Ala Leu Thr Gln Val Pro Pro Gly Gly
        450                 455                 460

Lys Asp Gly Leu Arg Pro Asp Gly Thr Ala Trp Arg His Glu Gly Asn
465                 470                 475                 480

Tyr Pro Gly Tyr Ser Phe Pro Ala Phe Lys Asn Ala Ser Gln Leu Ile
                485                 490                 495

Tyr Leu Leu Arg Asp Thr Pro Phe Ser Val Gly Glu Ser Gly Trp Asn
            500                 505                 510

Ser Leu Lys Lys Ala Met Val Ser Ala Trp Ile Tyr Ser Asn Pro Glu
        515                 520                 525

Val Gly Leu Pro Leu Ala Gly Arg His Pro Leu Asn Ser Pro Ser Leu
    530                 535                 540

Lys Ser Val Ala Gln Gly Tyr Tyr Trp Leu Ala Met Ser Ala Lys Ser
545                 550                 555                 560

Ser Pro Asp Lys Thr Leu Ala Ser Ile Tyr Leu Ala Ile Ser Asp Lys
                565                 570                 575

Thr Gln Asn Glu Ser Thr Ala Ile Phe Gly Glu Thr Ile Thr Pro Ala
            580                 585                 590

Ser Leu Pro Gln Gly Phe Tyr Ala Phe Asn Gly Gly Ala Phe Gly Ile
        595                 600                 605

His Arg Trp Gln Asp Lys Met Val Thr Leu Lys Ala Tyr Asn Thr Asn
            610                 615                 620

Val Trp Ser Ser Glu Ile Tyr Asn Lys Asp Asn Arg Tyr Gly Arg Tyr
625                 630                 635                 640

Gln Ser His Gly Val Ala Gln Ile Val Ser Asn Gly Ser Gln Leu Ser
                645                 650                 655

Gln Gly Tyr Gln Gln Glu Gly Trp Asp Trp Asn Arg Met Pro Gly Ala
            660                 665                 670

Thr Thr Ile His Leu Pro Leu Lys Asp Leu Asn Ser Pro Lys Pro His
        675                 680                 685

Thr Leu Met Gln Arg Gly Glu Arg Gly Phe Ser Gly Thr Ser Ser Leu
    690                 695                 700

Glu Gly Gln Tyr Gly Met Met Ala Phe Asp Leu Ile Tyr Pro Ala Asn
705                 710                 715                 720

Leu Glu Arg Phe Asp Pro Asn Phe Thr Ala Lys Lys Ser Val Leu Ala
                725                 730                 735

Ala Asp Asn His Leu Ile Phe Ile Gly Ser Asn Ile Asn Ser Ser Asp
            740                 745                 750
```

-continued

```
Lys Asn Lys Asn Val Glu Thr Leu Phe Gln His Ala Ile Thr Pro
            755                 760                 765
Thr Leu Asn Thr Leu Trp Ile Asn Gly Gln Lys Ile Glu Asn Met Pro
        770                 775                 780
Tyr Gln Thr Thr Leu Gln Gln Gly Asp Trp Leu Ile Asp Ser Asn Gly
785                 790                 795                 800
Asn Gly Tyr Leu Ile Thr Gln Ala Glu Lys Val Asn Val Ser Arg Gln
                805                 810                 815
His Gln Val Ser Ala Glu Asn Lys Asn Arg Gln Pro Thr Glu Gly Asn
            820                 825                 830
Phe Ser Ser Ala Trp Ile Asp His Ser Thr Arg Pro Lys Asp Ala Ser
        835                 840                 845
Tyr Glu Tyr Met Val Phe Leu Asp Ala Thr Pro Glu Lys Met Gly Glu
850                 855                 860
Met Ala Gln Lys Phe Arg Glu Asn Asn Gly Leu Tyr Gln Val Leu Arg
865                 870                 875                 880
Lys Asp Lys Asp Val His Ile Ile Leu Asp Lys Leu Ser Asn Val Thr
                885                 890                 895
Gly Tyr Ala Phe Tyr Gln Pro Ala Ser Ile Glu Asp Lys Trp Ile Lys
            900                 905                 910
Lys Val Asn Lys Pro Ala Ile Val Met Thr His Arg Gln Lys Asp Thr
        915                 920                 925
Leu Ile Val Ser Ala Val Thr Pro Asp Leu Asn Met Thr Arg Gln Lys
930                 935                 940
Ala Ala Thr Pro Val Thr Ile Asn Val Thr Ile Asn Gly Lys Trp Gln
945                 950                 955                 960
Ser Ala Asp Lys Asn Ser Glu Val Lys Tyr Gln Val Ser Gly Asp Asn
                965                 970                 975
Thr Glu Leu Thr Phe Thr Ser Tyr Phe Gly Ile Pro Gln Glu Ile Lys
            980                 985                 990
Leu Ser Pro Leu Pro
        995

<210> SEQ ID NO 3
<211> LENGTH: 997
<212> TYPE: PRT
<213> ORGANISM: Artificial
<220> FEATURE:
<223> OTHER INFORMATION: Proteus Vulgaris

<400> SEQUENCE: 3

Ala Thr Ser Asn Pro Ala Phe Asp Pro Lys Asn Leu Met Gln Ser Glu
1               5                   10                  15
Ile Tyr His Phe Ala Gln Asn Asn Pro Leu Ala Asp Phe Ser Ser Asp
            20                  25                  30
Lys Asn Ser Ile Leu Thr Leu Ser Asp Lys Arg Ser Ile Met Gly Asn
        35                  40                  45
Gln Ser Leu Leu Trp Lys Trp Lys Gly Gly Ser Ser Phe Thr Leu His
    50                  55                  60
Lys Lys Leu Ile Val Pro Thr Asp Lys Glu Ala Ser Lys Ala Trp Gly
65                  70                  75                  80
Arg Ser Ser Thr Pro Val Phe Ser Phe Trp Leu Tyr Asn Glu Lys Pro
                85                  90                  95
Ile Asp Gly Tyr Leu Thr Ile Asp Phe Gly Glu Lys Leu Ile Ser Thr
            100                 105                 110
```

```
Ser Glu Ala Gln Ala Gly Phe Lys Val Lys Leu Asp Phe Thr Gly Trp
        115                 120                 125
Arg Thr Val Gly Val Ser Leu Asn Asn Asp Leu Glu Asn Arg Glu Met
    130                 135                 140
Thr Leu Asn Ala Thr Asn Thr Ser Ser Asp Gly Thr Gln Asp Ser Ile
145                 150                 155                 160
Gly Arg Ser Leu Gly Ala Lys Val Asp Ser Ile Arg Phe Lys Ala Pro
                165                 170                 175
Ser Asn Val Ser Gln Gly Glu Ile Tyr Ile Asp Arg Ile Met Phe Ser
            180                 185                 190
Val Asp Asp Ala Arg Tyr Gln Trp Ser Asp Tyr Gln Val Lys Thr Arg
        195                 200                 205
Leu Ser Glu Pro Glu Ile Gln Phe His Asn Val Lys Pro Gln Leu Pro
    210                 215                 220
Val Thr Pro Glu Asn Leu Ala Ala Ile Asp Leu Ile Arg Gln Arg Leu
225                 230                 235                 240
Ile Asn Glu Phe Val Gly Gly Glu Lys Glu Thr Asn Leu Ala Leu Glu
                245                 250                 255
Glu Asn Ile Ser Lys Leu Lys Ser Asp Phe Asp Ala Leu Asn Thr His
            260                 265                 270
Thr Leu Ala Asn Gly Gly Thr Gln Gly Arg His Leu Ile Thr Asp Lys
        275                 280                 285
Gln Ile Ile Ile Tyr Gln Pro Glu Asn Leu Asn Ser Gln Asp Lys Gln
    290                 295                 300
Leu Phe Asp Asn Tyr Val Ile Leu Gly Asn Tyr Thr Thr Leu Met Phe
305                 310                 315                 320
Asn Ile Ser Arg Ala Tyr Val Leu Glu Lys Asp Pro Thr Gln Lys Ala
                325                 330                 335
Gln Leu Lys Gln Met Tyr Leu Leu Met Thr Lys His Leu Leu Asp Gln
            340                 345                 350
Gly Phe Val Lys Gly Ser Ala Leu Val Thr Thr His His Trp Gly Tyr
        355                 360                 365
Ser Ser Arg Trp Trp Tyr Ile Ser Thr Leu Leu Met Ser Asp Ala Leu
    370                 375                 380
Lys Glu Ala Asn Leu Gln Thr Gln Val Tyr Asp Ser Leu Leu Trp Tyr
385                 390                 395                 400
Ser Arg Glu Phe Lys Ser Ser Phe Asp Met Lys Val Ser Ala Asp Ser
                405                 410                 415
Ser Asp Leu Asp Tyr Phe Asn Thr Leu Ser Arg Gln His Leu Ala Leu
            420                 425                 430
Leu Leu Leu Glu Pro Asp Asp Gln Lys Arg Ile Asn Leu Val Asn Thr
        435                 440                 445
Phe Ser His Tyr Ile Thr Gly Ala Leu Thr Gln Val Pro Pro Gly Gly
    450                 455                 460
Lys Asp Gly Leu Arg Pro Asp Gly Thr Ala Trp Arg His Glu Gly Asn
465                 470                 475                 480
Tyr Pro Gly Tyr Ser Phe Pro Ala Phe Lys Asn Ala Ser Gln Leu Ile
                485                 490                 495
Tyr Leu Leu Arg Asp Thr Pro Phe Ser Val Gly Glu Ser Gly Trp Asn
            500                 505                 510
Ser Leu Lys Lys Ala Met Val Ser Ala Trp Ile Tyr Ser Asn Pro Glu
        515                 520                 525
```

```
Val Gly Leu Pro Leu Ala Gly Arg His Pro Leu Asn Ser Pro Ser Leu
    530                 535                 540

Lys Ser Val Ala Gln Gly Tyr Tyr Trp Leu Ala Met Ser Ala Lys Ser
545                 550                 555                 560

Ser Pro Asp Lys Thr Leu Ala Ser Ile Tyr Leu Ala Ile Ser Asp Lys
                565                 570                 575

Thr Gln Asn Glu Ser Thr Ala Ile Phe Gly Glu Thr Ile Thr Pro Ala
                580                 585                 590

Ser Leu Pro Gln Gly Phe Tyr Ala Phe Asn Gly Ala Phe Gly Ile
            595                 600                 605

His Arg Trp Gln Asp Lys Met Val Thr Leu Lys Ala Tyr Asn Thr Asn
    610                 615                 620

Val Trp Ser Ser Glu Ile Tyr Asn Lys Asp Asn Arg Tyr Gly Arg Tyr
625                 630                 635                 640

Gln Ser His Gly Val Ala Gln Ile Val Ser Asn Gly Ser Gln Leu Ser
                645                 650                 655

Gln Gly Tyr Gln Gln Glu Gly Trp Asp Trp Asn Arg Met Pro Gly Ala
            660                 665                 670

Thr Thr Ile His Leu Pro Leu Lys Asp Leu Asp Ser Pro Lys Pro His
        675                 680                 685

Thr Leu Met Gln Arg Gly Glu Arg Gly Phe Ser Gly Thr Ser Ser Leu
    690                 695                 700

Glu Gly Gln Tyr Gly Met Met Ala Phe Asp Leu Ile Tyr Pro Ala Asn
705                 710                 715                 720

Leu Glu Arg Phe Asp Pro Asn Phe Thr Ala Lys Lys Ser Val Leu Ala
                725                 730                 735

Ala Asp Asn His Leu Ile Phe Ile Gly Ser Asn Ile Asn Ser Ser Asp
            740                 745                 750

Lys Asn Lys Asn Val Glu Thr Thr Leu Phe Gln His Ala Ile Thr Pro
        755                 760                 765

Thr Leu Asn Thr Leu Trp Ile Asn Gly Gln Lys Ile Glu Asn Met Pro
    770                 775                 780

Tyr Gln Thr Thr Leu Gln Gln Gly Asp Trp Leu Ile Asp Ser Asn Gly
785                 790                 795                 800

Asn Gly Tyr Leu Ile Thr Gln Ala Glu Lys Val Asn Val Ser Arg Gln
                805                 810                 815

His Gln Val Ser Ala Glu Asn Lys Asn Arg Gln Pro Thr Glu Gly Asn
            820                 825                 830

Phe Ser Ser Ala Trp Ile Asp His Ser Thr Arg Pro Lys Asp Ala Ser
        835                 840                 845

Tyr Glu Tyr Met Val Phe Leu Asp Ala Thr Pro Glu Lys Met Gly Glu
    850                 855                 860

Met Ala Gln Lys Phe Arg Glu Asn Asn Gly Leu Tyr Gln Val Leu Arg
865                 870                 875                 880

Lys Asp Lys Asp Val His Ile Ile Leu Asp Lys Leu Ser Asn Val Thr
                885                 890                 895

Gly Tyr Ala Phe Tyr Gln Pro Ala Ser Ile Glu Asp Lys Trp Ile Lys
            900                 905                 910

Lys Val Asn Lys Pro Ala Ile Val Met Thr His Arg Gln Lys Asp Thr
        915                 920                 925

Leu Ile Val Ser Ala Val Thr Pro Asp Leu Asn Met Thr Arg Gln Lys
    930                 935                 940

Ala Ala Thr Pro Val Thr Ile Asn Val Thr Ile Asn Gly Lys Trp Gln
```

```
                    945                 950                 955                 960
Ser Ala Asp Lys Asn Ser Glu Val Lys Tyr Gln Val Ser Gly Asp Asn
                965                 970                 975

Thr Glu Leu Thr Phe Thr Ser Tyr Phe Gly Ile Pro Gln Glu Ile Lys
            980                 985                 990

Leu Ser Pro Leu Pro
        995

<210> SEQ ID NO 4
<211> LENGTH: 997
<212> TYPE: PRT
<213> ORGANISM: Artificial
<220> FEATURE:
<223> OTHER INFORMATION: Proteus Vulgaris

<400> SEQUENCE: 4

Ala Thr Ser Asn Pro Ala Phe Asp Pro Lys Asn Leu Met Gln Ser Glu
1               5                   10                  15

Ile Tyr His Phe Ala Gln Asn Asn Pro Leu Ala Asp Phe Ser Ser Asp
            20                  25                  30

Lys Asn Ser Ile Leu Thr Leu Ser Asp Lys Arg Ser Ile Met Gly Asn
        35                  40                  45

Gln Ser Leu Leu Trp Lys Trp Lys Gly Gly Ser Ser Phe Thr Leu His
    50                  55                  60

Lys Lys Leu Ile Val Pro Thr Asp Lys Glu Ala Ser Lys Ala Trp Gly
65                  70                  75                  80

Arg Ser Ser Thr Pro Val Phe Ser Phe Trp Leu Tyr Asn Glu Lys Pro
                85                  90                  95

Ile Asp Gly Tyr Leu Thr Ile Asp Phe Gly Glu Lys Leu Ile Ser Thr
            100                 105                 110

Ser Glu Ala Gln Ala Gly Phe Lys Val Lys Leu Asp Phe Thr Gly Trp
        115                 120                 125

Arg Thr Val Gly Val Ser Leu Asn Asn Asp Leu Glu Asn Arg Glu Met
    130                 135                 140

Thr Leu Asn Ala Thr Asn Thr Ser Ser Asp Gly Thr Gln Asp Ser Ile
145                 150                 155                 160

Gly Arg Ser Leu Gly Ala Lys Val Asp Ser Ile Arg Phe Lys Ala Pro
                165                 170                 175

Ser Asn Val Ser Gln Gly Glu Ile Tyr Ile Asp Arg Ile Met Phe Ser
            180                 185                 190

Val Asp Asp Ala Arg Tyr Gln Trp Ser Asp Tyr Gln Val Lys Thr Arg
        195                 200                 205

Leu Ser Glu Pro Glu Ile Gln Phe His Asn Val Lys Pro Gln Leu Pro
    210                 215                 220

Val Thr Pro Glu Asn Leu Ala Ala Ile Asp Leu Ile Arg Gln Arg Leu
225                 230                 235                 240

Ile Asn Glu Phe Val Gly Gly Glu Lys Glu Thr Asn Leu Ala Leu Glu
                245                 250                 255

Glu Asn Ile Ser Lys Leu Lys Ser Asp Phe Asp Ala Leu Asn Thr His
            260                 265                 270

Thr Leu Ala Asn Gly Gly Thr Gln Gly Arg His Leu Ile Thr Asp Lys
        275                 280                 285

Gln Ile Ile Ile Tyr Gln Pro Glu Asn Leu Asn Ser Gln Asp Lys Gln
    290                 295                 300

Leu Phe Asp Asn Tyr Val Ile Leu Gly Asn Tyr Thr Thr Leu Met Phe
```

```
                305                 310                 315                 320
        Asn Ile Ser Arg Ala Tyr Val Leu Glu Lys Asp Pro Thr Gln Lys Ala
                        325                 330                 335
        Gln Leu Lys Gln Met Tyr Leu Leu Met Thr Lys His Leu Leu Asp Gln
                        340                 345                 350
        Gly Phe Val Lys Gly Ser Ala Leu Val Thr Thr His Trp Gly Tyr
                        355                 360                 365
        Ser Ser Arg Trp Trp Tyr Ile Ser Thr Leu Leu Met Ser Asp Ala Leu
                370                 375                 380
        Lys Glu Ala Asn Leu Gln Thr Gln Val Tyr Asp Ser Leu Leu Trp Tyr
        385                 390                 395                 400
        Ser Arg Glu Phe Lys Ser Ser Phe Asp Met Lys Val Ser Ala Asp Ser
                        405                 410                 415
        Ser Asp Leu Asp Tyr Phe Asn Thr Leu Ser Arg Gln His Leu Ala Leu
                        420                 425                 430
        Leu Leu Leu Glu Pro Asp Asp Gln Lys Arg Ile Asn Leu Val Asn Thr
                        435                 440                 445
        Phe Ser His Tyr Ile Thr Gly Ala Leu Thr Gln Val Pro Pro Gly Gly
                        450                 455                 460
        Lys Asp Gly Leu Arg Pro Asp Gly Thr Ala Trp Arg His Glu Gly Asn
        465                 470                 475                 480
        Tyr Pro Gly Tyr Ser Phe Pro Ala Phe Lys Asn Ala Ser Gln Leu Ile
                        485                 490                 495
        Tyr Leu Leu Arg Asp Thr Pro Phe Ser Val Gly Glu Ser Gly Trp Asn
                        500                 505                 510
        Ser Leu Lys Lys Ala Met Val Ser Ala Trp Ile Tyr Ser Asn Pro Glu
                        515                 520                 525
        Val Gly Leu Pro Leu Ala Gly Arg His Pro Leu Asn Ser Pro Ser Leu
                        530                 535                 540
        Lys Ser Val Ala Gln Gly Tyr Tyr Trp Leu Ala Met Ser Ala Lys Ser
        545                 550                 555                 560
        Ser Pro Asp Lys Thr Leu Ala Ser Ile Tyr Leu Ala Ile Ser Asp Lys
                        565                 570                 575
        Thr Gln Asn Glu Ser Thr Ala Ile Phe Gly Glu Thr Ile Thr Pro Ala
                        580                 585                 590
        Ser Leu Pro Gln Gly Phe Tyr Ala Phe Asn Gly Gly Ala Phe Gly Ile
                        595                 600                 605
        His Arg Trp Gln Asp Lys Met Val Thr Leu Lys Ala Tyr Asn Thr Asn
                        610                 615                 620
        Val Trp Ser Ser Glu Ile Tyr Asn Lys Asp Asn Arg Tyr Gly Arg Tyr
        625                 630                 635                 640
        Gln Ser His Gly Val Ala Gln Ile Val Ser Asn Gly Ser Gln Leu Ser
                        645                 650                 655
        Gln Gly Tyr Gln Gln Glu Gly Trp Asp Trp Asn Arg Met Pro Gly Ala
                        660                 665                 670
        Thr Thr Ile His Leu Pro Leu Lys Asp Leu Asp Ser Pro Lys Pro His
                        675                 680                 685
        Thr Leu Met Gln Arg Gly Glu Arg Gly Phe Ser Gly Thr Ser Ser Leu
                        690                 695                 700
        Glu Gly Gln Tyr Gly Met Met Ala Phe Asp Leu Ile Tyr Pro Ala Asn
        705                 710                 715                 720
        Leu Glu Arg Phe Asp Pro Asn Phe Thr Ala Lys Lys Ser Val Leu Ala
                        725                 730                 735
```

```
Ala Asp Asn His Leu Ile Phe Ile Gly Ser Asn Ile Asn Ser Ser Asp
            740                 745                 750

Lys Asn Lys Asn Val Glu Thr Thr Leu Phe Gln His Ala Ile Thr Pro
            755                 760                 765

Thr Leu Asn Thr Leu Trp Ile Asn Gly Gln Lys Ile Glu Asn Met Pro
        770                 775                 780

Tyr Gln Thr Thr Leu Gln Gln Gly Asp Trp Leu Ile Asp Ser Asn Gly
785                 790                 795                 800

Asn Gly Tyr Leu Ile Thr Gln Ala Glu Lys Val Asn Val Ser Arg Gln
                805                 810                 815

His Gln Val Ser Ala Glu Asn Lys Asn Arg Gln Pro Thr Glu Gly Asn
            820                 825                 830

Phe Ser Ser Ala Trp Ile Asp His Ser Thr Arg Pro Lys Asp Ala Ser
            835                 840                 845

Tyr Glu Tyr Met Val Phe Leu Asp Ala Thr Pro Glu Lys Met Gly Glu
        850                 855                 860

Met Ala Gln Lys Phe Arg Glu Asn Asn Gly Leu Tyr Gln Val Leu Arg
865                 870                 875                 880

Lys Asp Lys Asp Val His Ile Ile Leu Asp Lys Leu Ser Asn Val Thr
                885                 890                 895

Gly Tyr Ala Phe Tyr Gln Pro Ala Ser Ile Glu Asp Lys Trp Ile Lys
            900                 905                 910

Lys Val Asn Lys Pro Ala Ile Val Met Thr His Arg Gln Lys Asp Thr
            915                 920                 925

Leu Ile Val Ser Ala Val Thr Pro Asp Leu Asn Met Thr Arg Gln Lys
        930                 935                 940

Ala Ala Thr Pro Val Thr Ile Asn Val Thr Ile Asn Gly Lys Trp Gln
945                 950                 955                 960

Ser Ala Asp Lys Asn Ser Glu Val Lys Tyr Gln Val Ser Gly Asp Asn
                965                 970                 975

Thr Glu Leu Thr Phe Thr Ser Tyr Phe Gly Ile Pro Gln Glu Ile Lys
            980                 985                 990

Leu Ser Pro Leu Pro
            995

<210> SEQ ID NO 5
<211> LENGTH: 997
<212> TYPE: PRT
<213> ORGANISM: Artificial
<220> FEATURE:
<223> OTHER INFORMATION: Proteus Vulgaris

<400> SEQUENCE: 5

Ala Thr Ser Asn Pro Ala Phe Asp Pro Lys Asn Leu Met Gln Ser Glu
1               5                   10                  15

Ile Tyr His Phe Ala Gln Asn Asn Pro Leu Ala Asp Phe Ser Ser Asp
            20                  25                  30

Lys Asn Ser Ile Leu Thr Leu Ser Asp Lys Arg Ser Ile Met Gly Asn
        35                  40                  45

Gln Ser Leu Leu Trp Lys Trp Lys Gly Gly Ser Ser Phe Thr Leu His
    50                  55                  60

Lys Lys Leu Ile Val Pro Thr Asp Lys Glu Ala Ser Lys Ala Trp Gly
65                  70                  75                  80

Arg Ser Ser Thr Pro Val Phe Ser Phe Trp Leu Tyr Asn Glu Lys Pro
                85                  90                  95
```

```
Ile Asp Gly Tyr Leu Thr Ile Asp Phe Gly Glu Lys Leu Ile Ser Thr
            100                 105                 110

Ser Glu Ala Gln Ala Gly Phe Lys Val Lys Leu Asp Phe Thr Gly Trp
            115                 120                 125

Arg Thr Val Gly Val Ser Leu Asn Asn Asp Leu Glu Asn Arg Glu Met
            130                 135                 140

Thr Leu Asn Ala Thr Asn Thr Ser Ser Asp Gly Thr Gln Asp Ser Ile
145                 150                 155                 160

Gly Arg Ser Leu Gly Ala Lys Val Asp Ser Ile Arg Phe Lys Ala Pro
                165                 170                 175

Ser Asn Val Ser Gln Gly Glu Ile Tyr Ile Asp Arg Ile Met Phe Ser
            180                 185                 190

Val Asp Asp Ala Arg Tyr Gln Trp Ser Asp Tyr Gln Val Lys Thr Arg
            195                 200                 205

Leu Ser Glu Pro Glu Ile Gln Phe His Asn Val Lys Pro Gln Leu Pro
            210                 215                 220

Val Thr Pro Glu Asn Leu Ala Ala Ile Asp Leu Ile Arg Gln Arg Leu
225                 230                 235                 240

Ile Asn Glu Phe Val Gly Gly Glu Lys Glu Thr Asn Leu Ala Leu Glu
                245                 250                 255

Glu Asn Ile Ser Lys Leu Lys Ser Asp Phe Asp Ala Leu Asn Thr His
            260                 265                 270

Thr Leu Ala Asn Gly Gly Thr Gln Gly Arg His Leu Ile Thr Asp Lys
            275                 280                 285

Gln Ile Ile Ile Tyr Gln Pro Glu Asn Leu Asn Ser Gln Asp Lys Gln
            290                 295                 300

Leu Phe Asp Asn Tyr Val Ile Leu Gly Asn Tyr Thr Thr Leu Met Phe
305                 310                 315                 320

Asn Ile Ser Arg Ala Tyr Val Leu Glu Lys Asp Pro Thr Gln Lys Ala
                325                 330                 335

Gln Leu Lys Gln Met Tyr Leu Leu Met Thr Lys His Leu Leu Asp Gln
            340                 345                 350

Gly Phe Val Lys Gly Ser Ala Leu Val Thr Thr His His Trp Gly Tyr
            355                 360                 365

Ser Ser Arg Trp Trp Tyr Ile Ser Thr Leu Leu Met Ser Asp Ala Leu
370                 375                 380

Lys Glu Ala Asn Leu Gln Thr Gln Val Tyr Asp Ser Leu Leu Trp Tyr
385                 390                 395                 400

Ser Arg Glu Phe Lys Ser Ser Phe Asp Met Lys Val Ser Ala Asp Ser
                405                 410                 415

Ser Asp Leu Asp Tyr Phe Asn Thr Leu Ser Arg Gln His Leu Ala Leu
            420                 425                 430

Leu Leu Leu Glu Pro Asp Asp Gln Lys Arg Ile Asn Leu Val Asn Thr
            435                 440                 445

Phe Ser His Tyr Ile Thr Gly Ala Leu Thr Gln Val Pro Pro Gly Gly
            450                 455                 460

Lys Asp Gly Leu Arg Pro Asp Gly Thr Ala Trp Arg His Glu Gly Asn
465                 470                 475                 480

Tyr Pro Gly Tyr Ser Phe Pro Ala Phe Lys Asn Ala Ser Gln Leu Ile
                485                 490                 495

Tyr Leu Leu Arg Asp Thr Pro Phe Ser Val Gly Glu Ser Gly Trp Asn
            500                 505                 510
```

-continued

Ser Leu Lys Lys Ala Met Val Ser Ala Trp Ile Tyr Ser Asn Pro Glu
    515                 520                 525

Val Gly Leu Pro Leu Ala Gly Arg His Pro Leu Asn Ser Pro Ser Leu
530                 535                 540

Lys Ser Val Ala Gln Gly Tyr Tyr Trp Leu Ala Met Ser Ala Lys Ser
545                 550                 555                 560

Ser Pro Asp Lys Thr Leu Ala Ser Ile Tyr Leu Ala Ile Ser Asp Lys
                565                 570                 575

Thr Gln Asn Glu Ser Thr Ala Ile Phe Gly Thr Ile Thr Pro Ala
            580                 585                 590

Ser Leu Pro Gln Gly Phe Tyr Ala Phe Asn Gly Gly Ala Phe Gly Ile
        595                 600                 605

His Arg Trp Gln Asp Lys Met Val Thr Leu Lys Ala Tyr Asn Thr Asn
    610                 615                 620

Val Trp Ser Ser Glu Ile Tyr Asn Lys Asp Asn Arg Tyr Gly Arg Tyr
625                 630                 635                 640

Gln Ser His Gly Val Ala Gln Ile Val Ser Asn Gly Ser Gln Leu Ser
                645                 650                 655

Gln Gly Tyr Gln Gln Glu Gly Trp Asp Trp Asn Arg Met Pro Gly Ala
            660                 665                 670

Thr Thr Ile His Leu Pro Leu Lys Asp Leu Asp Ser Pro Lys Pro His
        675                 680                 685

Thr Leu Met Gln Arg Gly Glu Arg Gly Phe Ser Gly Thr Ser Ser Leu
    690                 695                 700

Glu Gly Gln Tyr Gly Met Met Ala Phe Asp Leu Ile Tyr Pro Ala Asn
705                 710                 715                 720

Leu Glu Arg Phe Asp Pro Asn Phe Thr Ala Lys Lys Ser Val Leu Pro
                725                 730                 735

Ala Asp Asn His Leu Ile Phe Ile Gly Ser Asn Ile Asn Ser Ser Asp
            740                 745                 750

Lys Asn Lys Asn Val Glu Thr Thr Leu Phe Gln His Ala Ile Thr Pro
        755                 760                 765

Thr Leu Asn Thr Leu Trp Ile Asn Gly Gln Lys Ile Glu Asn Met Pro
    770                 775                 780

Tyr Gln Thr Thr Leu Gln Gln Gly Asp Trp Leu Ile Asp Ser Asn Gly
785                 790                 795                 800

Asn Gly Tyr Leu Ile Thr Gln Ala Glu Lys Val Asn Val Ser Arg Gln
                805                 810                 815

His Gln Val Ser Ala Glu Asn Lys Asn Arg Gln Pro Thr Glu Gly Asn
            820                 825                 830

Phe Ser Ser Ala Trp Ile Asp His Ser Thr Arg Pro Lys Asp Ala Ser
        835                 840                 845

Tyr Glu Tyr Met Val Phe Leu Asp Ala Thr Pro Glu Lys Met Gly Glu
    850                 855                 860

Met Ala Gln Lys Phe Arg Glu Asn Asn Gly Leu Tyr Gln Val Leu Arg
865                 870                 875                 880

Lys Asp Lys Asp Val His Ile Ile Leu Asp Lys Leu Ser Asn Val Thr
                885                 890                 895

Gly Tyr Ala Phe Tyr Gln Pro Ala Ser Ile Glu Asp Lys Trp Ile Lys
            900                 905                 910

Lys Val Asn Lys Pro Ala Phe Val Met Thr His Arg Gln Lys Asp Thr
        915                 920                 925

Leu Ile Val Ser Ala Val Thr Pro Asp Leu Asn Met Thr Arg Gln Lys

```
                930             935             940
Ala Ala Thr Pro Val Thr Ile Asn Val Thr Ile Asn Gly Lys Trp Gln
945                 950                 955                 960

Ser Ala Asp Lys Asn Ser Glu Val Lys Tyr Gln Val Ser Gly Asp Asn
            965                 970                 975

Thr Glu Leu Thr Phe Thr Ser Tyr Phe Gly Ile Pro Gln Glu Ile Lys
                980                 985                 990

Leu Ser Pro Leu Pro
        995

<210> SEQ ID NO 6
<211> LENGTH: 997
<212> TYPE: PRT
<213> ORGANISM: Artificial
<220> FEATURE:
<223> OTHER INFORMATION: Proteus Vulgaris

<400> SEQUENCE: 6

Ala Thr Ser Asn Pro Ala Phe Asp Pro Lys Asn Leu Met Gln Ser Glu
1               5                   10                  15

Ile Tyr His Phe Ala Gln Asn Asn Pro Leu Ala Asp Phe Ser Ser Asp
            20                  25                  30

Lys Asn Ser Ile Leu Thr Leu Ser Asp Lys Arg Ser Ile Met Gly Asn
        35                  40                  45

Gln Ser Leu Leu Trp Lys Trp Lys Gly Gly Ser Ser Phe Thr Leu His
    50                  55                  60

Lys Lys Leu Ile Val Pro Thr Asp Lys Glu Ala Ser Lys Ala Trp Gly
65                  70                  75                  80

Arg Ser Ser Thr Pro Val Phe Ser Phe Trp Leu Tyr Asn Glu Lys Pro
                85                  90                  95

Ile Asp Gly Tyr Leu Thr Ile Asp Phe Gly Glu Lys Leu Ile Ser Thr
            100                 105                 110

Ser Glu Ala Gln Ala Gly Phe Lys Val Lys Leu Asp Phe Thr Gly Trp
        115                 120                 125

Arg Thr Val Gly Val Ser Leu Asn Asn Asp Leu Glu Asn Arg Glu Met
    130                 135                 140

Thr Leu Asn Ala Thr Asn Thr Ser Ser Asp Gly Thr Gln Asp Ser Ile
145                 150                 155                 160

Gly Arg Ser Leu Gly Ala Lys Val Asp Ser Ile Arg Phe Lys Ala Pro
                165                 170                 175

Ser Asn Val Ser Gln Gly Glu Ile Tyr Ile Asp Arg Ile Met Phe Ser
            180                 185                 190

Val Asp Asp Ala Arg Tyr Gln Trp Ser Asp Tyr Gln Val Lys Thr Arg
        195                 200                 205

Leu Ser Glu Pro Glu Ile Gln Phe His Asn Val Lys Pro Gln Leu Pro
    210                 215                 220

Val Thr Pro Glu Asn Leu Ala Ala Ile Asp Leu Ile Arg Gln Arg Leu
225                 230                 235                 240

Ile Asn Glu Phe Val Gly Gly Glu Lys Glu Thr Asn Leu Ala Leu Glu
                245                 250                 255

Glu Asn Ile Ser Lys Leu Lys Ser Asp Phe Asp Ala Leu Asn Thr His
            260                 265                 270

Thr Leu Ala Asn Gly Gly Thr Gln Gly Arg His Leu Ile Thr Asp Lys
        275                 280                 285

Gln Ile Ile Ile Tyr Gln Pro Lys Asn Leu Asn Ser Gln Asp Lys Gln
```

```
                290                 295                 300
Leu Phe Asp Asn Tyr Val Ile Leu Gly Asn Tyr Thr Thr Leu Met Phe
305                 310                 315                 320

Asn Ile Ser Arg Ala Tyr Val Leu Glu Lys Asp Pro Thr Gln Lys Ala
                325                 330                 335

Gln Leu Lys Gln Met Tyr Leu Leu Met Thr Lys His Leu Leu Asp Gln
                340                 345                 350

Gly Phe Val Lys Gly Ser Ala Leu Val Thr Thr His His Trp Gly Tyr
                355                 360                 365

Ser Ser Arg Trp Trp Tyr Ile Ser Thr Leu Leu Met Ser Asp Ala Leu
                370                 375                 380

Lys Glu Ala Asn Leu Gln Thr Gln Val Tyr Asp Ser Leu Leu Trp Tyr
385                 390                 395                 400

Ser Arg Glu Phe Lys Ser Ser Phe Asp Met Lys Val Ser Ala Asp Ser
                405                 410                 415

Ser Asp Leu Asp Tyr Phe Asn Thr Leu Ser Arg Gln His Leu Ala Leu
                420                 425                 430

Leu Leu Leu Glu Pro Asp Asp Gln Lys Arg Ile Asn Leu Val Asn Thr
                435                 440                 445

Phe Ser His Tyr Ile Thr Gly Ala Leu Thr Gln Val Pro Pro Gly Gly
                450                 455                 460

Lys Asp Gly Leu Arg Pro Asp Gly Thr Ala Trp Arg His Glu Gly Asn
465                 470                 475                 480

Tyr Pro Gly Tyr Ser Phe Pro Ala Phe Lys Asn Ala Ser Gln Leu Ile
                485                 490                 495

Tyr Leu Leu Arg Asp Thr Pro Phe Ser Val Gly Glu Ser Gly Trp Asn
                500                 505                 510

Ser Leu Lys Lys Ala Met Val Ser Ala Trp Ile Tyr Ser Asn Pro Glu
                515                 520                 525

Val Gly Leu Pro Leu Ala Gly Arg His Pro Leu Asn Ser Pro Ser Leu
                530                 535                 540

Lys Ser Val Ala Gln Gly Tyr Tyr Trp Leu Ala Met Ser Ala Lys Ser
545                 550                 555                 560

Ser Pro Asp Lys Thr Leu Ala Ser Ile Tyr Leu Ala Ile Ser Asp Lys
                565                 570                 575

Thr Gln Asn Glu Ser Thr Ala Ile Phe Gly Glu Thr Ile Thr Pro Ala
                580                 585                 590

Ser Leu Pro Gln Gly Phe Tyr Ala Phe Asn Gly Gly Ala Phe Gly Ile
                595                 600                 605

His Arg Trp Gln Asp Lys Met Val Thr Leu Lys Ala Tyr Asn Thr Asn
                610                 615                 620

Val Trp Ser Ser Glu Ile Tyr Asn Lys Asp Asn Arg Tyr Gly Arg Tyr
625                 630                 635                 640

Gln Ser His Gly Val Ala Gln Ile Val Ser Asn Gly Ser Gln Leu Ser
                645                 650                 655

Gln Gly Tyr Gln Gln Glu Gly Trp Asp Trp Asn Arg Met Pro Gly Ala
                660                 665                 670

Thr Thr Ile His Leu Pro Leu Lys Asp Leu Asp Ser Pro Lys Pro His
                675                 680                 685

Thr Leu Met Gln Arg Gly Glu Arg Gly Phe Ser Gly Thr Ser Ser Leu
                690                 695                 700

Glu Gly Gln Tyr Gly Met Met Ala Phe Asp Leu Ile Tyr Pro Ala Asn
705                 710                 715                 720
```

```
Leu Glu Arg Phe Asp Pro Asn Phe Thr Ala Lys Lys Ser Val Leu Ala
            725                 730                 735

Ala Asp Asn His Leu Ile Phe Ile Gly Ser Asn Ile Asn Ser Ser Asp
            740                 745                 750

Lys Asn Lys Asn Val Glu Thr Thr Leu Phe Gln His Ala Ile Thr Pro
            755                 760                 765

Thr Leu Asn Thr Leu Trp Ile Asn Gly Gln Lys Ile Glu Asn Met Pro
            770                 775                 780

Tyr Gln Thr Thr Leu Gln Gln Gly Asp Trp Leu Ile Asp Ser Asn Gly
785                 790                 795                 800

Asn Gly Tyr Leu Ile Thr Gln Ala Glu Lys Val Asn Val Ser Arg Gln
            805                 810                 815

His Gln Val Ser Ala Glu Asn Lys Asn Arg Gln Pro Thr Glu Gly Asn
            820                 825                 830

Phe Ser Ser Ala Trp Ile Asp His Ser Thr Arg Pro Lys Asp Ala Ser
            835                 840                 845

Tyr Glu Tyr Met Val Phe Leu Asp Ala Thr Pro Glu Lys Met Gly Glu
            850                 855                 860

Met Ala Gln Lys Phe Arg Glu Asn Asn Gly Leu Tyr Gln Val Leu Arg
865                 870                 875                 880

Lys Asp Lys Asp Val His Ile Ile Leu Asp Lys Leu Ser Asn Val Thr
            885                 890                 895

Gly Tyr Ala Phe Tyr Gln Pro Ala Ser Ile Glu Asp Lys Trp Ile Lys
            900                 905                 910

Lys Val Asn Lys Pro Ala Ile Val Met Thr His Arg Gln Lys Asp Thr
            915                 920                 925

Leu Ile Val Ser Ala Val Thr Pro Asp Leu Asn Met Thr Arg Gln Lys
            930                 935                 940

Ala Ala Thr Pro Val Thr Ile Asn Val Thr Ile Asn Gly Lys Trp Gln
945                 950                 955                 960

Ser Ala Asp Lys Asn Ser Glu Val Lys Tyr Gln Val Ser Gly Asp Asn
            965                 970                 975

Thr Glu Leu Thr Phe Thr Ser Tyr Phe Gly Ile Pro Glu Ile Lys
            980                 985                 990

Leu Ser Pro Leu Pro
        995

<210> SEQ ID NO 7
<211> LENGTH: 997
<212> TYPE: PRT
<213> ORGANISM: Proteus vulgaris

<400> SEQUENCE: 7

Ala Thr Ser Asn Pro Ala Phe Asp Pro Lys Asn Leu Met Gln Ser Glu
1               5                   10                  15

Ile Tyr His Phe Ala Gln Asn Asn Pro Leu Ala Asp Phe Ser Ser Asp
            20                  25                  30

Lys Asn Ser Ile Leu Thr Leu Ser Asp Lys Arg Ser Ile Met Gly Asn
            35                  40                  45

Gln Ser Leu Leu Trp Lys Trp Lys Gly Ser Ser Phe Thr Leu His
            50                  55                  60

Lys Lys Leu Ile Val Pro Thr Asp Lys Glu Ala Ser Lys Ala Trp Gly
65                  70                  75                  80

Arg Ser Ser Thr Pro Val Phe Ser Phe Trp Leu Tyr Asn Glu Lys Pro
```

-continued

```
                                  85                   90                   95
         Ile Asp Gly Tyr Leu Thr Ile Asp Phe Gly Lys Leu Ile Ser Thr
                         100                 105                 110

Ser Glu Ala Gln Ala Gly Phe Lys Val Lys Leu Asp Phe Thr Gly Trp
                     115                 120                 125

Arg Thr Val Gly Val Ser Leu Asn Asn Asp Leu Glu Asn Arg Glu Met
         130                 135                 140

Thr Leu Asn Ala Thr Asn Thr Ser Ser Asp Gly Thr Gln Asp Ser Ile
         145                 150                 155                 160

Gly Arg Ser Leu Gly Ala Lys Val Asp Ser Ile Arg Phe Lys Ala Pro
                         165                 170                 175

Ser Asn Val Ser Gln Gly Glu Ile Tyr Ile Asp Arg Ile Met Phe Ser
                     180                 185                 190

Val Asp Asp Ala Arg Tyr Gln Trp Ser Asp Tyr Gln Val Lys Thr Arg
                     195                 200                 205

Leu Ser Glu Pro Glu Ile Gln Phe His Asn Val Lys Pro Gln Leu Pro
                     210                 215                 220

Val Thr Pro Glu Asn Leu Ala Ala Ile Asp Leu Ile Arg Gln Arg Leu
         225                 230                 235                 240

Ile Asn Glu Phe Val Gly Gly Glu Lys Glu Thr Asn Leu Ala Leu Glu
                         245                 250                 255

Glu Asn Ile Ser Lys Leu Lys Ser Asp Phe Asp Ala Leu Asn Thr His
                     260                 265                 270

Thr Leu Ala Asn Gly Gly Thr Gln Gly Arg His Leu Ile Thr Asp Lys
                     275                 280                 285

Gln Ile Ile Ile Tyr Gln Pro Glu Asn Leu Asn Ser Gln Asp Lys Gln
                     290                 295                 300

Leu Phe Asp Asn Tyr Val Ile Leu Gly Asn Tyr Thr Thr Leu Met Phe
         305                 310                 315                 320

Asn Ile Ser Arg Ala Tyr Val Leu Glu Lys Asp Pro Thr Gln Lys Ala
                         325                 330                 335

Gln Leu Lys Gln Met Tyr Leu Leu Met Thr Lys His Leu Leu Asp Gln
                     340                 345                 350

Gly Phe Val Lys Gly Ser Ala Leu Val Thr Thr His His Trp Gly Tyr
                     355                 360                 365

Ser Ser Arg Trp Trp Tyr Ile Ser Thr Leu Leu Met Ser Asp Ala Leu
                     370                 375                 380

Lys Glu Ala Asn Leu Gln Thr Gln Val Tyr Asp Ser Leu Leu Trp Tyr
         385                 390                 395                 400

Ser Arg Glu Phe Lys Ser Ser Phe Asp Met Lys Val Ser Ala Asp Ser
                         405                 410                 415

Ser Asp Leu Asp Tyr Phe Asn Thr Leu Ser Arg Gln His Leu Ala Leu
                     420                 425                 430

Leu Leu Leu Glu Pro Asp Asp Gln Lys Arg Ile Asn Leu Val Asn Thr
                     435                 440                 445

Phe Ser His Tyr Ile Thr Gly Ala Leu Thr Gln Val Pro Pro Gly Gly
                     450                 455                 460

Lys Asp Gly Leu Arg Pro Asp Gly Thr Ala Trp Arg His Glu Gly Asn
         465                 470                 475                 480

Tyr Pro Gly Tyr Ser Phe Pro Ala Phe Lys Asn Ala Ser Gln Leu Ile
                         485                 490                 495

Tyr Leu Leu Arg Asp Thr Pro Phe Ser Val Gly Glu Ser Gly Trp Asn
                     500                 505                 510
```

```
Ser Leu Lys Lys Ala Met Val Ser Ala Trp Ile Tyr Ser Asn Pro Glu
            515                 520                 525

Val Gly Leu Pro Leu Ala Gly Arg His Pro Leu Asn Ser Pro Ser Leu
        530                 535                 540

Lys Ser Val Ala Gln Gly Tyr Tyr Trp Leu Ala Met Ser Ala Lys Ser
545                 550                 555                 560

Ser Pro Asp Lys Thr Leu Ala Ser Ile Tyr Leu Ala Ile Ser Asp Lys
                565                 570                 575

Thr Gln Asn Glu Ser Thr Ala Ile Phe Gly Glu Thr Ile Thr Pro Ala
            580                 585                 590

Ser Leu Pro Gln Gly Phe Tyr Ala Phe Asn Gly Gly Ala Phe Gly Ile
        595                 600                 605

His Arg Trp Gln Asp Lys Met Val Thr Leu Lys Ala Tyr Asn Thr Asn
        610                 615                 620

Val Trp Ser Ser Glu Ile Tyr Asn Lys Asp Asn Arg Tyr Gly Arg Tyr
625                 630                 635                 640

Gln Ser His Gly Val Ala Gln Ile Val Ser Asn Gly Ser Gln Leu Ser
                645                 650                 655

Gln Gly Tyr Gln Gln Glu Gly Trp Asp Trp Asn Arg Met Pro Gly Ala
            660                 665                 670

Thr Thr Ile His Leu Pro Leu Lys Asp Leu Asp Ser Pro Lys Pro His
            675                 680                 685

Thr Leu Met Gln Arg Gly Glu Arg Gly Phe Ser Gly Thr Ser Ser Leu
        690                 695                 700

Glu Gly Gln Tyr Gly Met Met Ala Phe Asp Leu Ile Tyr Pro Ala Asn
705                 710                 715                 720

Leu Glu Arg Phe Asp Pro Asn Phe Thr Ala Lys Lys Ser Val Leu Ala
                725                 730                 735

Ala Asp Asn His Leu Ile Phe Ile Gly Ser Asn Ile Asn Ser Ser Asp
            740                 745                 750

Lys Asn Lys Asn Val Glu Thr Thr Leu Phe Gln His Ala Ile Thr Pro
        755                 760                 765

Thr Leu Asn Thr Leu Trp Ile Asn Gly Gln Lys Ile Glu Asn Met Pro
        770                 775                 780

Tyr Gln Thr Thr Leu Gln Gln Gly Asp Trp Leu Ile Asp Ser Asn Gly
785                 790                 795                 800

Asn Gly Tyr Leu Ile Thr Gln Ala Glu Lys Val Asn Val Ser Arg Gln
                805                 810                 815

His Gln Val Ser Ala Glu Asn Lys Asn Arg Gln Pro Thr Glu Gly Asn
            820                 825                 830

Phe Ser Ser Ala Trp Ile Asp His Ser Thr Arg Pro Lys Asp Ala Ser
        835                 840                 845

Tyr Glu Tyr Met Val Phe Leu Asp Ala Thr Pro Glu Lys Met Gly Glu
        850                 855                 860

Met Ala Gln Lys Phe Arg Glu Asn Asn Gly Leu Tyr Gln Val Leu Arg
865                 870                 875                 880

Lys Asp Lys Asp Val His Ile Ile Leu Asp Lys Leu Ser Asn Val Thr
                885                 890                 895

Gly Tyr Ala Phe Tyr Gln Pro Ala Ser Ile Glu Asp Lys Trp Ile Lys
            900                 905                 910

Lys Val Asn Lys Pro Ala Ile Val Met Thr His Arg Gln Lys Asp Thr
        915                 920                 925
```

-continued

| Leu | Ile | Val | Ser | Ala | Val | Thr | Pro | Asp | Leu | Asn | Met | Thr | Arg | Gln | Lys |
|---|---|---|---|---|---|---|---|---|---|---|---|---|---|---|---|
| | | | 930 | | | | 935 | | | | 940 | | | | |

| Ala | Ala | Thr | Pro | Val | Thr | Ile | Asn | Val | Thr | Ile | Asn | Gly | Lys | Trp | Gln |
|---|---|---|---|---|---|---|---|---|---|---|---|---|---|---|---|
| 945 | | | | | 950 | | | | | 955 | | | | | 960 |

| Ser | Ala | Asp | Lys | Asn | Ser | Glu | Val | Lys | Tyr | Gln | Val | Ser | Gly | Asp | Asn |
|---|---|---|---|---|---|---|---|---|---|---|---|---|---|---|---|
| | | | | 965 | | | | | 970 | | | | | 975 | |

| Thr | Glu | Leu | Thr | Phe | Thr | Ser | Tyr | Phe | Gly | Ile | Pro | Gln | Glu | Ile | Lys |
|---|---|---|---|---|---|---|---|---|---|---|---|---|---|---|---|
| | | | | 980 | | | | | 985 | | | | | 990 | |

| Leu | Ser | Pro | Leu | Pro |
|---|---|---|---|---|
| | | 995 | | |

<210> SEQ ID NO 8
<211> LENGTH: 2994
<212> TYPE: DNA
<213> ORGANISM: Proteus vulgaris

<400> SEQUENCE: 8

| gccaccagca | atcctgcatt | tgatcctaaa | aatctgatgc | agtcagaaat | ttaccatttt | 60 |
| gcacaaaata | acccattagc | agacttctca | tcagataaaa | actcaatact | aacgttatct | 120 |
| gataaacgta | gcattatggg | aaaccaatct | cttttatgga | aatggaaagg | tggtagtagc | 180 |
| tttactttac | ataaaaaact | gattgtcccc | accgataaag | aagcatctaa | agcatgggga | 240 |
| cgctcatcca | ccccgtttt | ctcattttgg | ctttacaatg | aaaaaccgat | tgatggttat | 300 |
| cttactatcg | atttcggaga | aaaactcatt | tcaaccagtg | aggctcaggc | aggcttttaaa | 360 |
| gtaaaattag | atttcactgg | ctggcgtact | gtgggagtct | cttaaaataa | cgatcttgaa | 420 |
| aatcgagaga | tgaccttaaa | tgcaaccaat | acctcctctg | atggtactca | agacagcatt | 480 |
| gggcgttctt | taggtgctaa | agtcgatagt | attcgttta | aagcgccttc | taatgtgagt | 540 |
| cagggtgaaa | tctatatcga | ccgtattatg | ttttctgtcg | atgatgctcg | ctaccaatgg | 600 |
| tctgattatc | aagtaaaaac | tcgcttatca | gaacctgaaa | ttcaatttca | aacgtaaag | 660 |
| ccacaactac | ctgtaacacc | tgaaaattta | gcggccattg | atcttattcg | ccaacgtcta | 720 |
| attaatgaat | ttgtcggagg | tgaaaaagag | acaaacctcg | cattagaaga | gaatatcagc | 780 |
| aaattaaaaa | gtgatttcga | tgctcttaat | actcacactt | tagcaaatgg | tggaacgcaa | 840 |
| ggcagacatc | tgatcactga | taaacaaatc | attatttatc | aaccagagaa | tcttaactct | 900 |
| caagataaac | aactatttga | taattatgtt | attttaggta | attacacgac | attaatgttt | 960 |
| aatattagcc | gtgcttatgt | gctggaaaaa | gatcccacac | aaaaggcgca | actaaagcag | 1020 |
| atgtacttat | taatgacaaa | gcatttatta | gatcaaggct | tgttaaagg | gagtgctttta | 1080 |
| gtgacaaccc | atcactgggg | atacagttct | cgttggtggt | atatttccac | gttattaatg | 1140 |
| tctgatgcac | taaagaagc | gaacctacaa | actcaagttt | atgattcatt | actgtggtat | 1200 |
| tcacgtgagt | ttaaaagtag | ttttgatatg | aaagtaagtg | ctgatagctc | tgatctagat | 1260 |
| tatttcaata | cctatctctcg | ccaacattta | gccttattac | tactagagcc | tgatgatcaa | 1320 |
| aagcgtatca | acttagttaa | tactttcagc | cattatatca | ctggcgcatt | aacgcaagtg | 1380 |
| ccaccgggtg | gtaaagatgg | tttacgccct | gatggtacag | catggcgaca | tgaaggcaac | 1440 |
| tatccgggct | actctttccc | agcctttaaa | aatgcctctc | agcttattta | tttattacgc | 1500 |
| gatacaccat | tttcagtggg | tgaaagtggt | tggaatagcc | tgaaaaaagc | gatggtttca | 1560 |
| gcgtggatct | acagtaatcc | agaagttgga | ttaccgcttg | caggaagaca | ccctcttaac | 1620 |
| tcaccttcgt | taaaatcagt | cgctcaaggc | tattactggc | ttgccatgtc | tgcaaaatca | 1680 |

```
tcgcctgata aaacacttgc atctatttat cttgcgatta gtgataaaac acaaaatgaa    1740
tcaactgcta tttttggaga aactattaca ccagcgtctt tacctcaagg tttctatgcc    1800
tttaatggcg gtgcttttgg tattcatcgt tggcaagata aaatggtgac actgaaagct    1860
tataacacca atgtttggtc atctgaaatt tataacaaag ataaccgtta tggccgttac    1920
caaagtcatg gtgtcgctca aatagtgagt aatggctcgc agcttttcaca gggctatcag   1980 caagaaggtt gggattggaa tagaatgcca ggggcaacca ctatccacct tcctcttaaa    2040
gacttagaca gtcctaaacc tcatacctta atgcaacgtg gagagcgtgg atttagcgga    2100
acatcatccc ttgaaggtca atatggcatg atggcattcg atcttattta tcccgccaat    2160
cttgagcgtt ttgatcctaa tttcactgcg aaaaagagtg tattagccgc tgataatcac    2220
ttaattttta ttggtagcaa tataaatagt agtgataaaa ataaaaatgt tgaaacgacc    2280
ttattccaac atgccattac tccaacatta atacccttt ggattaatgg acaaaagata     2340
gaaaacatgc cttatcaaac aacacttcaa caaggtgatt ggttaattga tagcaatggc    2400
aatggttact taattactca agcagaaaaa gtaaatgtaa gtcgccaaca tcaggtttca    2460
gcggaaaata aaaatcgcca accgacagaa ggaaacttta gctcggcatg gatcgatcac    2520
agcactcgcc ccaaagatgc cagttatgag tatatggtct ttttagatgc gacacctgaa    2580
aaaatgggag atgggcaca aaaattccgt gaaaataatg ggttatatca ggttcttcgt     2640
aaggataaag acgttcatat tattctcgat aaactcagca atgtaacggg atatgccttt    2700
tatcagccag catcaattga agacaaatgg atcaaaaagg ttaataaacc tgcaattgtg    2760
atgactcatc gacaaaaaga cactcttatt gtcagtgcag ttacacctga tttaaatatg    2820
actcgccaaa aagcagcaac tcctgtcacc atcaatgtca cgattaatgg caaatggcaa    2880
tctgctgata aaaatagtga agtgaaatat caggtttctg gtgataacac tgaactgacg    2940
tttacgagtt actttggtat tccacaagaa atcaaactct cgccactccc ttga         2994
```

<210> SEQ ID NO 9
<211> LENGTH: 2994
<212> TYPE: DNA
<213> ORGANISM: Artificial
<220> FEATURE:
<223> OTHER INFORMATION: Proteus Vulgaris

<400> SEQUENCE: 9

```
gccaccagca atcctgcatt tgatcctaaa aatctgatgc agtcagaaat ttaccatttt      60
gcacaaaata acccattagc agacttctca tcagataaaa actcaatact aacgttatct    120
gataaacgta gcattatggg aaaccaatct ctttttatgga aatggaaagg tggtagtagc    180
tttactttac ataaaaaact gattgtcccc accgataaag aagcatctaa agcatgggga    240
cgctcatcca cccccgtttt ctcattttgg ctttacaatg aaaaaccgat tgatggttat    300
cttactatcg atttcggaga aaactcatt tcaaccagtg aggctcaggc aggctttaaa     360
gtaaaattag atttcactgg ctggcgtact gtgggagtct ctttaaataa cgatcttgaa    420
aatcgagaga tgaccttaaa tgcaaccaac acctcctctg atggtactca agacagcatt    480
gggcgttctt taggtgctaa agtcgatagt attcgttta aagcgccttc taatgtgagt     540
cagggtgaaa tctatatcga ccgtattatg ttttctgtcg atgatgctcg ctaccaatgg    600
tctgattatc aagtaaaaac tcgcttatca gaacctgaaa ttcaatttca aacgtaaag     660 ccacaactac ctgtaacacc tgaaaattta gcggccattg atcttattcg ccaacgtcta    720
attaatgaat tgtcggagg tgaaaaagag acaaacctcg cattaaaaga gaatatcagc    780
```

```
aaattaaaaa gtgatttcga tgctcttaat actcacactt tagcaaatgg tggaacgcaa      840
ggcagacatc tgatcactga taaacaaatc attatttatc aaccagagaa tcttaactct      900
caagataaac aactatttga taattatgtt attttaggta attacacgac attaatgttt      960
aatattagcc gtgcttatgt gctggaaaaa gatcccacac aaaaggcgca actaaagcag     1020
atgtacttat taatgacaaa gcatttatta gatcaaggct tgttaaagg gagtgcttta     1080 gtgacaaccc atcactgggg atacagttct cgttggtggt atatttccac gttattaatg     1140
tctgatgcac taaaagaagc gaacctacaa actcaagttt atgattcatt actgtggtat     1200
tcacgtgagt ttaaaagtag ttttgatatg aaagtaagtg ctgatagctc tgatctagat     1260
tatttcaata ccttatctcg ccaacattta gccttattac tactagagcc tgatgatcaa     1320
aagcgtatca acttagttaa tactttcagc cattatatca ctggcgcatt aacgcaagtg     1380
ccaccgggtg gtaaagatgg tttacgccct gatggtacag catggcgaca tgaaggcaac     1440
tatccgggct actcttttcc cagcctttaaa aatgcctctc agcttattta tttattacgc     1500
gatacaccat tttcagtggg tgaaagtggt tggaatagcc tgaaaaaagc gatggtttca     1560
gcgtggatct acagtaatcc agaagttgga ttaccgcttg caggaagaca ccctcttaac     1620
tcaccttcgt taaaatcagt cgctcaaggc tattactggc ttgccatgtc tgcaaaatca     1680
tcgcctgata aaacttgc atctatttat cttgcgatta gtgataaaac acaaaatgaa     1740
tcaactgcta tttttggaga aactattaca ccagcgtctt tacctcaagg tttctatgcc     1800
tttaatggcg gtgcttttgg tattcatcgt tggcaagata aaatggtgac actgaaagct     1860
tataacacca atgtttggtc atctgaaatt tataacaaag ataaccgtta tggccgttac     1920
caaagtcatg gtgtcgctca aatagtgagt aatggctcgc agctttcaca gggctatcag     1980
caagaaggtt gggattggaa tagaatgcca ggggcaacca ctatccacct tcctcttaaa     2040
gacttagaca gtcctaaacc tcatacctta atgcaacgtg gagagcgtgg atttagcgga     2100
acatcatccc ttgaaggtca atatggcatg atggcattcg atcttattta tcccgccaat     2160
cttgagcgtt ttgatcctaa tttcactgcg aaaaagagtg tattagccgc tgataatcac     2220
ttaattttta ttggtagcaa tataaatagt agtgataaaa ataaaaatgt tgaaacgacc     2280
ttattccaac atgctattac tccaacatta aatacccttt ggattaatgg acaaaagata     2340
gaaaacatgc cttatcaaac aacacttcaa caaggtgatt ggttaattga tagcaatggc     2400
aatggttact taattactca agcagaaaaa gtaaatgtaa gtcgccaaca tcaggtttca     2460
gcggaaaata aaaatcgcca accgacagaa ggaaacttta gctcggcatg gatcgatcac     2520
agcactcgcc ccaaagatgc cagttatgag tatatggtct ttttagatgc gacacctgaa     2580
aaaatgggag agatggcaca aaaattccgt gaaaataatg ggttatatca ggttcttcgt     2640
aaggataaag acgttcatat tattctcgat aaactcagca atgtaacggg atatgccttt     2700
tatcagccag catcaattga agacaaatgg atcaaaaagg ttaataaacc tgcaattgtg     2760
atgactcatc gacaaaaaga cactcttatt gtcagtgcag ttacacctga tttaaatatg     2820
actcgccaaa aagcagcaac tcctgtcacc atcaatgtca cgattaatgg caaatggcaa     2880
tctgctgata aaaatagtga agtgaaatat caggttctg gtgataacac tgaactgacg     2940
tttacgagtt actttggtat tccacaagaa atcaaactct cgccactccc ttga          2994
```

<210> SEQ ID NO 10
<211> LENGTH: 2994
<212> TYPE: DNA

<213> ORGANISM: Artificial
<220> FEATURE:
<223> OTHER INFORMATION: Proteus Vulgaris

<400> SEQUENCE: 10

```
gccaccagca atcctgcatt tgatcctaaa aatctgatgc agtcagaaat ttaccatttt      60
gcacaaaata acccattagc agacttctca tcagataaaa actcaatact aacgttatct     120
gataaacgta gcattatggg aaaccaatct cttttatgga aatggaaagg tggtagtagc     180
tttactttac ataaaaaact gattgtcccc accgataaag aagcatctaa agcatgggga     240
cgctcatcca ccccgtttt ctcatttgg ctttacaatg aaaaaccgat tgatggttat      300
cttactatcg atttcggaga aaaactcatt tcaaccagtg aggctcaggc aggctttaaa     360
gtaaaattag atttcactgg ctggcgtact gtgggagtct ctttaaataa cgatcttgaa     420
aatcgagaga tgaccttaaa tgcaaccaat acctcctctg atggtactca agacagcatt     480
gggcgttctt taggtgctaa agtcgatagt attcgtttta aagcgccttc taatgtgagt     540
cagggtgaaa tctatatcga ccgtattatg ttttctgtcg atgatgctcg ctaccaatgg     600
tctgattatc aagtaaaaac tcgcttatca gaacctgaaa ttcaatttca aacgtaaag      660
ccacaactac ctgtaacacc tgaaaattta gcggccattg atcttattcg ccaacgtcta     720
attaatgaat tgtcggagg tgaaaaagag acaaacctcg cattagaaga aatatcagc      780
aaattaaaaa gtgatttcga tgctcttaat actcacactt tagcaaatgg tggaacgcaa     840
ggcagacatc tgatcactga taaacaaatc attatttatc aaccagagaa tcttaactct     900
caagataaac aactatttga taattatgtt attttaggta attacacgac attaatgttt     960
aatattagcc gtgcttatgt gctggaaaaa gatcccacac aaaaggcgca actaaagcag    1020
atgtacttat taatgacaaa gcatttatta gatcaaggct tgttaaagg gagtgctta     1080
gtgacaaccc atcactgggg atacagttct cgttggtggt atatttccac gttattaatg    1140
tctgatgcac taaagaagc gaacctacaa actcaagttt atgattcatt actgtggtat    1200
tcacgtgagt ttaaaagtag ttttgatatg aaagtaagtg ctgatagctc tgatctagat    1260
tatttcaata ccttatctcg ccaacattta gccttattac tactagagcc tgatgatcaa    1320
aagcgtatca acttagttaa tactttcagc cattatatca ctggcgcatt aacgcaagtg    1380
ccaccgggtg gtaaagatgg tttacgccct gatggtacag catggcgaca tgaaggcaac    1440
tatccgggct actctttccc agcctttaaa aatgcctctc agcttattta tttattacgc    1500
gatacaccat tttcagtggg tgaaagtggt tggaatagcc tgaaaaaagc gatggtttca    1560
gcgtggatct acagtaatcc agaagttgga ttaccgcttg caggaagaca ccctcttaac    1620
tcaccttcgt taaaatcagt cgctcaaggc tattactggc ttgccatgtc tgcaaaatca    1680
tcgcctgata aaacacttgc atctatttat cttgcgatta gtgataaaac acaaaatgaa    1740
tcaactgcta ttttggaga aactattaca ccagcgtctt tacctcaagg tttctatgcc    1800
tttaatggcg gtgcttttgg tattcatcgt tggcaagata aaatggtgac actgaaagct    1860
tataacacca atgttttggtc atctgaaatt tataacaaag ataaccgtta tggccgttac    1920
caaagtcatg gtgtcgctca aatagtgagt aatggctcgc agctttcaca gggctatcag    1980
caagaaggtt gggattggaa tagaatgcca ggggcaacca ctatccacct tcctcttaaa    2040
gacttaaaca gtcctaaacc tcataccta atgcaacgtg gagagcgtgg atttagcgga    2100
acatcatccc ttgaaggtca atatggcatg atggcattcg atcttatta tccgccaat     2160
cttgagcgtt ttgatcctaa tttcactgcg aaaaagagtg tattagccgc tgataatcac    2220
```

```
ttaattttta ttggtagcaa tataaatagt agtgataaaa ataaaaatgt tgaaacgacc    2280
ttattccaac atgccattac tccaacatta aatacccttt ggattaatgg acaaaagata    2340
gaaaacatgc cttatcaaac aacacttcaa caaggtgatt ggttaattga tagcaatggc    2400
aatggttact taattactca agcagaaaaa gtaaatgtaa gtcgccaaca tcaggtttca    2460
gcggaaaata aaaatcgcca accgacagaa ggaaactttg ctcggcatg gatcgatcac     2520 agcactcgcc ccaaagatgc cagtgatgag tatatggtct ttttagatgc gacacctgaa    2580
aaaatgggag agatggcaca aaaattccgt gaaaataatg ggttatatca ggttcttcgt    2640
aaggataaag acgttcatat tattctcgat aaactcagca atgtaacggg atatgccttt    2700
tatcagccag catcaattga agacaaatgg atcaaaaagg ttaataaacc tgcaattgtg    2760
atgactcatc gacaaaaaga cactcttatt gtcagtgcag ttacacctga tttaaatatg    2820
actcgccaaa aagcagcaac tcctgtcacc atcaatgtca cgattaatgg caaatggcaa    2880
tctgctgata aaaatagtga agtgaaatat caggtttctg gtgataacac tgaactgacg    2940
tttacgagtt actttggtat tccacaagaa atcaaactct cgccactccc ttga          2994

<210> SEQ ID NO 11
<211> LENGTH: 2994
<212> TYPE: DNA
<213> ORGANISM: Proteus vulgaris

<400> SEQUENCE: 11
gccaccagca atcctgcatt tgatcctaaa aatctgatgc agtcagaaat ttaccatttt      60
gcacaaaata acccattagc agacttctca tcagataaaa actcaatact aacgttatct     120
gataaacgta gcattatggg aaaccaatct cttttatgga aatggaaagg tggtagtagc     180
tttactttac ataaaaaact gattgtcccc accgataaag aagcatctaa agcatgggga     240
cgctcatcca cccccgtttt ctcatttttg g ctttacaatg aaaaaccgat tgatggttat    300
cttactatcg atttcggaga aaaactcatt tcaaccagtg aggctcaggc aggcttaaaa    360
gtaaaattag atttcactgg ctggcgtact gtgggagtct cttaaataa cgatcttgaa    420 aatcgagaga tgaccttaaa tgcaaccaat acctcctctg atggtactca agacagcatt    480
gggcgttctt taggtgctaa agtcgatagt attcgtttta agcgccttc taatgtgagt    540 cagggtgaaa tctatatcga ccgtattatg ttttctgtcg atgatgctcg ctaccaatgg    600
tctgattatc aagtaaaaac tcgcttatca gaacctgaaa ttcaattcca caacgtaaag    660
ccacaactac ctgtaacacc tgaaaattta gcggccattg atcttattcg ccaacgtcta    720
attaatgaat ttgtcggagg tgaaaaagag acaaacctcg cattagaaga aatatcagc    780 aaattaaaaa gtgatttcga tgctcttaat actcacactt agcaaatgg tggaacgcaa    840 ggcagacatc tgatcactga taaacaaatc attatttatc aaccagagaa tcttaactct    900
caagataaac aactatttga taattatgtt atttttaggta attacacgac attaatgttt    960
aatattagcc gtgcttatgt gctggaaaaa gatcccacac aaaaggcgca actaaagcag   1020
atgtacttat taatgacaaa gcatttatta gatcaaggct tgttaaagg gagtgcttta   1080 gtgacaaccc atcactgggg atacagttct cgttggtgg atatttccac gttattaatg   1140
tctgatgcac taaagaagc gaacctacaa actcaagttt atgattcatt actgtggtat   1200
tcacgtgagt ttaaaagtag ttttgatatg aaagtaagtg ctgatagctc tgatctagat   1260
tatttcaata ccttatctcg ccaacattta gccttattac tactagagcc tgatgatcaa   1320
```

| | |
|---|---|
| aagcgtatca acttagttaa tactttcagc cattatatca ctggcgcatt aacgcaagtg | 1380 |
| ccaccgggtg gtaaagatgg tttacgccct gatggtacag catggcgaca tgaaggcaac | 1440 |
| tatccgggct actctttccc agcctttaaa aatgcctctc agcttattta tttattacgc | 1500 |
| gatacaccat tttcagtggg tgaaagtggt tggaatagcc tgaaaaaagc gatggtttca | 1560 |
| gcgtggatct acagtaatcc agaagttgga ttaccgcttg caggaagaca ccctcttaac | 1620 |
| tcaccttcgt taaaatcagt cgctcaaggc tattactggc ttgccatgtc tgcaaaatca | 1680 |
| tcgcctgata aaacacttgc atctatttat cttgcgatta gtgataaaac acaaaatgaa | 1740 |
| tcaactgcta ttttggaga aactattaca ccggcgtctt tacctcaagg tttctatgcc | 1800 |
| tttaatggcg gtgcttttgg tattcatcgt tggcaagata aaatggtgac actgaaagct | 1860 |
| tataacacca atgtttggtc atctgaaatt tataacaaag ataaccgtta tggccgttac | 1920 |
| caaagtcatg gtgtcgctca aatagtgagt aatggctcgc agctttcaca gggctatcaa | 1980 |
| caagaaggtt gggattggaa tagaatgcca ggggcaacca ctatccacct tcctcttaaa | 2040 |
| gacttagaca gtcctaaacc tcatacccta atgcagcgtg gagagcgtgg atttagcgga | 2100 |
| acatcatccc ttgaaggtca atatggcatg atggcattcg atcttatttta tcccgccaat | 2160 |
| cttgagcgtt ttgatcctaa tttcactgcg aaaaagagtg tattagccgc tgataatcac | 2220 |
| ttaattttta ttggtagcaa tataaatagt agtgataaaa ataaaaatgt gaaacgacc | 2280 |
| ttattccaac atgccattac tccaacatta aatacccttt ggattaatgg acaaaagata | 2340 |
| gaaaacatgc cttatcaaac aacacttcaa caaggtgatt ggttaattga tagcaatggc | 2400 |
| aatggttact taattactca agcagaaaaa gtaaatgtaa gtcgccaaca tcaggtttca | 2460 |
| gcggaaaata aaaatcgcca accgacagaa ggaaacttta gctcggcatg gatcgatcac | 2520 |
| agcactcgcc ccaaagatgc cagttatgag tatatggtct ttttagatgc gacacctgaa | 2580 |
| aaaatgggag agatggcaca aaaattccgt gaaaataatg ggttatatca ggttcttcgt | 2640 |
| aaggataaag acgttcatat tattctcgat aaactcagca atgtaacggg atatgccttt | 2700 |
| tatcagccag catcaattga agacaaatgg atcaaaaagg ttaataaacc tgcaattgtg | 2760 |
| atgactcatc gacaaaaaga cactcttatt gtcagtgcag ttacacctga tttaaatatg | 2820 |
| actcgccaaa aagcagcaac tcctgtcacc atcaatgtca cgattaatgg caaatggcaa | 2880 |
| tctgctgata aaaatagtga agtgaaatat caggtttctg gtgataacac tgaactgacg | 2940 |
| tttacgagtt actttggtat tccacaagaa atcaaactct cgccactccc ttga | 2994 |

<210> SEQ ID NO 12
<211> LENGTH: 2994
<212> TYPE: DNA
<213> ORGANISM: Artificial
<220> FEATURE:
<223> OTHER INFORMATION: Proteus Vulgaris

<400> SEQUENCE: 12

| | |
|---|---|
| gccaccagca atcctgcatt tgatcctaaa aatctgatgc agtcagaaat ttaccatttt | 60 |
| gcacaaaata acccattagc agacttctca tcagataaaa actcaatact aacgttatct | 120 |
| gataaacgta gcattatggg aaaccaatct cttttatgga aatggaaagg tggtagtagc | 180 |
| tttactttac ataaaaaact gattgtcccc accgataaag aagcatctaa agcatgggga | 240 |
| cgctcatcca ccccgttttt ctcattttgg ctttacaatg aaaaaccgat tgatggttat | 300 |
| cttactatcg atttcggaga aaactcatt tcaaccagtg aggctcaggc aggctttaaa | 360 |
| gtaaaattag atttcactgg ctggcgtact gtgggagtct cttaaataa cgatcttgaa | 420 |

```
aatcgagaga tgaccttaaa tgcaaccaat acctcctctg atggtactca agacagcatt    480
ggacgttctt taggtgctaa agtcgatagt attcgtttta aagcgccttc taatgtgagt    540
cagggtgaaa tctatatcga ccgtattatg ttttctgtcg atgatgctcg ctaccaatgg    600
tctgattatc aagtaaaaac tcgcttatca gaacctgaaa ttcaatttca caacgtaaag    660
ccacaactac ctgtaacacc tgaaaattta gcggccattg atcttattcg ccaacgtcta    720
attaatgaat ttgtcggagg tgaaaaagag acaaacctcg cattagaaga gaatatcagc    780
aaattaaaaa gtgatttcga tgctcttaat actcacactt tagcaaatgg tggaacgcaa    840
ggcagacatc tgatcactga taaacaaatc attatttatc aaccagagaa tcttaactct    900
caagataaac aactatttga taattatgtt attttaggta attacacgac attaatgttt    960
aatattagcc gtgcttatgt gctggaaaaa gatcccacac aaaaggcgca actaaagcag   1020
atgtacttat taatgacaaa gcatttatta gatcaaggct tgttaaagg gagtgcttta    1080 gtgacaaccc atcactgggg atacagttcc cgttggtggt atatttccac gttattaatg   1140
tctgatgcac taaaagaagc gaacctacaa actcaagttt atgattcatt actgtggtat   1200
tcacgtgagt ttaaaagtag ttttgatatg aaagtaagtg ctgatagctc tgatctagat   1260
tatttcaata ccttatctcg ccaacattta gccttattac tactagagcc tgatgatcaa   1320
aagcgtatca acttagttaa tactttcagc cattatatca ctggcgcatt aacgcaagtg   1380
ccaccgggtg gtaaagatgg tttacgccct gatggtacag catggcgaca tgaaggcaac   1440
tatccgggct actctttccc agcctttaaa aatgcctctc agcttattta tttattacgc   1500
gatacaccat tttcagtggg tgaaagtggt tggaatagcc tgaaaaaagc gatggtttca   1560
gcgtggatct acagtaatcc agaagttgga ttaccgcttg caggaagaca ccctcttaac   1620
tcaccttcgt taaaatcagt cgctcaaggc tattactggc ttgccatgtc tgcaaaatca   1680
tcgcctgata aaacttgc atctatttat cttgcgatta gtgataaaac acaaaatgaa    1740
tcaactgcta ttttttggaga aactattaca ccagcgtctt tacctcaagg tttctatgcc   1800
tttaatggcg tgctttttgg cattcatcgt tggcaagata aaatggtgac actgaaagct   1860
tataacacca atgtttggtc atctgaaatt tataacaaag ataaccgtta tggccgttac   1920
caaagtcatg gtgtcgctca aatagtgagt aatggctcgc agctttcaca gggctatcag   1980
caagaaggtt gggattggaa tagaatgcca ggggcaacca ctatccacct tcctcttaaa   2040
gacttagaca gtcctaaacc tcataccttta atgcaacgtg gagagcgtgg atttagcgga   2100
acatcatccc ttgaaggtca atatggcatg atggcattcg atcttatta tcccgccaat    2160 cttgagcgtt ttgatcctaa tttcactgcg aaaagagtg tattagccgc tgataatcac   2220
ttaattttta ttggtagcaa tataaatagt agtgataaaa ataaaaatgt tgaaacgacc   2280
ttattccaac atgccattac tccaacatta ataccctttt ggattaatgg acaaaagata   2340
gaaaacatgc cttatcaaac aacacttcaa caaggtgatt ggttaattga tagcaatggc   2400
aatggttact aattactca agcagaaaaa gtaaatgtaa gtcgccaaca tcaggtttca    2460
gcggaaaata aaaatcgcca accgacagaa ggaaactttta gctcggcatg gatcgatcac   2520
agcactcgcc ccaaagatgc cagttatgag tatatgggtct ttttagatgc gacacctgaa  2580
aaaatgggag agatggcaca aaaattccgt gaaaataatg ggttatatca ggttcttcgt   2640
aaggataaag acgttcatat tattctcgat aaactcagca atgtaacggg atatgccttt   2700
tatcagccag catcaattga agacaaatgg atcaaaaagg ttaataaacc tgcaattgtg   2760
```

```
atgactcatc gacaaaaaga cactcttatt gtcagtgcag ttacacctga tttaaatatg    2820
actcgccaaa aagcagcaac tcctgtcacc atcaatgtca cgattaatgg caaatggcaa    2880
tctgctgata aaaatagtga agtgaaatat caggtttctg gtgataacac tgaactgacg    2940
tttacgagtt actttggtat tccacaagaa atcaaactct cgccactccc ttga          2994

<210> SEQ ID NO 13
<211> LENGTH: 2992
<212> TYPE: DNA
<213> ORGANISM: Artificial
<220> FEATURE:
<223> OTHER INFORMATION: Proteus Vulgaris

<400> SEQUENCE: 13
gccaccagca atcctgcatt tgatcctaaa aatctgatgc agtcagaaat ttaccatttt      60
gcacaaaata acccattagc agacttctca tcagataaaa actcaatact aacgttatct    120
gataaacgta gcattatggg aaaccaatct cttttatgga atggaaagg tggtagtagc     180 tttactttac ataaaaaact gattgtcccc accgataaag aagcatctaa agcatgggga    240
cgctcatcca cccccgtttt ctcatttttgg ctttacaatg aaaaaccgat tgatggttat   300
cttactatcg atttcggaga aaaactcatt tcaaccagtg aggctcaggc aggctttaaa    360
gtaaaattag atttcactgg ctggcgtact gtgggagtct ctttaaataa cgatcttgaa    420
aatcgagaga tgaccttaaa tgcaaccaat acctcctctg atggtactca agacagcatt   480
gggcgttctt taggtgctaa agtcgatagt attcgtttta aagcgccttc taatgtgagt    540
cagggtgaaa tctatatcga ccgtattatg ttttctgtcg atgatgctcg ctaccaatgg    600
tctgattatc aagtaaaaac tcgcttatca gaacctgaaa ttcaattca acgtaaag      660 ccacaactac ctgtaacacc tgaaaatta gcggccattg atcttattcg ccaacgtcta     720
attaatgaat tgtcggagg tgaaaagag acaaacctcg cattagaaga aatatcagc      780 aaattaaaaa gtgatttcga tgctcttaat actcacactt tagcaaatgg tggaacgcaa    840
ggcagacatc tgatcactga taaacaaatc attatttatc aaccagagaa tcttaactct    900
caagataaac aactatttga taattatgtt attttaggta attacacgac attaatgttt    960
aatattagcc gtgcttatgt gctggaaaaa gatcccacac aaaaggcgca actaaagcag   1020
atgtacttat taatgacaaa gcatttatta gatcaaggct tgttaaagg gagtgcttta   1080 gtgacaaccc atcactgggg atacagttct cgttggtggt atatttccac gttattaatg   1140
tctgatgcac taaagaagc gaacctacaa actcaagttt atgattcatt actgtggtat   1200
tcacgtgagt ttaaaagtag ttttgatatg aaagtaagtg ctgatagctc tgatctagat   1260
tatttcaata ccttatctcg ccaacattta gccttattac tactagagcc tgatgatcaa   1320
aagcgtatca acttagttaa tactttcagc cattatatca ctggcgcatt aacgcaagtg   1380
ccaccgggtg gtaaagatgg tttacgccct gatggtacag catggcgaca tgaaggcaac   1440
tatccgggct actctttccc agcctttaaa aatgcctctc agcttattta tttattacgc   1500
gatacaccat tttcagtggg tgaaagtggt tggaatagcc tgaaaaaagc gatggtttca   1560
gcgtggatct acagtaatcc agaagttgga ttaccgcttg caggaagaca ccctcttaac   1620
tcaccttcgt taaatcagt cgctcaaggc tattactggc ttgccatgtc tgcaaaatca   1680
tcgcctgata aaacacttgc atctatttat cttgcgatta gtgataaaac acaaaatgaa   1740
tcaactgcta ttttttggaga aactattaca ccagcgtctt tacctcaagg tttctatgcc   1800
tttaatggcg gtgcttttgg tattcatcgt tggcaagata aaatggtgac actgaaagct   1860
```

| | |
|---|---:|
| tataacacca atgtttggtc atctgaaatt tataacaaag ataaccgtta tggccgttac | 1920 |
| caaagtcatg gtgtcgctca aatagtgagt aatggctcgc agctttcaca gggctatcag | 1980 |
| caagaaggtt gggattggaa tagaatgcca ggggcaacca ctatccacct tcctcttaaa | 2040 |
| gacttagaca gtcctaaacc tcatacctta atgcaacgtg gagagcgtgg atttagcgga | 2100 |
| acatcatccc ttgaaggtca atatggcatg atggcattcg atcttattta tcccgccaat | 2160 |
| cttgagcgtt ttgatcctaa tttcactgcg aaaaagagtg tattaccgct gataatcact | 2220 |
| taatttttat tggtagcaat ataaatagta gtgataaaaa taaaaatgtt gaaacgacct | 2280 |
| tattccaaca tgccattact ccaacattaa atacccttg gattaatgga caaagatag | 2340 |
| aaaacatgcc ttatcaaaca acacttcaac aaggtgattg gttaattgat agcaatggca | 2400 |
| atggttactt aattactcaa gcagaaaaag taaatgtaag tcgccaacat caggtttcag | 2460 |
| cggaaaataa aaatcgccaa ccgacagaag gaaactttag ctcggcatgg atcgatcaca | 2520 |
| gcactcgccc caaagatgcc agttatgagt atatggtctt tttagatgcg acacctgaaa | 2580 |
| aaatgggaga gatggcacaa aaattccgtg aaaataatgg ttatatcag gttcttcgta | 2640 |
| aggataaaga cgttcatatt attctcgata aactcagcaa tgtaacggga tatgcctttt | 2700 |
| atcagccagc atcaattgaa gacaaatgga tcaaaaaggt taataaacct gcattgtgat | 2760 |
| gactcatcga caaaaagaca ctcttattgt cagtgcagtt acacctgatt taaatatgac | 2820 |
| tcgccaaaaa gcagcaactc ctgtcaccat caatgtcacg attaatggca atggcaatc | 2880 |
| tgctgataaa aatagtgaag tgaaatatca ggtttctggt gataacactg aactgacgtt | 2940 |
| tacgagttac tttggtattc cacaagaaat caaactctcg ccactccctt ga | 2992 |

<210> SEQ ID NO 14
<211> LENGTH: 2993
<212> TYPE: DNA
<213> ORGANISM: Artificial
<220> FEATURE:
<223> OTHER INFORMATION: Proteus Vulgaris

<400> SEQUENCE: 14

| | |
|---|---:|
| gccaccagca atcctgcatt tgatcctaaa aatctgatgc agtcagaaat ttaccatttt | 60 |
| gcacaaaata acccattagc agacttctca tcagataaaa actcaatact aacgttatct | 120 |
| gataaacgta gcattatggg aaaccaatct ctttttatgga aatggaaagg tggtagtagc | 180 |
| tttactttac ataaaaaact gattgtcccc accgataaag aagcatctaa agcatgggga | 240 |
| cgctcatcca ccccgtttt tcatttttgg ctttacaatg aaaaaccgat tgatggttat | 300 |
| cttactatcg atttcggaga aaaactcatt tcaaccagtg aggctcaggc aggctttaaa | 360 |
| gtaaaattag atttcactgg ctggcgtact gtgggagtct cttttaaataa cgatcttgaa | 420 |
| aatcgagaga tgaccttaaa tgcaaccaat acctcctctg atggtactca agacagcatt | 480 |
| gggcgttctt taggtgctaa agtcgatagt attcgttta aagcgccttc taatgtgagt | 540 |
| cagggtgaaa tctatatcga ccgtattatg ttttctgtcg atgatgctcg ctaccaatgg | 600 |
| tctgattatc aagtaaaaac tcgcttatca gaacctgaaa ttcaatttca aacgtaaag | 660 |
| ccacaactac ctgtaacacc tgaaaattta gcggccattg atcttattcg ccaacgtcta | 720 |
| attaatgaat tgtcggagg tgaaaagag acaaacctcg cattagaaga gaatatcagc | 780 |
| aaattaaaaa gtgatttcga tgctcttaat actcacactt tagcaaatgg tggaacgcaa | 840 |
| ggcagacatc tgatcactga taaacaaatc attatttatc aaccagagaa tcttaactct | 900 |

-continued

| | |
|---|---|
| caagataaac aactatttga taattatgtt attttaggta attacacgac attaatgttt | 960 |
| aatattagcc gtgcttatgt gctgaaaaag atcccacaca aaaggcgcaa ctaaagcaga | 1020 |
| tgtacttatt aatgacaaag catttattag atcaaggctt tgttaaaggg agtgctttag | 1080 |
| tgacaaccca tcactgggga tacagttctc gttggtggta tatttccacg ttattaatgt | 1140 |
| ctgatgcact aaaagaagcg aacctacaaa ctcaagttta tgattcatta ctgtggtatt | 1200 |
| cacgtgagtt taaagtagt tttgatatga agtaagtgc tgatagctct gatctagatt | 1260 |
| atttcaatac cttatctcgc caacatttag cctattact actagagcct gatgatcaaa | 1320 |
| agcgtatcaa cttagttaat actttcagcc attatatcac tggcgcatta acgcaagtgc | 1380 |
| caccgggtgg taaagatggt ttacgccctg atggtacagc atggcgacat gaaggcaact | 1440 |
| atccgggcta ctctttccca gcctttaaaa atgcctctca gcttatttat ttattacgcg | 1500 |
| atacaccatt ttcagtgggt gaaagtggtt ggaatagcct gaaaaaagcg atggtttcag | 1560 |
| cgtggatcta cagtaatcca gaagttggat taccgcttgc aggaagacac cctcttaact | 1620 |
| caccttcgtt aaaatcagtc gctcaaggct attactggct tgccatgtct gcaaaatcat | 1680 |
| cgcctgataa aacacttgca tctatttatc ttgcgattag tgataaaaca caaaatgaat | 1740 |
| caactgctat ttttggagaa actattacac cagcgtcttt acctcaaggt ttctatgcct | 1800 |
| ttaatggcgg tgcttttggt attcatcgtt ggcaagataa aatggtgaca ctgaaagctt | 1860 |
| ataacaccaa tgtttggtca tctgaaattt ataacaaaga taaccgttat ggccgttacc | 1920 |
| aaagtcatgg tgtcgctcaa atagtgagta atggctcgca gctttcacag ggctatcagc | 1980 |
| aagaaggttg ggattggaat agaatgccag gggcaaccac tatccacctt cctcttaaag | 2040 |
| acttagacag tcctaaacct cataccttaa tgcaacgtgg agagcgtgga tttagcggaa | 2100 |
| catcatccct tgaaggtcaa tatggcatga tggcattcga tcttatttat cccgccaatc | 2160 |
| ttgagcgttt tgatcctaat ttcactgcga aaaagagtgt attagccgct gataatcact | 2220 |
| taatttttat tggtagcaat ataaatagta gtgataaaaa taaaaatgtt gaaacgacct | 2280 |
| tattccaaca tgccattact ccaacattaa atacccttg gattaatgga caaaagatag | 2340 |
| aaaacatgcc ttatcaaaca acacttcaac aaggtgattg gttaattgat agcaatggca | 2400 |
| atggttactt aattactcaa gcagaaaaag taaatgtaag tcgccaacat caggtttcag | 2460 |
| cggaaaataa aaatcgccaa ccgacagaag gaaactttag ctcggcatgg atcgatcaca | 2520 |
| gcactcgccc caaagatgcc agttatgagt atatggtctt tttagatcg acacctgaaa | 2580 |
| aaatgggaga gatggcacaa aaattccgtg aaaataatgg ttatatcag gttcttcgta | 2640 |
| aggataaaga cgttcatatt attctcgata aactcagcaa tgtaacggga tatgcctttt | 2700 |
| atcagccagc atcaattgaa gacaaatgga tcaaaaaggt taataaacct gcaattgtga | 2760 |
| tgactcatcg acaaaaagac actcttattg tcagtgcagt tacacctgat ttaaatatga | 2820 |
| ctcgccaaaa agcagcaact cctgtcacca tcaatgtcac gattaatggc aaatggcaat | 2880 |
| ctgctgataa aaatagtgaa gtgaaatatc aggtttctgg tgataacact gaactgacgt | 2940 |
| ttacgagtta ctttggtatt ccacaagaaa tcaaactctc gccactccct tga | 2993 |

COMPOSITIONS AND METHODS OF USING CHONDROITINASE ABCI MUTANTS

CROSS-REFERENCE TO RELATED APPLICATIONS

This application is a continuation of U.S. patent application Ser. No. 14/790,075, filed Jul. 2, 2015, now U.S. Pat. No. 9,410,141, issued Aug. 9, 2016, which is a divisional application of U.S. patent application Ser. No. 13/849,420, filed Mar. 22, 2013, now U.S. Pat. No. 9,102,930, issued Aug. 11, 2015, which is continuation application of U.S. patent application Ser. No. 12/781,762, filed May 17, 2010, now U.S. Pat. No. 8,404,232, issued Mar. 26, 2013, which is a divisional application of U.S. patent application Ser. No. 11/870,350, filed Oct. 10, 2007, now U.S. Pat. No. 7,722,864, issued May 25, 2010, which claims the benefit of U.S. Provisional Patent Application No. 60/828,800 filed Oct. 10, 2006, the contents of each being incorporated by reference as if set forth in their entirety herein.

BACKGROUND

The spinal cord is made up of nerve fibers. Damage to the central nervous system, including the spinal cord, results in a loss of function. The most common types of spinal cord injuries (SCI) include contusions (bruising of the spinal cord) and compression injuries (caused by prolonged pressure on the spinal cord). After a spinal cord injury in the adult mammal, the inability of axons to regenerate may lead to loss of sensation, loss of motor function and/or loss of autonomic function, as well as permanent paralysis. One reason that neurons fail to regenerate is their inability to traverse the glial scar that develops following a spinal cord injury. The injury-induced lesion will develop glial scarring, which contains extracellular matrix molecules including chondroitin sulfate proteoglycans (CSPGs). CSPGs inhibit nerve tissue growth in vitro and nerve tissue regeneration at CSPGs rich regions in vivo. CSPGs are implicated in various other conditions including, for example, inflammation.

SUMMARY OF THE INVENTION

One embodiment of the present invention provides mutants of a chondroitinase ABCI enzyme.

In preferred embodiments, such chondroitinase ABCI mutant enzymes exhibit enhanced activity. In other preferred embodiments, such chondroitinase ABCI mutant enzymes exhibit enhanced resistance to inactivation, including inactivation from UV or heat exposure. Preferably, a chondroitinase ABCI mutant enzyme of the invention is selected from 055D2-3 (SEQ ID NO:1), 079B6-2 (SEQ ID NO:2), 079D2-2 (SEQ ID NO:3), 057G1-1 (SEQ ID NO:4), 023G6-4 (SEQ ID NO:5) 005B12-3 (SEQ ID NO: 6), and 021B8-3 (ATCC Deposit Designation PTA-8657).

The nucleotide sequence of wild type chondroitinase ABCI of Proteus vulgaris is set forth as SEQ ID NO:7 and the amino acid sequence of chondroitinase ABCI is set forth as SEQ ID NO:8.

The invention includes nucleic acids encoding the chondroitinase ABCI mutant enzymes of the invention and methods of their use. In an embodiment, the invention includes a nucleic acid sequence that encodes a chondroitinase ABCI mutant enzyme selected from 055D2-3 (SEQ ID NO:1), 079B6-2 (SEQ ID NO:2), 079D2-2 (SEQ ID NO:3), 057G1-1 (SEQ ID NO:4), 023G6-4 (SEQ ID NO:5) 005B12-3 (SEQ ID NO: 6), and 021B8-3 (ATCC Deposit Designation PTA-8657). Preferably, a nucleic acid sequence of the invention is selected from 055D2-3 nucleic acid (SEQ ID NO:9), 079B6-2 nucleic acid (SEQ ID NO:10), 079D2-2 nucleic acid (SEQ ID NO:11), 057G1-1 nucleic acid (SEQ ID NO:12), 023G6-4 nucleic acid (SEQ ID NO:13) 005B12-3 nucleic acid (SEQ ID NO: 14), and 021B8-3 (ATCC Deposit Designation PTA-8657).

Other embodiments of the present invention relate to methods of treating a patient in need of neurological functional recovery, including sensory, motor and autonomic function, after, for example, central nervous system ("CNS") injury or disease. The ABCI mutant enzymes of the invention can also be used to degrade CSPGs. Accordingly, an embodiment of the invention includes a method of degrading one or more CSPGs using a composition comprising an ABCI mutant enzyme of the invention. Preferably a composition of the invention effective for promoting neurological functional recovery comprises a chondroitinase ABCI mutant enzyme selected from 055D2-3 (SEQ ID NO:1), 079B6-2 (SEQ ID NO:2), 079D2-2 (SEQ ID NO:3), 057G1-1 (SEQ ID NO:4), 023G6-4 (SEQ ID NO:5) 005B12-3 (SEQ ID NO: 6), and 021B8-3 (ATCC Deposit Designation PTA-8657).

One embodiment of the present invention is a method for modifying access of cells to extravascular spaces and regions, comprising administering to a patient a composition comprising an enzyme of the invention. Another embodiment of the present invention is a method of reducing penetration of cells associated with inflammation into tissue of a patient. Preferably, the enzyme is selected from 055D2-3 (SEQ ID NO:1), 079B6-2 (SEQ ID NO:2), 079D2-2 (SEQ ID NO:3), 057G1-1 (SEQ ID NO:4), 023G6-4 (SEQ ID NO:5) 005B12-3 (SEQ ID NO: 6), and 021B8-3 (ATCC Deposit Designation PTA-8657).

Another embodiment of the present invention is a method for inhibiting extravasation of cells associated with inflammation from blood vessels, comprising administering to a patient a composition comprising an enzyme that cleaves chondroitin sulfate proteoglycans. In an embodiment, an enzyme of the invention prevents cells selected from the group consisting of white blood cells, leukocytes, neutrophils, eosinophils, basophils, lymphocytes, B-cells, T-cells, monocytes, and macrophages from leaving the blood stream. Preferably, the enzyme is selected from 055D2-3 (SEQ ID NO:1), 079B6-2 (SEQ ID NO:2), 079D2-2 (SEQ ID NO:3), 057G1-1 (SEQ ID NO:4), 023G6-4 (SEQ ID NO:5) 005B12-3 (SEQ ID NO: 6), and 021B8-3 (ATCC Deposit Designation PTA-8657).

Another embodiment of the invention is a method of treating inflammation in a patient comprising administering to the patient an enzyme that cleaves chondroitin sulfate proteoglycans. Preferably, the enzyme is selected from 055D2-3 (SEQ ID NO:1), 079B6-2 (SEQ ID NO:2), 079D2-2 (SEQ ID NO:3), 057G1-1 (SEQ ID NO:4), 023G6-4 (SEQ ID NO:5) 005B12-3 (SEQ ID NO: 6), and 021B8-3 (ATCC Deposit Designation PTA-8657). In various embodiments of the present invention, inflammation is associated with disease or injury, such as chronic inflammatory disease and central nervous system disease.

Another embodiment of the invention is a method of preventing inflammation in a patient, comprising administering to the patient a composition comprising an enzyme that cleaves chondroitin sulfate proteoglycans. Preferably, the enzyme is selected from 055D2-3 (SEQ ID NO:1), 079B6-2 (SEQ ID NO:2), 079D2-2 (SEQ ID NO:3), 057G1-1 (SEQ ID NO:4), 023G6-4 (SEQ ID NO:5) 005B12-3 (SEQ ID NO: 6), and 021B8-3 (ATCC Deposit Designation PTA-8657).

Another embodiment of the present invention is a method of treating inflammation in a patient, comprising extracting cells associated with inflammation from a patient, subjecting the cells to an enzyme that cleaves chondroitin sulfate proteoglycans ex vivo to modify the cells, and administering the modified blood cells into the patient. Preferably, the enzyme is selected from 055D2-3 (SEQ ID NO:1), 079B6-2 (SEQ ID NO:2), 079D2-2 (SEQ ID NO:3), 057G1-1 (SEQ ID NO:4), 023G6-4 (SEQ ID NO:5) 005B12-3 (SEQ ID NO: 6), and 021B8-3 (ATCC Deposit Designation PTA-8657).

In an embodiment, an enzymes of the present invention is used to treat a patient in need of regeneration of damaged neurological tissue. In another embodiment, an enzyme of the invention is used to facilitate diffusion and transport of therapeutic molecules capable of blocking and/or overcoming the activity of neuronal growth inhibitory molecules into damaged or diseased tissue. Embodiments of the present invention include compositions comprising chondroitinase ABCI mutant enzymes of the invention and methods for their use to facilitate delivery and diffusion of therapeutics or diagnostic agents, and agents that promote regeneration of nerves and axons, into cells or tissues. Preferably a composition of the invention is effective in the regeneration of damaged neurological tissue or to facilitate diffusion or transport. In an embodiment, a composition of the invention comprises a chondroitinase ABCI mutant enzyme selected from 055D2-3 (SEQ ID NO:1), 079B6-2 (SEQ ID NO:2), 079D2-2 (SEQ ID NO:3), 057G1-1 (SEQ ID NO:4), 023G6-4 (SEQ ID NO:5) 005B12-3 (SEQ ID NO: 6), and 021B8-3 (ATCC Deposit Designation PTA-8657).

Further embodiments relate to methods of promoting neuronal outgrowth and use in treating spinal cord injuries and related disorders of the CNS by administering such a chondroitinase ABCI mutant enzyme. Preferably a composition of the invention effective for promoting neuronal outgrowth comprises a chondroitinase ABCI mutant enzyme selected from 055D2-3 (SEQ ID NO:1), 079B6-2 (SEQ ID NO:2), 079D2-2 (SEQ ID NO:3), 057G1-1 (SEQ ID NO:4), 023G6-4 (SEQ ID NO:5) 005B12-3 (SEQ ID NO: 6), and 021B8-3 (ATCC Deposit Designation PTA-8657).

DESCRIPTION OF THE DRAWINGS

In part, other aspects, features, benefits and advantages of the embodiments of the present invention will be apparent with regard to the following description, appended claims and accompanying drawings where:

DETAILED DESCRIPTION

Figure 1:
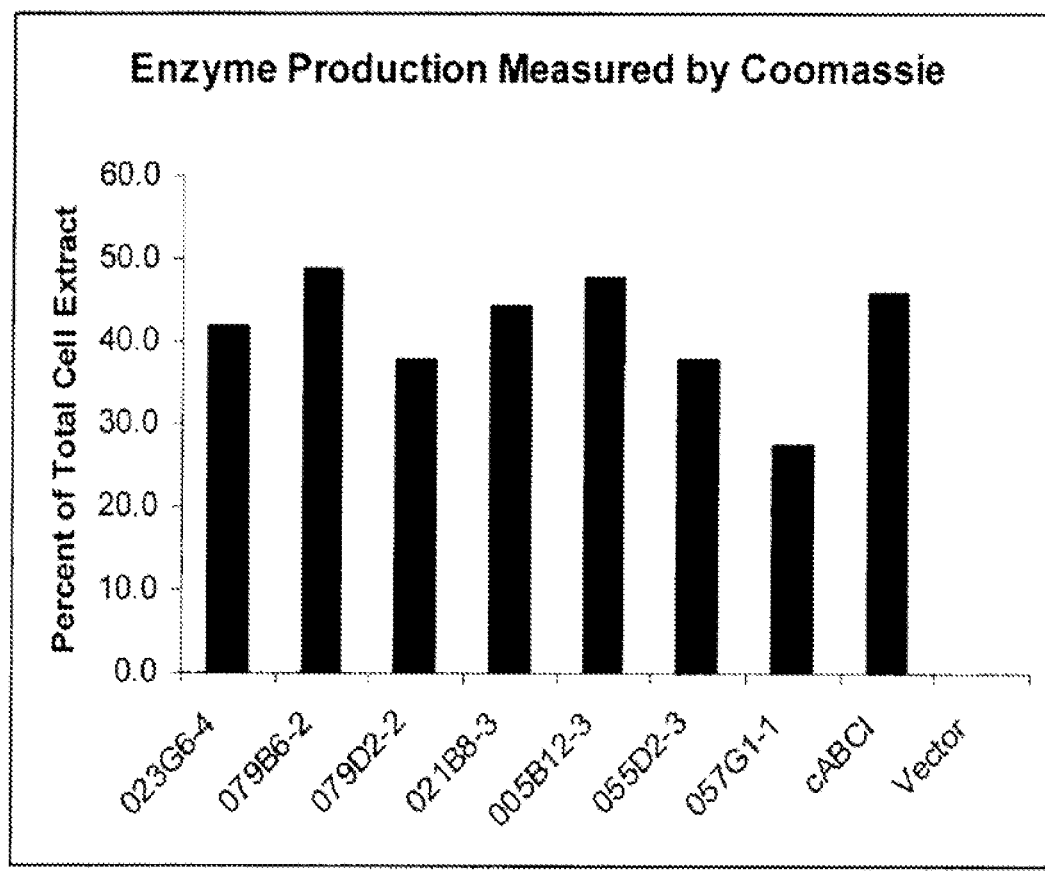
FIG. 1 shows relative mutant chondroitinase protein levels in whole cell lysates, as more fully described below in Example 3.

Before the present compositions and methods are described, it is to be understood that this invention is not limited to the particular molecules, compositions, methodologies or protocols described, as these may vary. It is also to be understood that the terminology used in the description is for the purpose of describing the particular versions or embodiments only, and is not intended to limit the scope of the present invention which will be limited only by the appended claims.

It must also be noted that as used herein and in the appended claims, the singular forms "a," "an," and "the" include plural reference unless the context clearly dictates otherwise. Thus, for example, reference to a "cell" is a reference to one or more cells and equivalents thereof known to those skilled in the art, and so forth. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are described. All publications mentioned herein are incorporated by reference. Nothing herein is to be construed as an admission that the invention is not entitled to antedate such disclosure by virtue of prior invention.

As used herein, the term "about" means plus or minus 10% of the numerical value of the number with which it is being used. Therefore, about 50% means in the range of 45%-55%.

"Administering" when used in conjunction with a therapeutic means to administer a therapeutic directly into or onto a target tissue or to administer a therapeutic to a patient whereby the therapeutic positively impacts the tissue to which it is targeted. Thus, as used herein, the term "administering," can include, but is not limited to, providing an enzyme into or onto a target tissue; providing an enzyme systemically to a patient by, e.g., intravenous injection whereby the therapeutic reaches the target tissue; providing an enzyme in the form of the encoding sequence thereof to the target tissue (e.g., by so-called gene-therapy techniques).

The term "animal" as used herein includes, but is not limited to, humans and non-human vertebrates such as wild, domestic and farm animals.

The term "improves" is used to convey that the present invention changes either the appearance, form, characteristics and/or the physical attributes of the target to which it is being provided, applied or administered. The change may be demonstrated by any of the following alone or in combination, including degradation of the CSPGs of the lesioned area of the spinal cord or within the CNS or restoring, in whole or in part, motor, sensory or autonomic function of the mammal.

The term "inhibiting" includes administering a compound of the present invention to prevent the onset of the symptoms, alleviating the symptoms, or eliminating the disease, condition or disorder.

By "pharmaceutically acceptable," it is meant the carrier, diluent or excipient must be compatible with the other ingredients of the formulation and not deleterious to the recipient thereof.

The term "recombinant protein" refers to a polypeptide of the present invention which is produced by recombinant DNA techniques, wherein generally, DNA encoding a polypeptide is inserted into a suitable expression vector which is in turn used to transform a host cell to produce the protein. Moreover, the phrase "derived from," with respect to a recombinant gene, is meant to include within the meaning of "recombinant protein" those proteins having an amino acid sequence of a native protein, or an amino acid sequence similar thereto which is generated by mutations including substitutions and deletions (including truncation) of a naturally occurring form of the protein.

As used herein, the term "therapeutic" means an agent utilized to treat, combat, ameliorate, prevent or improve an unwanted condition or disease of a patient. In part, embodiments of the present invention are directed to the treatment of the central nervous system, such as degradation of the CSPGs of a lesioned area of spinal cord or within the CNS, or restoration, in whole or in part, of a motor, sensory or autonomic function of the mammal. Other embodiments of the invention are directed to inhibiting extravasation of cells. Yet other embodiments of the invention are directed to enhancing or facilitating diffusion, as discussed herein. Other embodiments of the invention are directed to treating or preventing inflammation.

The terms "therapeutically effective amount" or "effective amount", as used herein, may be used interchangeably and refer to an amount of a therapeutic compound component of the present invention. For example, a therapeutically effective amount of a therapeutic compound is a predetermined amount calculated to achieve the desired effect, i.e., to effectively treat an injury to the central nervous system. For example, a therapeutic compound comprising a therapeutically effective amount of a chondroitinase formulated to provide a stable, active enzyme, is sufficient to degrade the CSPGs of a lesioned area of the spinal cord or an amount sufficient to restore, in whole or in part, a motor, sensory or autonomic function of the mammal and may result in a regeneration of neurons in a central nervous system, such as by promoting axonal growth into an injured area. A therapeutically effective amount also includes an amount effective to degrade CSPGs and thereby promote recovery of neurological function. A therapeutically effective amount also includes an amount sufficient to modify extravasation of cells or to reduce or prevent inflammation.

The terms "treat," "treated," or "treating" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

The process of "extravasation" is known as the transmigration of cells, such as leukocytes, from a blood vessel into the extravascular space, and may further include migration into surrounding tissue. As used herein the term "leukocyte" is used to refer to the class of cells associated with inflammation, which may also be defined as any of the various blood cells that have a nucleus and cytoplasm. Also known as white blood cells, leukocytes include neutrophils, eosinophils, basophils, lymphocytes, such as B-cells, T-cells, monocytes and macrophages. Four types of leukocytes are particularly important in immune defense, including neutrophils, which release several antibacterial proteins; monocytes, which are the precursors of macrophages that engulf and destroy foreign particles, and T and B lymphocytes, which are the antigen-recognizing cells of the immune cells.

The term "vector" refers to a vehicle which can transport the nucleic acid molecules. The nucleic acid molecules encoding the chondroitinase polypeptide are covalently linked to the vector nucleic acid. With this aspect of the invention, the vector can be, for example, a plasmid, single or double stranded phage, a single or double stranded RNA or DNA viral vector, or artificial chromosome, such as a BAC, PAC, YAC, OR MAC.

One embodiment of the present invention provides mutants of chondroitinase ABCI. In a preferred embodiment, the chondroitinase ABCI mutant enzymes and nucleic acids encoding them are those of the isolated clones selected from 055D2-3 (deposited with American Type Culture Collection (ATCC), 10801 University Blvd., Manassas, Va. 20110-2209 on Sep. 26, 2007 and having ATCC Deposit Designation PTA-8661) (SEQ ID NO:1 and SEQ ID NO:9), 079B6-2 (deposited with ATCC on Sep. 26, 2007 and having ATCC Deposit Designation PTA-8662) (SEQ ID NO:2 and SEQ ID NO:10), 079D2-2 (deposited with ATCC on Sep. 26, 2007 and having ATCC Deposit Designation PTA-8659) (SEQ ID NO:3 and SEQ ID NO:11), 021B8-3 (deposited with ATCC on Sep. 26, 2007 and having ATCC Deposit Designation PTA-8657), 057G1-1 (deposited with ATCC on Sep. 26, 2007 and having ATCC Deposit Designation PTA-8658) (SEQ ID NO:4 and SEQ ID NO: 12), 023G6-4 (deposited with ATCC on Sep. 26, 2007 and having ATCC Deposit Designation PTA-8663) (SEQ ID NO:5 and SEQ ID NO:13) and 005B12-3 (deposited with ATCC on Sep. 26, 2007 and having ATCC Deposit Designation PTA-8660) (SEQ ID NO: 6 and SEQ ID NO:14). The nucleotide sequence of chondroitinase ABCI is set forth as SEQ ID NO. 7 and the amino acid sequence of chondroitinase ABCI is set forth as SEQ ID NO. 8.

The ATCC deposits referred to herein will be maintained under the terms of the Budapest Treaty on the International Recognition of the Deposit of Micro-Organisms for purposes of Patent Procedure. These deposits are provided merely as convenience to those of skill in the art and are not an admission that a deposit is required under 35 U.S.C. § 112. The sequence(s) of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

One embodiment of the present invention provides mutants of chondroitinase ABCI. In preferred embodiments, such chondroitinase ABCI mutant enzymes exhibit enhanced activity. In an embodiment, an enzyme of the invention has an enzyme activity level (as measured by its ability to degrade a CSPG substrate) that is up to about two times greater than the activity level of the corresponding wild type enzyme. In another embodiment, an enzyme of the invention has an enzyme activity level that is up to about three times greater than the activity of the corresponding wild type chondroitinase. In an embodiment, the chondroitinase ABCI mutant enzymes are selected from 055D2-3 (SEQ ID NO:1), 079B6-2 (SEQ ID NO:2), 079D2-2 (SEQ ID NO:3), 057G1-1 (SEQ ID NO:4), 023G6-4 (SEQ ID NO:5) 005B12-3 (SEQ ID NO: 6), and 021B8-3 (ATCC Deposit Designation PTA-8657). More preferably, the enzyme is selected from the group consisting of 055D2-3 (SEQ ID NO:1), 079B6-2 (SEQ ID NO:2), and 023G6-4 (SEQ ID NO:5).

The invention includes nucleic acids encoding the chondroitinase ABCI mutant enzymes of the invention having enhanced activity, and methods of their use. In an embodiment, the invention includes nucleic acid sequences that encode the chondroitinase ABCI mutant enzymes selected from 055D2-3 (SEQ ID NO:1), 079B6-2 (SEQ ID NO:2), 079D2-2 (SEQ ID NO:3), 057G1-1 (SEQ ID NO:4), 023G6-4 (SEQ ID NO:5) 005B12-3 (SEQ ID NO: 6), and 021B8-3 (ATCC Deposit Designation PTA-8657). Preferably, a nucleic acid sequence of the invention is selected from 055D2-3 nucleic acid (SEQ ID NO:9), 079B6-2 nucleic acid (SEQ ID NO:10), 079D2-2 nucleic acid (SEQ ID NO:11), 057G1-1 nucleic acid (SEQ ID NO:12), 023G6-4 nucleic acid (SEQ ID NO:13) 005B12-3 nucleic acid (SEQ ID NO: 14), and 021B8-3 (ATCC Deposit Designation PTA-8657).

In other preferred embodiments, such chondroitinase ABCI mutant enzymes exhibit enhanced resistance to inactivation. In an embodiment, enhanced resistance to inactivation permits an enzyme of the invention to remain active following a stress (such as heat or UV) for a time that is up to about ten-fold longer than for the corresponding wild type chondroitinase. For example, if a wild type chondroitinase maintains measurable activity for up to about 3 days, a chondroitinase enzyme of the invention maintains measurable activity for up to about 30 days under the same conditions. In an embodiment, the chondroitinase ABCI mutant enzymes having increased resistance to inactivation are selected from 055D2-3 (SEQ ID NO:1), 079B6-2 (SEQ ID NO:2), 079D2-2 (SEQ ID NO:3), 057G1-1 (SEQ ID NO:4), 023G6-4 (SEQ ID NO:5) 005B12-3 (SEQ ID NO: 6), and 021B8-3 (ATCC Deposit Designation PTA-8657). More preferably, the enzyme is selected from the group consisting of 055D2-3 (SEQ ID NO:1), 079B6-2 (SEQ ID NO:2), and 023G6-4 (SEQ ID NO:5).

The invention includes nucleic acids encoding the chondroitinase ABCI mutant enzymes of the invention having enhanced resistance to inactivation, and methods of their use. In an embodiment, the invention includes nucleic acid sequences that encode the chondroitinase ABCI mutant enzymes selected from 055D2-3 (SEQ ID NO:1), 079B6-2 (SEQ ID NO:2), 079D2-2 (SEQ ID NO:3), 057G1-1 (SEQ ID NO:4), 023G6-4 (SEQ ID NO:5) 005B12-3 (SEQ ID NO: 6), and 021B8-3 (ATCC Deposit Designation PTA-8657). Preferably, a nucleic acid sequence of the invention is selected from 055D2-3 nucleic acid (SEQ ID NO:9), 079B6-2 nucleic acid (SEQ ID NO:10), 079D2-2 nucleic acid (SEQ ID NO:11), 057G1-1 nucleic acid (SEQ ID NO:12), 023G6-4 nucleic acid (SEQ ID NO:13) 005B12-3 nucleic acid (SEQ ID NO: 14), and 021B8-3 (ATCC Deposit Designation PTA-8657).

In a further embodiment, a mutant chondroitinase ABCI enzyme is provided having increased stability. The enzyme exhibits increased resistance to inactivation under stressed conditions, including exposure to UV light or heat, as compared to that of wild-type ABCI enzyme. In a preferred embodiment, the enzyme exhibits increased stability compared to wild-type chondroitinase ABCI enzyme following a challenge by a stress. In an embodiment, the chondroitinase ABCI mutant enzymes having increased stability are selected from 055D2-3 (SEQ ID NO:1), 079B6-2 (SEQ ID NO:2), 079D2-2 (SEQ ID NO:3), 057G1-1 (SEQ ID NO:4), 023G6-4 (SEQ ID NO:5) 005B12-3 (SEQ ID NO: 6), and 021B8-3 (ATCC Deposit Designation PTA-8657). More preferably, the enzyme is selected from the group consisting of 055D2-3 (SEQ ID NO:1), 079B6-2 (SEQ ID NO:2), and 023G6-4 (SEQ ID NO:5).

The enzymes of the invention may be used to prevent, treat and alleviate symptoms of inflammation and inflammatory states. In an embodiment, a chondroitinase ABCI mutant enzyme of the invention is used to prevent, treat or alleviate symptoms of chronic inflammatory diseases. A chondroitinase ABCI mutant enzyme of the invention may be used to treat inflammation associated with pain, injection and diseased states. An enzyme of the invention may be used to prevent tissue damage that is associated with inflammatory processes. Several conditions, including chronic inflammatory diseases, may benefit from controlled immune response. Some examples of chronic inflammatory diseases include Asthma, Rheumatoid Arthritis (RA), Multiple Sclerosis (MS), Systemic Lupus Erythematosus (SLE), and Chronic Obstructive Pulmonary Disease (COPD). An enzyme of the invention may also be used to regulate the inflammatory state associated with one or more disease selected from the group consisting of central nervous system disorders, central nervous system diseases, spinal cord injury, and cardiovascular diseases.

Inflammatory diseases, autoimmune diseases, and diseases with an inflammatory component that may be treated with a composition comprising an enzyme of the invention also include Multiple Sclerosis, Meningitis, Encephalitis, Rheumatoid arthritis, Osteo arthritis, Lupus, Wegener's granulomatosis, Inflammatory bowel disease: Crohn's colitis, ulcerative colitis, Asthma, Chlamydia infections, Syphilis, Thyroiditis, Temporal arteritis, Polymyalgia rheumatica, Ankylosing spondylitis, Psoriasis, Vasculitiditis such as: temporal arteritis, Takayasu arteritis, syphilitic aortitis, infectious aneurisms, atherosclerotic aneurisms, inflammatory abdominal aortic aneurysms, polyarteritis nodosa, Kawasaki disease, Churg-Strauss, hypersensitivity vasculitis, Buerger's disease, mesenteric inflammatory veno-occlusive disease, phlebitis, thrombophlebitis, Churg-Strauss, primary angiitis of the CNS, drug induced vasculitis, any secondary arteritis or venulitis, Gout, Pseudogout, Sarcoidosis, Sjogren's Syndrome, Myelitis, Salpingitis of any etiology, Uveitis, Pelvic Inflammatory Disease, Glomerulonephritis of any etiology, Goodpasture's syndrome, Pericarditis, Myocarditis, Endocarditis, and Pancreatitis.

One embodiment of the present invention is a method for modifying access of cells to extravascular spaces and regions comprising administering to a patient a composition comprising a chondroitinase ABCI mutant enzyme of the invention. Another embodiment of the present invention is a method of reducing penetration of cells associated with inflammation into tissue of a patient comprising administering to a patient a composition comprising an enzyme of the invention.

Another embodiment of the invention is a method for inhibiting extravasation of cells associated with inflammation from blood vessels comprising administering to a patient a composition comprising a chondroitinase ABCI mutant enzyme of the invention. The enzyme of the invention may prevent extravasation of cells selected from the group selected from the group consisting of white blood cells, leukocytes, neutrophils, eosinophils, basophils, lymphocytes, B-cells, T-cells, monocytes, and macrophages cells from leaving the blood stream.

Another embodiment of the present invention is a method of treating inflammation in a patient, the method comprising extracting circulating cells from a patient, subjecting the cells to a chondroitinase ABCI mutant enzyme of the invention ex vivo to modify the cells, and administering the modified blood cells into the patient. Therefore, the use of the enzymes described herein may also be directed to ex vivo treatments.

Extraction of cells may be accomplished by a variety of methods including, but not limited to, intravenous blood withdrawal, transfusion, dialysis, bypass, organ transplant and other similar methods that result in removal of cells from the body. Administration of the cells may be accomplished by the same methods used to extract the cells, including, but not limited to, intravenous administration, transfusion, dialysis, bypass, organ transplant and the like.

A circulating leukocyte with ligands expressed on its surface containing carbohydrate chains may be extracted from a patient and modified ex vivo by one or more of the ABCI mutant enzymes of the invention. Extraction may be accomplished by blood draw, transfusion, dialysis, bypass, or organ transplant. As described, a chondroitinase ABCI mutant enzyme of the invention modifies the carbohydrate chains. Once modified, the leukocytes may be reintroduced into a patient's blood stream. Modified leukocytes will be incapable of adhering to endothelial expressed selectins, mucins, and integrins. Timing of an extraction and reintroduction into the bloodstream may be optimized by observing the inflammatory response and the appearance of leukocytes in the blood stream, once said cells are signaled to specific sites of injury or infection. As a result, extravasation of leukocytes into tissue may be regulated, prevented, reduced, or controlled. Such regulation may be used in methods and treatments as directed to control and treat inflammatory response and diseases with an inflammatory component.

The compositions of the present invention can be used for the treatment of spinal cord injuries and in the promotion of regeneration of axons. The compositions of the present invention can also be used to promote plasticity, regrowth, repair, and/or regeneration of dysfunctional neurons in the CNS that have been damaged as a result of disease, such as degenerative diseases including Alzheimer's and Parkinson's disease. Advantageously, the use of proteoglycan degrading polypeptides or membrane transducing polypeptides in the compositions of the present invention also promote diffusion and access of damage or diseased tissue to other therapeutic agents promoting the regeneration of neurons.

A further embodiment of the present invention is a method of treating central nervous system injuries comprising administering a composition comprising a chondroitinase ABCI mutant enzyme. In preferred embodiments, the chondroitinase ABCI mutant enzyme is administered in a therapeutically effective amount. In a preferred embodiment, the chondroitinase ABCI mutant enzyme used for treating central nervous system injuries is selected from the group consisting of 055D2-3 (SEQ ID NO:1), 079B6-2 (SEQ ID NO:2), 079D2-2 (SEQ ID NO:3), 057G1-1 (SEQ ID NO:4), 023G6-4 (SEQ ID NO:5) 005B12-3 (SEQ ID NO: 6), and 021B8-3 (ATCC Deposit Designation PTA-8657). More preferably, the enzyme is selected from the group consisting of 055D2-3 (SEQ ID NO:1), 079B6-2 (SEQ ID NO:2), and 023G6-4 (SEQ ID NO:5). Such central nervous system injuries may include, but are not limited to, spinal cord injuries, including trauma induced injuries, contusions, or compress injuries.

Another embodiment of the present invention is a method promoting neuronal outgrowth comprising administering a composition comprising a chondroitinase ABCI mutant enzyme. In preferred embodiments, the chondroitinase ABCI mutant enzyme is administered in a therapeutically effective amount. In a preferred embodiment, the chondroitinase ABCI mutant enzyme that promotes neuronal outgrowth is selected from the group consisting of 055D2-3 (SEQ ID NO:1), 079B6-2 (SEQ ID NO:2), 079D2-2 (SEQ ID NO:3), 057G1-1 (SEQ ID NO:4), 023G6-4 (SEQ ID NO:5) 005B12-3 (SEQ ID NO: 6), and 021B8-3 (ATCC Deposit Designation PTA-8657). More preferably, the enzyme is selected from the group consisting of 055D2-3 (SEQ ID NO:1), 079B6-2 (SEQ ID NO:2), and 023G6-4 (SEQ ID NO:5).

Other embodiments of the present invention relate to methods for promoting neurological functional recovery after central nervous system ("CNS") injury or disease. In preferred embodiments, the chondroitinase ABCI mutant enzyme is administered in a therapeutically effective amount. In particular, the present invention is directed to a method of utilizing chondroitinase to promote sensory, motor or autonomic neurological functional recovery following injury in or to the spinal cord. Compositions useful in this method include acceptable formulations of a chondroitinase ABCI mutant enzyme of the invention, including, for example, immediate release and sustained release formulations of enzyme. The present invention is also directed to a method of promoting neurological functional recovery after a contusion injury to the spinal cord. The most common types of spinal cord injuries (SCI) include contusions (bruising of the spinal cord) and compression injuries (caused by pressure on the spinal cord). In contusion injuries, the most common type of injury, a cavity or hole often forms in the center of the spinal cord. The ABCI mutant enzymes of the invention can also be used to degrade CSPGs. Accordingly, an embodiment of the invention includes a method of degrading one or more CSPGs using a composition comprising an ABCI mutant enzyme of the invention. Preferably a composition of the invention effective for promoting neurological functional recovery comprises a chondroitinase ABCI mutant enzyme selected from 055D2-3 (SEQ ID NO:1), 079B6-2 (SEQ ID NO:2), 079D2-2 (SEQ ID NO:3), 057G1-1 (SEQ ID NO:4), 023G6-4 (SEQ ID NO:5) 005B12-3 (SEQ ID NO: 6), and 021B8-3 (ATCC Deposit Designation PTA-8657).

One embodiment of the present invention is a composition and a method for its use that facilitates the access and distribution of a therapeutic and diagnostic agent in the composition into cells, through membranes or into tissues by the use of composition that includes at least one enzyme capable of cleaving proteoglycans. Preferably the composition comprises a chondroitinase ABCI mutant enzyme selected from 055D2-3 (SEQ ID NO:1), 079B6-2 (SEQ ID NO:2), 079D2-2 (SEQ ID NO:3), 057G1-1 (SEQ ID NO:4), 023G6-4 (SEQ ID NO:5) 005B12-3 (SEQ ID NO: 6), and 021B8-3 (ATCC Deposit Designation PTA-8657). The molecules or agents in the composition may include one or more of growth factors including, for example, Brain Derived Neurotrophic Factor, Insulin-like Growth Factor, Fibroblast Growth Factor, Ciliary Neurotrophic Factor, Glial Derived Neurotrophic Factor, Transforming Growth Factor, Glial Growth Factor 2, L1, GM1, Vascular Endothelial Growth Factor, Nerve Growth Factor, and Immunophilins. The composition in some embodiments comprises a fluorescent or contrast agent for imaging. According to an embodiment, the agent includes a cell for transplant, for example a stem cell or neuron, a cell as a delivery agent, a chemotherapeutic agent, an antibiotic, an antibody, or a Nogo receptor antagonist. The compositions can be used for treating a CNS injury. Preferably the composition is used in the treatment of neuronal damage from a contusion injury.

The treatments described herein deliver an amount of a chondroitinase ABCI mutant enzyme effective to degrade CSPGs and thereby promote, for example, the recovery of neurological function, optionally including a therapeutic agent, to the CNS. Such methods may include optionally administering, in combination with a chondroitinase ABCI mutant enzyme of the invention, another chondroitinase, including, but not limited to chondroitinase ABCI, chondroitinase ABCII, chondroitinase AC and chondroitinase B or co-administering a mammalian enzyme with chondroitinase-like activity, such as hyaluronidases Hyal1, Hyal2, Hyal3, Hyal4, and PH20 preferably to the CNS, and more preferably to the lesions of the injured area of the CNS. Once the proteins or polypeptides in the compositions have been purified to the extent desired, they may be suspended or diluted in an appropriate physiological carrier or excipient for treatment.

Chondroitinase may be obtained from various sources, including a microorganism that naturally expresses a chondroitinase; for example, but not limited to, *E. coli, Proteus vulgaris*, or from the expression of a recombinant protein in a host cell. The host cell can be a prokaryotic cell (such as *E. coli*) or a eukaryotic cell (such as yeast, a mammalian cell or an insect cell).

The chondroitinase ABCI mutant nucleic acids of the present invention may be obtained by a number of methods known in the art. For example, one may use the polymerase chain reaction and/or other techniques to generate mutations in the wild type *P. vulgaris* or other chondroitinase encoding sequence. In an embodiment, the invention includes a method of making a nucleic acid sequence that encodes a chondroitinase ABCI mutant enzyme selected from 055D2-3 (SEQ ID NO:1), 079B6-2 (SEQ ID NO:2), 079D2-2 (SEQ ID NO:3), 057G1-1 (SEQ ID NO:4), 023G6-4 (SEQ ID NO:5) 005B12-3 (SEQ ID NO: 6), and 021B8-3 (ATCC Deposit Designation PTA-8657). Preferably, the invention includes a method of making a nucleic acid sequence of the invention, wherein the nucleic acid is selected from 055D2-3 nucleic acid (SEQ ID NO:9), 079B6-2 nucleic acid (SEQ ID NO:10), 079D2-2 nucleic acid (SEQ ID NO:11), 057G1-1 nucleic acid (SEQ ID NO:12), 023G6-4 nucleic acid (SEQ ID NO:13) 005B12-3 nucleic acid (SEQ ID NO: 14), and 021B8-3 (ATCC Deposit Designation PTA-8657).

Expression of a recombinant ABCI mutant nucleic acid sequence of the invention can be performed by ligating a nucleic acid encoding the ABCI mutant protein, or a portion thereof, into a vector suitable for expression in either prokaryotic cells, eukaryotic cells, or both. Procedures for ligation are well known to those of ordinary skill in the art. Expression vectors for production of recombinant forms of the subject chondroitinase polypeptides include plasmids and other vectors. For instance, suitable vectors for the expression of a chondroitinase ABCI mutant polypeptide include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast and could be used to express a recombinant ABCI mutant protein of the invention. For instance, YEP24, YIP5, YEP51, YEP52, pYES2, and YRP17 are cloning and expression vehicles useful in the introduction of genetic constructs into *S. cerevisiae* (see, for example, Broach et al. (1983) in *Experimental Manipulation of Gene Expression*, ed. M. Inouye Academic Press, p. 83, incorporated by reference herein).

In another embodiment, a chondroitinase ABCI mutant polypeptide of the invention is produced recombinantly utilizing an expression vector generated by subcloning the coding sequence of one of the chondroitinase proteins represented in 055D2-3 (SEQ ID NO:1), 079B6-2 (SEQ ID NO:2), 079D2-2 (SEQ ID NO:3), 057G1-1 (SEQ ID NO:4), 023G6-4 (SEQ ID NO:5) 005B12-3 (SEQ ID NO: 6), and 021B8-3 (ATCC Deposit Designation PTA-8657).

In some instances, it may be desirable to express a recombinant chondroitinase ABCI mutant polypeptide of the invention by the use of an insect expression system such as the baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

The expression vectors and host cells listed herein are provided by way of example only and represent the well-known systems available to those of ordinary skill in the art that may be useful to express the nucleic acid molecules. The person of ordinary skill in the art would be aware of other systems suitable for maintenance propagation or expression of the nucleic acid molecules described herein.

The enzymes of the invention may be formulated into pharmaceutical compositions and formulations. Suitable stable formulations and methods of purification are set forth in co-pending PCT Application No. US2005/017464 filed May 18, 2005 entitled "Methods of Purifying Chondroitinase and Stable Formulations Thereof" herein incorporated by reference in its entirety.

Various embodiments provide a stable formulation of a chondroitinase ABCI mutant enzyme of the invention for both storage and administration. Generally, the enzyme of such stable formulations exhibit at least about 50% of activity at about 24 hours, preferably at least about 75% of activity, more preferably at least about 85% of activity. In another aspect of the invention, the formulations consistently provide stable chondroitinase activity.

In one embodiment, the chondroitinase is formulated in a phosphate buffer, preferably a sodium phosphate buffer with a concentration in the range of about 50 mM to about 1 M. A preferred embodiment is about 750 mM sodium phosphate. Another preferred embodiment is about 100 mM sodium phosphate. In a further embodiment the chondroitinase may be formulated in a sodium phosphate buffer that further comprises sodium acetate. Sodium acetate may be present in the range of 25 mM to about 75 mM. In a preferred embodiment the sodium acetate concentration is about 50 mM. In one embodiment a preferred formulation for administration is a chondroitinase in a buffer with a pH of about 7.4. Further embodiments of formulations for storage and administration are provided in the Examples described.

In further embodiments, a formulation comprising a purified chondroitinase ABCI mutant enzyme of the invention and a buffer comprising an increased ionic strength is provided. Embodiments wherein a formulation comprises an increased ionic concentration may increase stability of an enzyme formulation. For example, a preferred embodiment provides a formulation with about 1 M NaCl in sodium phosphate. The concentration of sodium phosphate may be about 50 mM. In a preferred embodiment, the enzyme storage concentration is below about 0.4 mg/ml.

In one embodiment, a chondroitinase ABCI mutant enzyme formulation comprises about 0.4 mg/ml of a chondroitinase ABCI mutant enzyme of the invention in about 100 mM Na phosphate, at a pH of about 7.4 with a preferred substrate specificity for chondroitin A, B, and C about the same.

Various embodiments provide a stable formulation of a chondroitinase ABCI mutant enzyme of the invention for both storage and administration. Generally, the enzyme of such stable formulations exhibit at least about 50% of activity at about 24 hours, preferably at least about 75% of activity, more preferably at least about 85% of activity. In another aspect of the invention, the formulations consistently provide stable chondroitinase activity.

In another embodiment, a chondroitinase ABCI mutant enzyme purification is provided comprising the following steps: 1) extracting the enzyme from a cell, 2) separating the crude cell extract using cation-exchange chromatography, 3) further separating the extract by a gel filtration chromatography, and 4) removing endotoxin through an anion-exchange membrane to produce a purified chondroitinase ABCI mutant enzyme of the invention. In an embodiment a purified chondroitinase ABCI of the invention is dialyzed into a volatile buffer, lyophilized and stored at −80° C.

Chondroitinase activity can be stabilized by the addition of excipients or by lyophilization. Stabilizers include carbohydrates, amino acids, fatty acids, and surfactants and are known to those skilled in the art. Examples include carbohydrates such as sucrose, lactose, mannitol, and dextran, proteins such as albumin and protamine, amino acids such as arginine, glycine, and threonine, surfactants such as TWEEN® and PLURONIC®, salts such as calcium chloride and sodium phosphate, and lipids such as fatty acids, phospholipids, and bile salts.

Chondroitinase ABCI mutant enzymes of the invention may be administered topically, locally or systemically. Topical or local administration is preferable for greater control of application. An enzyme of the invention, singularly or in combination with other enzymes of the invention or with other CSPG-degrading enzymes, can be mixed with an appropriate pharmaceutical carrier prior to administration. Administration includes delivery of the enzyme to the site of injury or site at which CSPGs to be degraded are found. Examples of generally used pharmaceutical carriers and additives are conventional diluents, binders, lubricants, coloring agents, disintegrating agents, buffer agents, isotonizing fatty acids, isotonizing agents, preservants, anesthetics, surfactants and the like, and are known to those skilled in the art. Pharmaceutical carriers that may be used include dextran, sucrose, lactose, maltose, xylose, trehalose, mannitol, xylitol, sorbitol, inositol, serum albumin, gelatin, creatinine, polyethylene glycol, non-ionic surfactants (e.g. polyoxyethylene sorbitan fatty acid esters, polyoxyethylene hardened castor oil, sucrose fatty acid esters, polyoxyethylene polyoxypropylene glycol) and similar compounds.

A treatment regimen according to the invention may be carried out by a means of administering a composition comprising a chondroitinase ABCI mutant enzyme of the present invention. The treatment regimen may further comprise administering chondroitinase ABCI, chondroitinase ABCII, chondroitinase AC and chondroitinase B or mammalian enzymes with chondroitinase-like activity such as hyaluronidases Hyal1, Hyal2, Hyal3, Hyal4 and PH20 to the lesions of the injured area of the CNS. The mode of administration, the timing of administration and the dosage are carried out such that the functional recovery from impairment of the CNS is enhanced by the promotion of neurite outgrowth.

The effective amount of chondroitinase can be administered in a single dosage, two dosages or a plurality of dosages. Although it is to be understood that the dosage may be administered at any time, in one embodiment, the dosage is administered within 12 hours after injury, or as soon as is feasible. In another embodiment, the dosage is administered to an injured mammal in one, two or a plurality of dosages; such dosages would be dependant on the severity of the injury and the amount of CSPGs present in the glial scarring. Where a plurality of dosages is administered, they may be delivered on a daily, weekly, or bi-weekly basis. The delivery of the dosages may be by means of catheter or syringe. Alternatively, the treatment can be administered during surgery to allow direct application to the glial scar.

For example, in some aspects, the invention is directed to a pharmaceutical composition comprising a compound, as defined above, and a pharmaceutically acceptable carrier or diluent, or an effective amount of a pharmaceutical composition comprising a compound as defined above.

The compounds of the present invention can be administered in the conventional manner by any route where they are active. Administration can be systemic, topical, or oral. For example, administration can be, but is not limited to, parenteral, subcutaneous, intravenous, intramuscular, intraperitoneal, transdermal, oral, buccal, or ocular routes, or intravaginally, by inhalation, by depot injections, or by implants. Thus, modes of administration for the compounds of the present invention (either alone or in combination with other pharmaceuticals) can be, but are not limited to, sublingual, injectable (including short-acting, depot, implant and pellet forms injected subcutaneously or intramuscularly), or by use of vaginal creams, suppositories, pessaries, vaginal rings, rectal suppositories, intrauterine devices, and transdermal forms such as patches and creams.

Specific modes of administration will depend on the indication. The selection of the specific route of administration and the dose regimen is to be adjusted or titrated by the clinician according to methods known to the clinician in order to obtain the optimal clinical response. The amount of compound to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician).

Pharmaceutical formulations containing the compounds of the present invention and a suitable carrier can be solid dosage forms which include, but are not limited to, tablets, capsules, cachets, pellets, pills, powders and granules; topical dosage forms which include, but are not limited to, solutions, powders, fluid emulsions, fluid suspensions, semi-solids, ointments, pastes, creams, gels and jellies, and foams; and parenteral dosage forms which include, but are not limited to, solutions, suspensions, emulsions, and dry powder; comprising an effective amount of a polymer or copolymer of the present invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, *Modern Pharmaceutics*, Banker & Rhodes, 4$^{th}$ Ed., Informa Healthcare (2002); and *Goodman & Gilman's The Pharmaceutical Basis of Therapeutics*, 10th Ed., McGraw-Hill (2001) can be consulted.

The compounds of the present invention can be formulated for parenteral administration by injection, e.g., by bolus injection or continuous infusion. The compounds can be administered by continuous infusion subcutaneously over a period of about 15 minutes to about 24 hours. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

For oral administration, the compounds can be formulated readily by combining these compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as, e.g., lactose, binders such as, e.g., starches, and/or lubricants such as, e.g., talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of, e.g., tablets or lozenges formulated in a conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compounds of the present invention can also be formulated in rectal compositions such as suppositories or retention enemas, e.g., containing conventional suppository bases such as cocoa butter or other glycerides.

In addition to the formulations described previously, the compounds of the present invention can also be formulated as a depot preparation. Such long acting formulations can be administered by implantation (for example subcutaneously or intramuscularly) or by intramuscular injection.

Depot injections can be administered at about 1 to about 6 months or longer intervals. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

In transdermal administration, the compounds of the present invention, for example, can be applied to a plaster, or can be applied by transdermal, therapeutic systems that are consequently supplied to the organism.

Pharmaceutical compositions of the compounds also can comprise suitable solid or gel phase carriers or excipients. Examples of such carriers or excipients include but are not limited to calcium carbonate, calcium phosphate, various sugars, starches, cellulose derivatives, gelatin, and polymers such as, e.g., polyethylene glycols.

The compounds of the present invention can also be administered in combination with other active ingredients, such as, for example, adjuvants, protease inhibitors, or other compatible drugs or compounds where such combination is seen to be desirable or advantageous in achieving the desired effects of the methods described herein.

The following methods are used to illustrate the various embodiments of the present invention. The methods are exemplary methods and are not meant to limit the invention.

EXAMPLE 1

The present example illustrates the generation of exemplary chondroitinase ABCI mutant enzymes and nucleic acids according to the present invention.

Cloning of Wildtype cABCI:

Chondroitinase ABCI was generated by PCR using the full-length cDNA from *P. vulgaris* and cloned in the pET15b expression vector at the NdeI and BamHI sites. The vector was expressed in *E. coli* (Prabhakar V, et al. Biochem J. 2005).

Random Mutagenesis of cABCI:

The chondroitinase ABCI gene was divided into four modules. Random mutagenesis was performed on each individual module, using the Genemorph II kit (Stratagene) to create a product containing 1-2 amino acid changes per mutant. Products were cloned and transformed into *E. coli* DH10B such that the number of colonies obtained containing the correct clone structure was at least 5-times the number of individual mutant genes predicted to exist in the DNA population. The colonies were pooled and plasmid DNA was purified and used to transform the expression strain, BL21.

Thermal Stress Assay:

*E. coli* strains expressing the mutated cABCI enzymes were clonally plated for growth and induction (Overnight Express, Novagen) in 96-well plates. *E. coli* expressing the wildtype enzyme were also included. Total protein was extracted from the resulting bacterial pellets using BPER (PIERCE) followed by a 1:50 dilution with PBS. Samples were subjected to a thermal stress of 42 degrees C. in a humidified incubator for 2 hours. Samples were then mixed with an equal volume of 0.25 mg/ml chondroitin sulfate C (Sigma), a substrate of cABCI which results in the cleavage of the GAG chains. After a 10 minute room temperature incubation, DMB reagent was added, and absorbance at 660 nm was measured. Positive hits with absorbance measurements greater than the wildtype enzyme on the same plate were counted as positive hits, indicating greater activity after thermal stress.

Creation of Recombined Library:

The ten most thermal resistant clones from modules A, B and C were recombined in a random fashion to produce a combinatorial product library. The PCR products from each module were combined in an equimolar ratio, with one molar equivalent of the corresponding wild type also present. This created a pool of 9 variant sequences for Module C, and a pool of 11 variants for both Modules A and B. A 3-way ligation was performed in which each module could only be ligated in the correct orientation with the appropriate flanking module(s) and ligated into pET15b vector DNA to produce expression clones containing full-length cABCI. The total size of this library is 1089 variant cABCI sequences. The number of colonies obtained containing the correct clone structure was at least 5-times the number of individual mutant genes predicted. The ligation was weighted to mostly produce clones containing two or three mutant modules, thereby creating new combinations of the mutations identified in the initial screening "hits."

EXAMPLE 2

The present example illustrates exemplary chondroitinase mutant enzymes of the present invention.

Thermally stable mutants were confirmed to be generated through the process of molecular evolution. The modified DMB assay identified clones with greater thermal stability at 42 degrees C. for 2 hours when compared to wildtype cABCI. Stability at this temperature is likely to confer greater stability at 37 degrees C., enabling ease of handling and delivery for in vivo studies, as indwelling mini-pumps could be utilized for dosing. Individual modules resulted in an expected range of positive hits overall as defined by study parameters.

Clones having increased thermal stability were characterized by sequencing. All nucleotide and amino acid sequences are indicated as the wild-type and then the mutant version (Wild-type to Mutant).

| Chondroitinase ABCI mutant enzyme (protein) | Amino Acid sequence | Chondroitinase ABCI mutant (nucleic acid) | Nucleotide sequence |
|---|---|---|---|
| 055D2-3 protein (SEQ ID NO. 1) | E256 to K256 | 055D2-3 nucleic acid (SEQ ID NO. 9) | T450 to C450 G766 to A766 C2295 to T2295 |
| 079B6-2 protein (SEQ ID NO. 2) | D683 to N683 | 079B6-2 nucleic acid (SEQ ID NO. 10) | G2047 to A2047 |
| 079D2-2 protein (SEQ ID NO. 3) | | 079D2-2 nucleic acid (SEQ ID NO. 11) | A1773 to G1773 G1980 to A1980 T2068 to C2068 A2076 to G2076 |
| 057G1-1 protein (SEQ ID NO. 4) | | 057G1-1 nucleic acid (SEQ ID NO. 12) | G483 to A483 T1110 to C1110 T1821 to C1821 |
| 023G6-4 protein (SEQ ID NO. 5) | I919 to F919 A736 to P736 | 023G6-4 nucleic acid (SEQ ID NO. 13) | A2755 to T2755 G2206 to C2206 |
| 005B12-3 protein (SEQ ID NO. 6) | E296 to K296 | 005B12-3 nucleic acid (SEQ ID NO. 14) | G985 to A985 |

EXAMPLE 3

Stability Assessment—Bacterial Lysate 37° C.

Stability. Wildtype and variant chondroitinase ABCI expressing E. coli were expanded and expressed in 96-well plates. Protein extracts were prepared from the resulting bacterial pellets. Pellets were lysed with BPER (Pierce) for ten minutes at room temperature and spun at 1000 g to pellet any unsolublized material. The supernatants were transferred to new containers. Protein content was normalized using a BCA protein assay. Lysates were also run on SDS-PAGE gels and Coomassie stained. The amount of enzyme produced was measured using GeneTools software (Syngene) comparing the size of the enzyme band to all other extracted protein bands (histogram copied in at end of document.) Percent of enzyme on the basis of total cell lysate protein is shown in FIG. 1.

Figure 2:
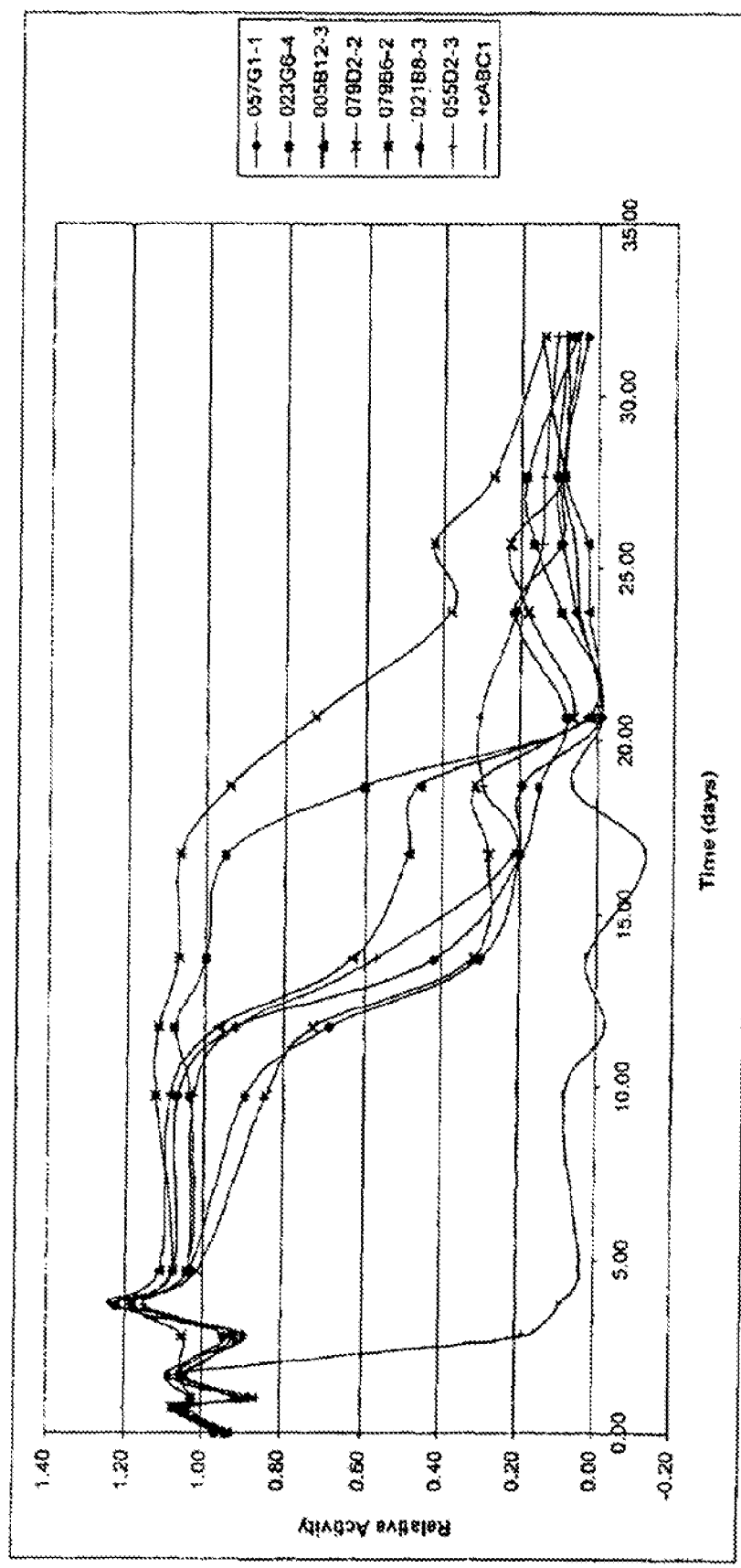
FIG. 2 shows the results of a stability assay of mutant chondroitinase ABCI whole cell lysates at 37° C., as more fully described in Example 3.

Samples were subjected to a thermal stress of 37 degrees C. in a humidified incubator. Activity was measured incrementally over time using a colorimetric DMB (Dimethyl, methylene blue) assay. Samples were mixed with an equal volume of 0.25 mg/ml chondroitin sulfate C, a substrate of chondroitinase ABCI which results in the cleavage of the GAG chains. After a ten minute room temperature incubation DMB reagent was added and the absorbance at 660 nm was measured. Results are depicted in FIG. 2 and in Tables 1A and 1B below.

TABLE 1A

| | Time (days) at 37 degrees C. | | | | | | | | |
|---|---|---|---|---|---|---|---|---|---|
| | 0.00 | 0.71 | 1.00 | 1.65 | 2.81 | 3.69 | 4.69 | 9.69 | 11.69 |
| 057G1-1 | 0.94 | 1.04 | 0.88 | 1.05 | 0.90 | 1.18 | 1.04 | 0.90 | 0.69 |
| 023G6-4 | 0.94 | 1.06 | 1.03 | 1.05 | 0.92 | 1.22 | 1.04 | 1.04 | 1.08 |
| 005B12-3 | 0.97 | 1.08 | 0.91 | 1.10 | 0.93 | 1.24 | 1.11 | 1.09 | 0.97 |
| 079D2-2 | 0.93 | 1.06 | 0.92 | 1.05 | 0.90 | 1.18 | 1.02 | 0.85 | 0.72 |
| 079B6-2 | 0.93 | 1.08 | 0.89 | 1.05 | 1.05 | 1.18 | 1.07 | 1.12 | 1.12 |
| 021B8-3 | 0.97 | 1.07 | 0.91 | 1.08 | 0.95 | 1.22 | 1.08 | 1.07 | 0.92 |
| 055D2-3 | 0.92 | 1.03 | 0.86 | 1.06 | 0.92 | 1.15 | 1.04 | 1.03 | 0.92 |
| +cABC1 | 0.95 | 1.07 | 1.02 | 1.09 | 0.18 | 0.09 | 0.03 | 0.08 | −0.03 |

TABLE 1B

Time (days) at 37 degrees C. (continued)

| | 13.69 | 16.69 | 18.69 | 20.69 | 23.69 | 25.69 | 27.69 | 31.69 |
|---|---|---|---|---|---|---|---|---|
| 057G1-1 | 0.30 | 0.20 | 0.19 | −0.01 | 0.06 | 0.09 | 0.11 | 0.08 |
| 023G6-4 | 1.00 | 0.95 | 0.60 | 0.01 | 0.09 | 0.16 | 0.18 | 0.05 |
| 005B12-3 | 0.63 | 0.49 | 0.46 | 0.02 | 0.02 | 0.03 | 0.09 | 0.15 |
| 079D2-2 | 0.32 | 0.28 | 0.32 | 0.06 | 0.18 | 0.23 | 0.09 | 0.08 |
| 079B6-2 | 1.07 | 1.07 | 0.94 | 0.73 | 0.38 | 0.42 | 0.27 | 0.14 |
| 021B8-3 | 0.42 | 0.19 | 0.15 | 0.08 | 0.22 | 0.10 | 0.10 | 0.03 |
| 055D2-3 | 0.57 | 0.21 | 0.29 | 0.30 | 0.21 | 0.14 | 0.14 | 0.11 |
| +cABC1 | 0.02 | −0.13 | 0.06 | −0.01 | 0.05 | 0.06 | 0.09 | 0.05 |

EXAMPLE 4

Semi-Purified 37° C.

Figure 3:
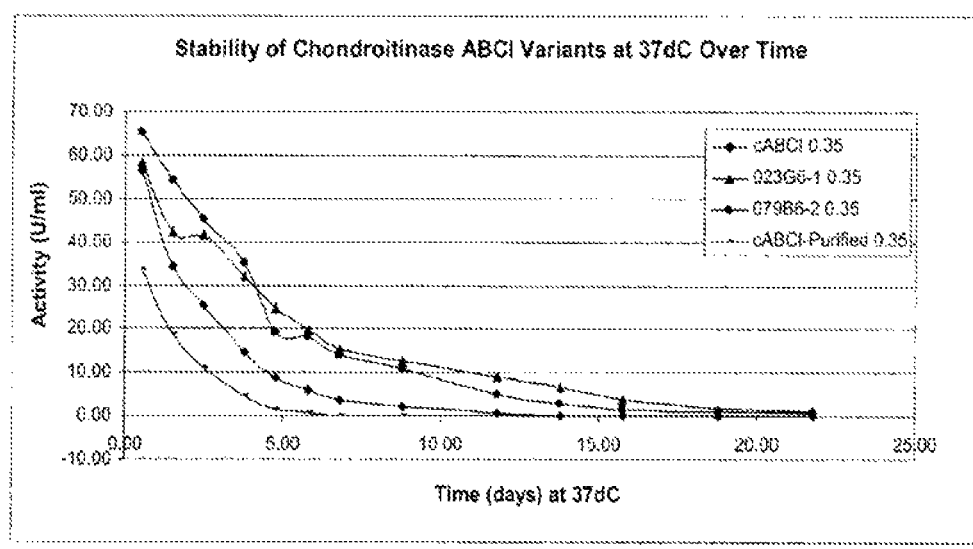
FIG. 3 shows the results of a stability assay of semi-purified mutant chondroitinase ABCI enzymes, as more fully described in Example 4.

Stability. All enzymes from wildtype and variant chondroitinase ABCI expressing *E. coli* were purified using a high speed SP column. Protein samples were normalized by A280 to match the absorbance reading of the native enzyme (0.35) by dilution in elution buffer (20 mM NaAcetate+250 mM NaCl). A fully purified cABCI enzyme was also reconstituted and diluted to an A280 of 0.35 same as the native semi-purified sample. Initial activity readings were taken for all samples using a chondroitin C substrate spectrophotometric assay. The assay measures the product produced by the digestion of chondroitin sulfate C over time at A232. Samples were subjected to a thermal stress of 37 degrees C. in a humidified incubator. Activity readings were taken every day until the native sample lost all activity. Assaying of remaining samples continued 3 times a week. Activity readings displayed as percent of total activity retained for a few variants are presented in FIG. 3 and in Tables 2A and 2B below.

TABLE 2A

Time (days) at 37 d C.

| | 0.50 | 1.50 | 2.50 | 3.79 | 4.79 | 5.79 |
|---|---|---|---|---|---|---|
| cABCI | 56.43 | 34.45 | 25.48 | 14.42 | 8.63 | 5.77 |
| 023G6-1 | 58.32 | 42.28 | 41.70 | 31.96 | 24.61 | 19.82 |
| 079B6-2 | 65.23 | 54.21 | 44.96 | 35.14 | 19.09 | 17.93 |
| cABCI-Purified | 33.78 | 18.64 | 11.21 | 4.51 | 1.59 | 0.66 |

TABLE 2B

| | 6.79 | 8.79 | 11.79 | 13.79 | 15.79 | 18.79 |
|---|---|---|---|---|---|---|
| cABCI | 3.55 | 2.23 | 0.74 | 0.00 | 0.00 | 0.00 |
| 023G6-1 | 15.23 | 12.41 | 9.00 | 6.74 | 3.76 | 1.86 |
| 079B6-2 | 13.89 | 10.76 | 5.02 | 2.89 | 1.51 | 1.10 |
| cABCI-Purified | 0.00 | 0.00 | 0.00 | 0.00 | 0.00 | 0.00 |

EXAMPLE 5

Stability of Mutant Chondroitinase Following UV Treatment.

After growth and expression, a chondroitinase mutant is extracted using BPER (Pierce) as above and exposed to UV light. The chondroitin lyase activity is measured by a DMB assay.

The present invention is not limited to the embodiments described and exemplified above, but is capable of variation and modification within the scope of the appended claims.

What is claimed is:

1. A pharmaceutical composition comprising an effective amount of mutant chondroitinase ABC I enzyme selected from SEQ ID NO: 1, SEQ ID NO: 2, SEQ ID NO: 5, SEQ ID NO:6, and combinations thereof, and a pharmaceutically acceptable carrier or diluent.

2. The pharmaceutical composition of claim 1, wherein the composition comprises mutant chondroitinase ABC I enzyme SEQ ID NO: 1.

3. The pharmaceutical composition of claim 1, wherein the composition comprises mutant chondroitinase ABC I enzyme SEQ ID NO: 2.

4. The pharmaceutical composition of claim 1, wherein the composition comprises mutant chondroitinase ABC I enzyme SEQ ID NO: 5.

5. The pharmaceutical composition of claim 1, wherein the composition comprises mutant chondroitinase ABC I enzyme SEQ ID NO: 6.

6. The pharmaceutical composition of claim 1, wherein the composition is a sustained release composition.

7. A pharmaceutical composition comprising an effective amount of a nucleic acid sequence encoding for a mutant chondroitinase ABC I enzyme, wherein the nucleic acid sequence is selected from SEQ ID NO: 9, SEQ ID NO: 10, SEQ ID NO: 13, SEQ ID NO:14, and combinations thereof, and a pharmaceutically acceptable carrier or diluent.

8. The pharmaceutical composition of claim 7, wherein the composition comprises the nucleic acid sequence of SEQ ID NO: 9.

9. The pharmaceutical composition of claim 7, wherein the composition comprises the nucleic acid sequence of SEQ ID NO: 10.

10. The pharmaceutical composition of claim 7, wherein the composition comprises the nucleic acid sequence of SEQ ID NO: 13.

11. The pharmaceutical composition of claim 7, wherein the composition comprises the nucleic acid sequence of SEQ ID NO: 14.

12. The pharmaceutical composition of claim 7, wherein the composition is a sustained release composition.

* * * * *